US007732197B2

(12) United States Patent
Norris et al.

(10) Patent No.: US 7,732,197 B2
(45) Date of Patent: Jun. 8, 2010

(54) TISSUE-SPECIFIC AND TARGET RNA-SPECIFIC RIBOZYMES

(75) Inventors: James S. Norris, Mt. Pleasant, SC (US); Gary A. Clawson, Bethesda, MD (US); Michael G. Schmidt, Mt. Pleasant, SC (US); Brian Hoel, Charleston, SC (US); Wei-Hua Pan, Hummelstown, PA (US); Joseph W. Dolan, Mt. Pleasant, SC (US)

(73) Assignees: The Penn State Research Foundation, University Park, PA (US); MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 10/082,973

(22) Filed: Feb. 26, 2002

(65) Prior Publication Data
US 2003/0092651 A1   May 15, 2003

(51) Int. Cl.
C07H 21/02 (2006.01)
C07H 21/04 (2006.01)
A61K 31/70 (2006.01)
C12Q 1/08 (2006.01)
C12N 5/00 (2006.01)
C12N 15/00 (2006.01)

(52) U.S. Cl. .............. 435/325; 424/450; 435/320.1; 435/375; 536/23.1; 536/23.2; 536/24.1; 536/24.5; 514/44 R

(58) Field of Classification Search .............. 435/91.31, 435/320.1; 536/23.1
See application file for complete search history.

(56) References Cited

U.S. PATENT DOCUMENTS

| 5,166,057 | A |   | 11/1992 | Palese et al. |
| 5,294,533 | A |   | 3/1994 | Lupski et al. |
| 5,436,330 | A |   | 7/1995 | Taira et al. |
| 5,500,357 | A | * | 3/1996 | Taira et al. ............ 435/91.31 |
| 5,578,473 | A |   | 11/1996 | Palese et al. |
| 5,599,706 | A | * | 2/1997 | Stinchcomb et al. ...... 435/366 |
| 5,670,488 | A |   | 9/1997 | Gregory et al. |
| 5,824,519 | A | * | 10/1998 | Norris et al. ............ 435/91.31 |
| 5,912,149 | A | * | 6/1999 | Ruiz et al. .............. 435/320.1 |
| 6,271,359 | B1 | * | 8/2001 | Norris et al. ............. 536/23.1 |
| 2003/0125280 | A1 | * | 7/2003 | Norris et al. ................. 514/44 |

FOREIGN PATENT DOCUMENTS

| EP | 0 640 688 | 3/1995 |
| WO | WO 90/00624 | 1/1990 |
| WO | WO 92/10590 | 6/1992 |
| WO | WO 94/03594 | 2/1994 |
| WO | WO 95/07923 | 3/1995 |
| WO | WO 97/17433 | 5/1997 |
| WO | WO 97/17458 | 5/1997 |
| WO | WO 9717433 A1 * | 5/1997 |
| WO | WO 98/17815 | 4/1998 |
| WO | WO 98/17816 | 4/1998 |
| WO | WO 98/17817 | 4/1998 |
| WO | WO 98/24925 | * 6/1998 |
| WO | WO9824925 A1 * | 6/1998 |
| WO | WO 99/67400 | 12/1999 |

OTHER PUBLICATIONS

Ohta et al. Tissue-specific expression of an anti-ras ribozyme inhibits proliferation of human malignant melanoma cells. Nucleic acid Research, vol. 24. No. 5, pp. 938-942, 1996.*
Stanley Crooke, Antisense Research and Applications, Chapter 1, Basic Principles of Antisense Therapeutics, Springer-Verlag Press, Berlin, Heidelberg, New York, p. 3, 1998.*
Andrea D. Branch, A good antisense molecule is hard to find, TIBS, 47-48, 1998.*
U.S. Appl. No. 09/291,902, filed Apr. 14, 1999, Norris et al.
U.S. Appl. No. 09/319,395, filed Jun. 3, 1999, Norris et al.
Bassford et al., "The Primary Pathway of Protein Export in E. coli," Cell, 1991, 65:789-796, 30:367-368.
Bertrand et al., "Can hammerhead ribozymes be efficient tools to inactivate gene function?" Nucleic Acids Resonant., 1994, 22(3):293-300
Bouche et al., "dnaG gene product, a rifampicin resistant RNA polymerase, initiates the conversion of a single stranded coliphage DNA to its duplex replicative form," J. Biol. Chem., 1975, 250:5995-6001.
Castanotto et al., "Antisense Catalytic RNAs as Therapeutic Agents," Adv. Pharmacol., 1994, 25:289-317.
Christoffersen et al., "Ribozymes as human therapeutic agents," J. Med. Chem., 1995, 38(12):2023-2037.
Clawson et al., "Focal altered compartmentation of repetitive B2 (Alu-like) sequences in rat liver following hepatocarcinogen exposure," Cell Growth Differ., 1996, 7(5):635-646.
Colberre-Garapin et al., "A new dominant hybrid selective marker for higher eukaryotic cells," J. Mol. Biol. 1981, 150(1):1-1.
Felgner et al., "Lipofection: a highly efficient, lipid-mediated DNA-transfection procedure," Proc. Natl. Acad. Sci. USA, 1987, 84:7413.
Gewirtz et al., "Facilitating oligonucleotide delivery: helping antisense deliver on its promise " Proc. Natl. Acad. Sci. USA, 1996, 93:3161-3163.
Greenberg et al., "The rat probasin gene promoter directs hormonally and developmentally regulated expression of a heterologous gene specifically to the prostate in transgenic mice," Mol Endo., 1994, 8(2):230-239.

(Continued)

Primary Examiner—Janet L Epps-Smith
(74) Attorney, Agent, or Firm—Fish & Richardson P.C.

(57) ABSTRACT

The present invention relates to multi-ribozymes and their use to target RNA in a tissue-specific, target RNA-specific, or pathogen-specific manner for the treatment of cancers, proliferative disease, and bacterial, parasitic and viral infections. More specifically, the present invention relates to the use of virions and viral vectors to package and deliver DNA encoding the multi-ribozymes to a host. The present invention relates to the use of liposomes and lipid-DNA complexes to deliver DNA encoding ribozymes to a host. Most specifically, the invention relates to the use of target specific virions to package and deliver DNA comprising a target specific promoter and encoding a ribozyme(s) directed to the target organism nucleic acids. The present invention further relates to a novel vectors encoding a multi-ribozyme structure with enhanced 5' and/or 3' autocatalytically cleaving ribozymes. The invention further relates to nucleotides encoding a multi-ribozyme comprising one or more ribozyme cassettes which contain one or more trans-acting ribozymes and one or more autocatalytically cleaving ribozyme sequences.

15 Claims, 12 Drawing Sheets

OTHER PUBLICATIONS

Haseloff et al., "Simple RNA enzymes with new and highly specific endoribonuclease activities," *Nature*, 1988, 334:585-591.

Inokuchi et al., "A hammerhead ribozyme inhibits the proliferation of an RNA coliphage SP in *Escherichia coli*," *J. Biol. Chem.*, 1994, 269(15):11361-11366.

Koizumi et al., "Design of RNA enzymes distinguishing a single base mutation in RNA," *Nucl. Acids Res.*, 1989, 17(17):7059-7071.

Lehnherr et al., "Plasmid addiction genes of bacteriophage P1: doc, which causes cell death on curing of prophage, and phd, which prevents host death when prophage is retained," *J Mol Biol.*, 1993, 233:414-428.

Major et al., "The combination of symbolic and numerical computation for three-dimensional modeling of RNA," *Science*, 1991, 253:1255-1260.

Marians, "Replication Fork Propagation," *Escherichia coli and Salmonella: Cellular and Molecular Biology*, $2^{nd}$ Edition, vol. 1, Neidhard (ed.), American Society for Microbiology, Washington, D.C., 1996, pp. 749-763.

Merril et al., "Long-circulating bacteriophage as antibacterial agents," *Proc. Natl. Acad. Sci. USA*, 1996, 93(8):3188-3192.

Meyer et al., "Search for a putative scrapie genome in purified prion fractions reveals a paucity of nucleic acids," *J. Gen. Virol.*, 1991, 72:1031-1038.

Miller et al., "Progress in transcriptionally targeted and regulatable vectors for genetic therapy," *Hum. Gene Ther.*, 1997, 8:803-815.

Nicolau et al., "Liposomes as carriers for in vivo gene transfer and expression," *Methods Enzymol.*, 1987, 149:157.

Ohkawa et al., "Activities of HIV-RNA targetter ribozymes transcribed from a 'shot-gun' type ribozyme-trimming plasmid," *Nucl. Acids Symp. Ser.*, 1992.

Ohme-Takagi, "In vivo RNA transcript-releasing plasmid possessing a universal pseudo-terminator by means of artificial ribozymes," *Nucl. Acids Symp. Ser.*, 1990, 22:49-50.

Pace and Smith, "Ribonuclease P: function and variation," *J. Biol. Chem.* 1990, 256(7):3587-3590.

Palese et al., "Negative-strand RNA viruses: genetic engineering and applications," *Proc. Natl. Acad. Sci. USA*, 1996, 93:11354-11358.

Poulsen et al., "The gef gene from *Escherichia coli* is regulated at the level of translation," *Mol. Microbiol.*, 1991, 5:1639-1648.

Schmidt et al., "Regulation of *Escherichia coli* secA mRNA translation by a secretion-responsive element," *J. Bacteriol.* 1991, 173 20:6605-6611.

Schmidt and Delihas, "micF RNA is a substrate for Rnase E," *FEMS Microbiol. Lett.*, 1995, 133(3):209-213.

Slopek et al., "Results of bacteriophage treatment of suppurative bacterial infections in the years," *Arch. Immunol. Ther. Exp.* (Warz), 1987, 35:569-583.

Soothill, "Treatment of experimental infections of mice with bacteriophages," *J. Med. Microbiol.*, 1992, 37(4):258-261.

Sternberg, "Recognition and cleavage of the bacteriophage P1 packaging site (pac) II. Functional limits of pac and location of pac cleavage termini," *J. Mol. Biol.*, 1987, 194(3):469-479.

Stull et al., "Antigene, ribozyme and aptamer nucleic acids drugs: progress and prospects," *Pharm. Res.*, 1995, 12(4):465-483.

Sullivan et al., "Development of ribozymes for gene therapy," *J. Invest. Dermatol.*, 1994, 103:85S-95S.

Taira et al., "Construction of a novel RNA-transcript-trimming plasmid which can be used both in vitro in place of run-off and (G)-free transcriptions and in vivo as multi-sequences transcription vectors," *Nucl. Acids Res.*, 1991, 19(9):5125-5130.

Taira et al., "Construction of several kinds of ribozymes their reactivities and utilities," *Gene Regulation, Biology of Antisense RNA and DNA*, pp. 35-54.

Taira et al., "Construction of a novel artificial-ribozyme-releasing-plasmid," *Protein Eng.*, 1990, 3(8):733-737.

Templeton et al., "Improved DNA: liposome complexes for increased systemic delivery and gene expression," *Nature Biotechnol.*, 1997, 15:647-652.

Uhlenbeck, "A small catalytic oligoribonucleotide," *Nature*, 1987, 328(6131):59.

Usman et al., "Design, synthesis, and function of therapeutic hammerhead ribozymes," *Nucl. Acids. Biol.*, 1996, 10:243-264.

Vieweg et al., "Efficient gene transfer with adeno-associated virus-based plasmids complexed to cationic liposomes for gene therapy of human prostate cancer," *Cancer Res.*, 1995, 55:2366-2372.

Whitton, "Antisense Treatment of Viral Infection," *Adv. Virus Res.*, 1994, P. 44.

Wigler et al., "Transfer of purified herpes virus thymidine kinase gene to cultured mouse cells," *Cell*, 1977, 11:223.

Wigler et al., "Transformation of mammalian cells with an amplifiable dominant-acting gene," *Proc. Natl. Acad. Sci. USA*, 1980, 77:3567.

Yuyama et al., "Construction of a T-RNA-embedded-ribozyme trimming plasmid," *Biochem. Biophys. Res. Comm.*, 1992, 186(3):1271-1279.

Zhou et al., "Expression of hammerhead ribozymes by retroviral vectors to inhibit HIV-1 replication: comparison of RNA levels and viral inhibition," *Antisense & Nucleic Acid Drug Development*, 1996, 6:17-24.

Voelkel-Johnson et al., "The use of inducible tissue specific ribozymes to functionally knock out BRCA1," *Proc. Annu. Meet. Am. Assoc. Cancer Res.*, 1997, 38, A1286.

\* cited by examiner

A.
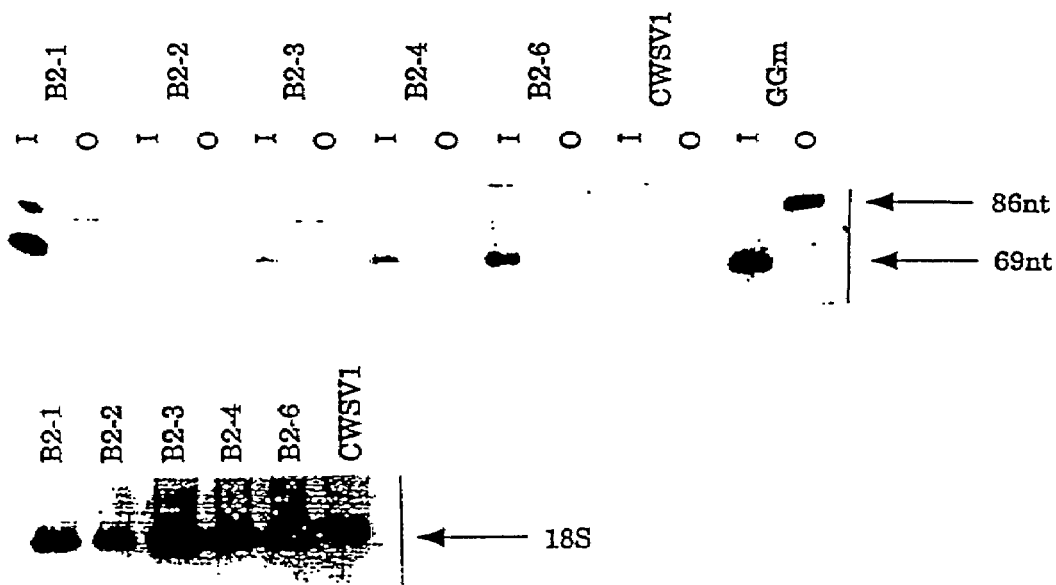
B.
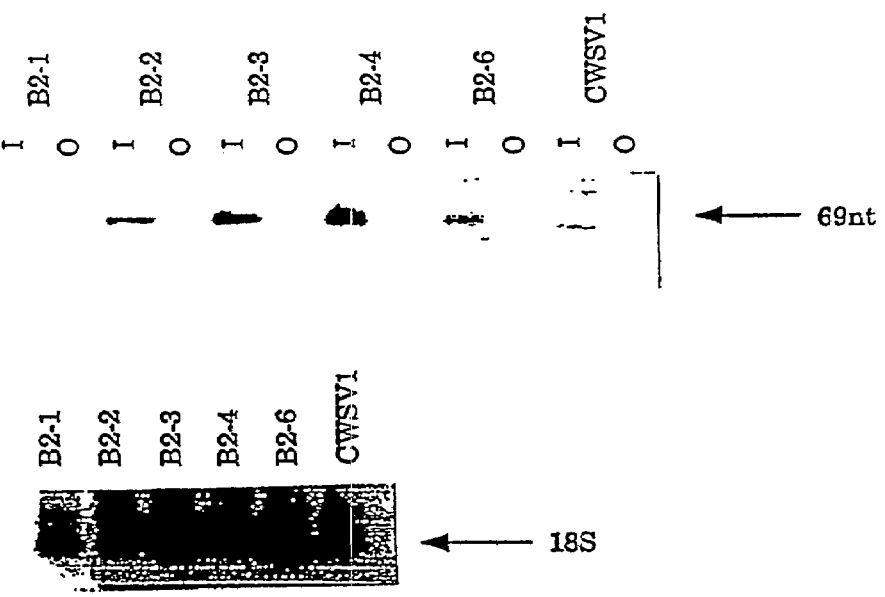
FIG. 8

|-- UPRIP (LEASHI) PROMOTER----------------------------------------------------------
5' TCAGAAAATTATTTTAAATTTCCAATTGACATTGTGAGCGGATAACAATATAATGTGTG

--|                      |---- CHOPMOD INSERT --->
GAAGCTTATCGATACCGTCGACCTCGAAGCTTTGGAACCCTGATGAGTCCGTGAGGA

CGAAACGATGACATTCTGCTGACCAGATTCACGGTCAGCAGAATGTCATCGTCGGTTC
         |-- SPACER INSERT------>
CAGGATCCGGCTGCTAACAAAGCCCGAAAGGAAGCTGAGTTGGCTGCTGCCACCGC

TGAGCAATAACTAGCATAACCCCTTGGGGCCTCTAAACGGGTCTTGAGGGGTTTTTG

CTGAAAGGAGGAACTATATCCGGATATCCCGCAAGAGGCCCGGCAGTACCGGCATAA

CCAAGCCTATGCCTACAGCATCCAGGGTGACGGTGCCGAGGATGACGATGAGCGCA

TTGTTAGATTTCATACACGGTGCCTGACTGCGTTAGCAATTTAACTGTGATAAACTACC
              END (SPACER INSERT)-----|      |-- MOD HP INSERT---
GCATTAAAGCTTATCGATGATAAGCTGTCAAACATGAGAATTCGGCGTATACGCCAA
-----|
TTTCAAGGGTCTGCGCAACGACGACGATGAGGTACCACATCGTCGTCGTTGCGCACT
                |---- TL17 TERMINATOR -----------------------
GATGAGGCCGTGAGGCCGAAACCCTTGACGCGTAAAAAAACCCGCCCCGGCGGGT
-----------|          ------END (CHOPMOD INSERT)-----|
TTTTTACCCTTCCTATGCGGCCGCTCTAGTCGAGGGGGGGCCCGCTAGAACTAG  3'

FIG. 10

Substrate-Cleavage, *In Vitro*

| RZ | fragments from p50 |
|----|--------------------|
| 615 | 290, 1326 |
| 636 | 311, 1305 |
| 649 | 324, 1292, |
| 1024 | 699, 917 |
| 1380 | 1055, 561 |
| 1438 | 1113, 503 |

SEQUENCE LISTING

```
<160> NUMBER OF SEQ ID NOS: 73

<210> SEQ ID NO 1
<211> LENGTH: 492
<212> TYPE: DNA
<213> ORGANISM: Artificial Sequence
<220> FEATURE:
<223> OTHER INFORMATION: ARN promoter

<400> SEQUENCE: 1
actcgcggat catcttcacc atcggccgca actcctgcgg gatatcctcg tcctcctcct      60
ccaccggcac ccccatggta gcggccagct cgcgccctgc ctgggaaagc tgtacatgct     120
gatcggcggc gtcggtgccg gcggccgggt cttccgcctg ctcggcggtg ccggtccgtg     180
cggccttggc gtccgcggcg gcgcgcgatg agggcggcac ctgggtggtg atccagccac     240
tgagggtcaa cattccagtc actccgggaa aaatggaatt cttccattgg atcggcccac     300
gcgtcgcgaa cttgagcccc cttttcgtcg ccccttgaca gggtgcgaca ggtagtcgca     360
gttgtttgac gcaagtcact gattggaaac gccatcggcc tgtcagaaat ggtcgttgcc     420
agacctatgg ctggcacccg catcgcggct gcgttaccct tactcctgtt gtgcctttaa     480
cctagcaagg ac                                                         492

<210> SEQ ID NO 2
<211> LENGTH: 1113
<212> TYPE: DNA
<213> ORGANISM: Artificial Sequence
<220> FEATURE:
<223> OTHER INFORMATION: PROC promoter

<400> SEQUENCE: 2
aattcctcga agtccttgcg ctgcttgtcg ttcatgatgt cgtagatcag cgcatgcacc      60
tgcttgtgtt ccagcggtgg caggttgatc cggcgtacat cgccatccac ccggatcatg     120
ggtggcaggc cggcggagag gtgcaggtcc gaagcgccct gtttggcact gaaggcgagc     180
agctcggtaa tatccatggg actccccaat tacaagcaag caggtagaat gccgccaaag     240
ccgccgtctc ggacaaggaa aacaccggat gagccagggt gcttccagga cacgcgtggt     300
gtcctgcgcc agacgcggaa cctcgacact ggaacaggaa gatggccatc gaggccggcg     360
gtttcgaggg cgtcgagccg acgccgaccg cacttccata gggcgcaggt aatgtccacg     420
atagcagaga atattgcaaa ggttgccgcg cgcatccgtg aggcagcgca agctgcgggg     480
cgcgatccgg ccacggtcgg cctgctcgcc gtgagcaaga ccaagcccgc cgccgcggtg     540
cgcgaggcgc acgccgccgg ccttcgcgac ttcggcgaaa actacctgca ggaggccctc     600
ggcaagcagg ccgaactggc cgacctgccc ttgaactggc acttcatcgg ccccatccag     660
tcgaacaaga cgcggcccat cgccgagcat ttccagtggg tgcactcggt ggaccggttg     720
aagatcgcgc agcgcctgtc ggagcaacgc ccggccgggc tgccgcccct gaatgtctgc     780
```

```
ctgcaggtca acgtcagcgg cgaagccagc aagtccggct gcgcccccga ggacctgccg    840
gccctggccg aggccgtgaa gcaactgccc aacctccgat tgcgtggcct gatggccatc    900
cccgaaccca ccgccgaacg cgccgcgcaa cacgccgcgt tcgcccgcct gcgcgaactg    960
ctgctggacc tgaaccttgg cctggacacc ctgtccatgg gcatgagcga cgacctcgag   1020
gcagccatcg gcgaaggtgc gacctgggtc cgcatcggta ccgccctgtt cggcgcccgc   1080
gactacggcg cgccggcttc ttgaatgaat ccc                                1113

<210> SEQ ID NO 3
<211> LENGTH: 66
<212> TYPE: DNA
<213> ORGANISM: Artificial Sequence
<220> FEATURE:
<223> OTHER INFORMATION: ARC promoter

<400> SEQUENCE: 3
ctagagctat tgatgtggat caacattgtc cactagccgc tgccgcctaa tctccagaat     60
tgtgag                                                                66

<210> SEQ ID NO 4
<211> LENGTH: 685
<212> TYPE: DNA
<213> ORGANISM: Artificial Sequence
<220> FEATURE:
<223> OTHER INFORMATION: UPCM2 cassette sequence

<400> SEQUENCE: 4
tcagaaaatt attttaaatt tccaattgac attgtgagcg gataacaata taatgtgtgg     60
aagcttatcg ataccgtcga cctcgaagct ttggaaccct gatgagtccg tgaggacgaa    120
acgatgacat tctgctgacc agattcacgg tcagcagaat gtcatcgtcg gttccaggat    180
ccggctgcta acaaagcccg aaaggaagct gagttggctg ctgccaccgc tgagcaataa    240
ctagcataac cccttggggc ctctaaacgg gtcttgaggg gttttttgct gaaaggagga    300
actatatccg gatatcccgc aagaggcccg gcagtaccgg cataaccaag cctatgccta    360
cagcatccag ggtgacggtg ccgaggatga cgatgagcgc attgttagat ttcatacacg    420
gtgcctgact gcgttagcaa tttaactgtg ataaactacc gcattaaagc ttatcgatga    480
taagctgtca acatgagaa ttcggcgtat acgccgaatt tcaagggtct gcgcaacgac     540
gacgatgagg taccacatcg tcgtcgttgc gcactgatga ggccgtgagg ccgaaaccct    600
tgacgcgtaa aaaaaacccg ccccggcggg tttttaccc ttcctatgcg gccgctctag     660
tcgagggggg gcccgctaga actag                                          685

<210> SEQ ID NO 5
<211> LENGTH: 673
<212> TYPE: DNA
<213> ORGANISM: Artificial Sequence
<220> FEATURE:
<223> OTHER INFORMATION: P2CM2 cassette sequence

<400> SEQUENCE: 5
agaaagcaaa aataaatgct tgacactgta gcgggaaggc gtataatgga attgtgagcg     60
gataacaatt cacaagctta tcgataccgt cgacctcgag ctttggaacc ctgatgagtc    120
cgtgaggacg aaacgatgac attctgctga ccagattcac ggtcagcaga atgtcatcgt    180
cggttccagg atccggctgc taacaaagcc cgaaaggaag ctgagttggc tgctgccacc    240
```

-continued

```
gctgagcaat aactagcata accccttggg gcctctaaac gggtcttgag gggttttttg    300
ctgaaaggag gaactatatc cggatatccc gcaagaggcc cggcagtacc ggcataacca    360
agcctatgcc tacagcatcc agggtgacgg tgccgaggat gacgatgagc gcattgttag    420
atttcataca cggtgcctga ctgcgttagc aatttaactg tgataaacta ccgcattaaa    480
gcttatcgat gataagctgt caaacatgag aattcggcgt atacgccgaa tttcaagggt    540
ctgcgcaacg acgacgatga ggtaccacat cgtcgtcgtt gcgcactgat gaggccgtga    600
ggccgaaacc cttgacgcgt aaaaaaaacc cgccccggcg ggttttttac gcgttcctat    660
gcggccgctc tag                                                      673
```

<210> SEQ ID NO 6
<211> LENGTH: 14
<212> TYPE: DNA
<213> ORGANISM: Artificial Sequence
<220> FEATURE:
<223> OTHER INFORMATION: primer

<400> SEQUENCE: 6

```
agctcgagct caga                                                      14
```

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7

```
tcgacggatc tagatcc                                                   17
```

<210> SEQ ID NO 8
<211> LENGTH: 56
<212> TYPE: DNA
<213> ORGANISM: Escherichia coli

<400> SEQUENCE: 8

```
agatctaaat cattcacctg atgagtccgt gaggacgaaa ctttagcaaa ccaagg        56
```

<210> SEQ ID NO 9
<211> LENGTH: 54
<212> TYPE: DNA
<213> ORGANISM: Escherichia coli

<400> SEQUENCE: 9

```
agatctaaat tcgtttctga tgagtccgtg aggacgaaac accacaaaag atct          54
```

<210> SEQ ID NO 10
<211> LENGTH: 54
<212> TYPE: DNA
<213> ORGANISM: Escherichia coli

<400> SEQUENCE: 10

```
agatctaaac cacatcctga tgagtccgtg aggacgaaac agtttaaacc aagg          54
```

<210> SEQ ID NO 11
<211> LENGTH: 55
<212> TYPE: DNA
<213> ORGANISM: Escherichia coli

<400> SEQUENCE: 11

```
agatctaaac gatttcctga tgagtccgtg aggacgaaac atcaccaaac caagg         55
```

<210> SEQ ID NO 12
<211> LENGTH: 56
<212> TYPE: DNA
<213> ORGANISM: Escherichia coli

<400> SEQUENCE: 12
agatctaaat gcgtctgatg agtccgtgag gacgaaacag gcaggtaaaa ccaagg    56

<210> SEQ ID NO 13
<211> LENGTH: 53
<212> TYPE: DNA
<213> ORGANISM: Streptomyces lividans

<400> SEQUENCE: 13
agatctaaag tactcctgat gagtccgtga ggacgaaacc agcgaaacca agg    53

<210> SEQ ID NO 14
<211> LENGTH: 55
<212> TYPE: DNA
<213> ORGANISM: Enterococcus faecalis

<400> SEQUENCE: 14
agatctaaaa cttttgctga tgagtccgtg aggacgaaac gtgtataaac caagg    55

<210> SEQ ID NO 15
<211> LENGTH: 54
<212> TYPE: DNA
<213> ORGANISM: Psudeomonas putida

<400> SEQUENCE: 15
agatctaaat cgctttctga tgagtccgtg aggacgaaac gtgataaacc aagg    54

<210> SEQ ID NO 16
<211> LENGTH: 54
<212> TYPE: DNA
<213> ORGANISM: Streptomyces coelicolor

<400> SEQUENCE: 16
agatctaaag tcgatgctga tgagtccgtg aggacgaaac ttcgcaaacc aagg    54

<210> SEQ ID NO 17
<211> LENGTH: 56
<212> TYPE: DNA
<213> ORGANISM: Staphylococcus warneri

<400> SEQUENCE: 17
agatctaaat gcgtctgatg agtccgtgag gacgaaacag gcaggcgaaa ccaagg    56

<210> SEQ ID NO 18
<211> LENGTH: 38
<212> TYPE: DNA
<213> ORGANISM: Artificial Sequence
<220> FEATURE:
<223> OTHER INFORMATION: B2 consensus

<400> SEQUENCE: 18
tgctcttctg atgagtccgt gaggacgaaa ccgcctga    38

<210> SEQ ID NO 19
<211> LENGTH: 39
<212> TYPE: DNA
<213> ORGANISM: Mus musculus

<400> SEQUENCE: 19
ttcaaagact gatgagtccg tgaggacgaa acgaggatc                                  39

<210> SEQ ID NO 20
<211> LENGTH: 34
<212> TYPE: DNA
<213> ORGANISM: Mus musculus

<400> SEQUENCE: 20
gtccatctga tgagtccgtg aggacgaaac cggc                                       34

<210> SEQ ID NO 21
<211> LENGTH: 36
<212> TYPE: DNA
<213> ORGANISM: Hepatitis B virus

<400> SEQUENCE: 21
attagagctg atgagtccgt gaggacgaaa caaacg                                     36

<210> SEQ ID NO 22
<211> LENGTH: 37
<212> TYPE: DNA
<213> ORGANISM: Human papillomavirus

<400> SEQUENCE: 22
gtcctgactg atgagtccgt gaggacgaaa cattgca                                    37

<210> SEQ ID NO 23
<211> LENGTH: 44
<212> TYPE: DNA
<213> ORGANISM: Homo sapiens

<400> SEQUENCE: 23
tccgttgtct ctgatgagtc cgtgaggacg aaacatgaca ccga                            44

<210> SEQ ID NO 24
<211> LENGTH: 39
<212> TYPE: DNA
<213> ORGANISM: Homo sapiens

<400> SEQUENCE: 24
gcgaggagct gatgagtccg tgaggacgaa acatggtgt                                  39

<210> SEQ ID NO 25
<211> LENGTH: 37
<212> TYPE: DNA
<213> ORGANISM: Mus musculus

<400> SEQUENCE: 25
aacttttctg atgagtccgt gaggacgaaa cataatg                                    37

<210> SEQ ID NO 26
<211> LENGTH: 42
<212> TYPE: DNA
<213> ORGANISM: Rattus norvegicus

<400> SEQUENCE: 26
tcgaagctgt ctgatgagtc cgtgaggacg aaaccgcgtt ga                              42

<210> SEQ ID NO 27
<211> LENGTH: 37
<212> TYPE: DNA
<213> ORGANISM: Mus musculus

```
<400> SEQUENCE: 27
atcagggtct gatgagtccg tgaggacgaa aggtgcc                              37

<210> SEQ ID NO 28
<211> LENGTH: 37
<212> TYPE: DNA
<213> ORGANISM: Rattus norvegicus

<400> SEQUENCE: 28
tcttcgactg atgagtccgt gaggacgaaa catggct                              37

<210> SEQ ID NO 29
<211> LENGTH: 37
<212> TYPE: DNA
<213> ORGANISM: Homo sapiens

<400> SEQUENCE: 29
tagcacactg atgagtccgt gaggacgaaa cgtttga                              37

<210> SEQ ID NO 30
<211> LENGTH: 36
<212> TYPE: DNA
<213> ORGANISM: Homo sapiens

<400> SEQUENCE: 30
tgcaatactg atgagtccgt gaggacgaaa ctgcct                               36

<210> SEQ ID NO 31
<211> LENGTH: 36
<212> TYPE: DNA
<213> ORGANISM: Homo sapiens

<400> SEQUENCE: 31
aagtcatctg atgagtccgt gaggacgaaa cctgga                               36

<210> SEQ ID NO 32
<211> LENGTH: 36
<212> TYPE: DNA
<213> ORGANISM: Homo sapiens

<400> SEQUENCE: 32
gataaggctg atgagtccgt gaggacgaaa ctttcc                               36

<210> SEQ ID NO 33
<211> LENGTH: 36
<212> TYPE: DNA
<213> ORGANISM: Homo sapiens

<400> SEQUENCE: 33
catattcctg atgagtccgt gaggacgaaa cactcg                               36

<210> SEQ ID NO 34
<211> LENGTH: 38
<212> TYPE: DNA
<213> ORGANISM: Homo sapiens

<400> SEQUENCE: 34
tcatgtatct gatgagtccg tgaggacgaa acaaaagg                             38

<210> SEQ ID NO 35
<211> LENGTH: 36
<212> TYPE: DNA
```

<213> ORGANISM: Homo sapiens

<400> SEQUENCE: 35
ggttaaactg atgagtccgt gaggacgaaa cttggg                                    36

<210> SEQ ID NO 36
<211> LENGTH: 36
<212> TYPE: DNA
<213> ORGANISM: Homo sapiens

<400> SEQUENCE: 36
gtccagtctg atgagtccgt gaggacgaaa cttaag                                    36

<210> SEQ ID NO 37
<211> LENGTH: 55
<212> TYPE: DNA
<213> ORGANISM: Artificial Sequence
<220> FEATURE:
<223> OTHER INFORMATION: primer

<400> SEQUENCE: 37
cccgggaatt cgtgatggcc acgcggccgc tcgagctctg atgagtccgt gagga              55

<210> SEQ ID NO 38
<211> LENGTH: 59
<212> TYPE: DNA
<213> ORGANISM: Artificial Sequence
<220> FEATURE:
<223> OTHER INFORMATION: primer

<400> SEQUENCE: 38
gacgggatcc agatctgagc tcgagctgac ggtaccgggt accgtttcgt cctcacgga          59

<210> SEQ ID NO 39
<211> LENGTH: 55
<212> TYPE: DNA
<213> ORGANISM: Artificial Sequence
<220> FEATURE:
<223> OTHER INFORMATION: primer

<400> SEQUENCE: 39
gagctcagat ctggatccgt cgacggatct agatccgtcc tgatgagtcc gtgag             55

<210> SEQ ID NO 40
<211> LENGTH: 46
<212> TYPE: DNA
<213> ORGANISM: Artificial Sequence
<220> FEATURE:
<223> OTHER INFORMATION: primer

<400> SEQUENCE: 40
ttgcttggcc agcggccgct gcagatccgt tcgtcctca cggact                         46

<210> SEQ ID NO 41
<211> LENGTH: 41
<212> TYPE: DNA
<213> ORGANISM: Artificial Sequence
<220> FEATURE:
<223> OTHER INFORMATION: primer

<400> SEQUENCE: 41
gatctgctct tctgatgagt ccgtgaggac gaaaccgctg a                             41

<210> SEQ ID NO 42
<211> LENGTH: 41

```
<212> TYPE: DNA
<213> ORGANISM: Artificial Sequence
<220> FEATURE:
<223> OTHER INFORMATION: primer

<400> SEQUENCE: 42
gatctcagcg gtttcgtcct cacggactca tcagaagagc a                          41

<210> SEQ ID NO 43
<211> LENGTH: 64
<212> TYPE: DNA
<213> ORGANISM: Artificial Sequence
<220> FEATURE:
<223> OTHER INFORMATION: ribozyme construct

<400> SEQUENCE: 43
cttggaaccg gatgccaggc atccggttgg tgcctttcgt cctcacggac tcatcagtag     60
tgaa                                                                   64

<210> SEQ ID NO 44
<211> LENGTH: 65
<212> TYPE: DNA
<213> ORGANISM: Artificial Sequence
<220> FEATURE:
<223> OTHER INFORMATION: ribozyme construct

<400> SEQUENCE: 44
cttggaaccg gatgccaggc atccggttaa gaagtttcgt cctcacggac tcatcagtta     60
cccta                                                                  65

<210> SEQ ID NO 45
<211> LENGTH: 65
<212> TYPE: DNA
<213> ORGANISM: Artificial Sequence
<220> FEATURE:
<223> OTHER INFORMATION: ribozyme construct

<400> SEQUENCE: 45
aattcaaccg gatgccaggc atccggttct caggtttcgt cctcacggac tcatcagaaa     60
atctg                                                                  65

<210> SEQ ID NO 46
<211> LENGTH: 64
<212> TYPE: DNA
<213> ORGANISM: Artificial Sequence
<220> FEATURE:
<223> OTHER INFORMATION: ribozyme construct

<400> SEQUENCE: 46
aattcaaccg gatgccaggc atccggtttg gacctttcgt cctcacggac tcatcagagc     60
gtgg                                                                   64

<210> SEQ ID NO 47
<211> LENGTH: 63
<212> TYPE: DNA
<213> ORGANISM: Artificial Sequence
<220> FEATURE:
<223> OTHER INFORMATION: ribozyme construct

<400> SEQUENCE: 47
aattcaaccg gatgccaggc atccggttca gcctttcgtc ctcacggact catcagtgtg     60
ttg                                                                    63
```

<210> SEQ ID NO 48
<211> LENGTH: 64
<212> TYPE: DNA
<213> ORGANISM: Artificial Sequence
<220> FEATURE:
<223> OTHER INFORMATION: ribozyme construct

<400> SEQUENCE: 48
aattcaaccg gatgccaggc atccggttaa cctttttcgt cctcacggac tcatcagctc    60
tacg                                                                 64

<210> SEQ ID NO 49
<211> LENGTH: 170
<212> TYPE: RNA
<213> ORGANISM: Artificial Sequence
<220> FEATURE:
<223> OTHER INFORMATION: pClip triple ribozyme
<221> NAME/KEY: modified_base
<222> LOCATION: (1)...(170)
<223> OTHER INFORMATION: n=a, c, g, or u

<400> SEQUENCE: 49
gcggccgcuc gagcucugau gaguccguga ggacgaaacg guacccggua ccgucagcuc    60
gagaucunnn nnnncugaug aguccgugag gacgaaannn nnagauccgu cgacggaucu   120
agauccgucc ugaugagucc gugaggacga acggaucug cagcggccgc                170

<210> SEQ ID NO 50
<211> LENGTH: 249
<212> TYPE: RNA
<213> ORGANISM: Artificial Sequence
<220> FEATURE:
<223> OTHER INFORMATION: pChop triple ribozyme
<220> FEATURE:
<221> NAME/KEY: modified_base
<222> LOCATION: (1)...(249)
<223> OTHER INFORMATION: n=a, c, g, or u

<400> SEQUENCE: 50
aagcuuugga acccugauga guccgugagg acgaaacgau gacauucgc ugaccagauu    60 cacggucagc agaaugucau cgucgguucc aggauccnnn nnncugauga guccgugagg   120
acgaaannnn nnnnngggaau uccaagggguc ugcgcaacga cgacgaugag guaccacauc   180
gucgucguug cgcacugaug aggccgugag gccgaaaccc uugacgcguu ccuaugcggc   240
cgcucuaga                                                            249

<210> SEQ ID NO 51
<211> LENGTH: 364
<212> TYPE: DNA
<213> ORGANISM: Artificial Sequence
<220> FEATURE:
<223> OTHER INFORMATION: pSnip ribozyme cassette

<400> SEQUENCE: 51
aagcttcgag ctctgatgag tccgtgagga cgaaacggta cccggtaccg tcagctcgac    60
ctcagatctc tcgagcaatt gatccgtcga cggatgtaga tccgtcctga tgagtccgtg   120
aggacgaaac ggatctgcag cggatatcca gctttggaac cctgatgagt ccgtgaggac   180
gaaacgatga cattctgctg accagattca cggtcagcag aatgtcatcg tcggttccag   240
gatccttgcc tgaattccaa gggtctgcgc aacgacgacg atgaggtacc acatcgtcgt   300
cgttgcgcac tgatgaggcc gtgaggccga aacccttgac gcgttcctat gcggccgctc   360

-continued taga          364

<210> SEQ ID NO 52
<211> LENGTH: 685
<212> TYPE: DNA
<213> ORGANISM: Artificial Sequence
<220> FEATURE:
<223> OTHER INFORMATION: modified pChop cassette

<400> SEQUENCE: 52
tcagaaaatt attttaaatt tccaattgac attgtgagcg gataacaata taatgtgtgg     60
aagcttatcg ataccgtcga cctcgaagct ttggaaccct gatgagtccg tgaggacgaa    120
acgatgacat tctgctgacc agattcacgg tcagcagaat gtcatcgtcg gttccaggat    180
ccggctgcta acaaagcccg aaaggaagct gagttggctg ctgccaccgc tgagcaataa    240
ctagcataac cccttggggc ctctaaacgg gtcttgaggg gttttttgct gaaaggagga    300
actatatccg gatatcccgc aagaggcccg gcagtaccgg cataaccaag cctatgccta    360
cagcatccag ggtgacggtg ccgaggatga cgatgagcgc attgttagat ttcatacacg    420
gtgcctgact gcgttagcaa tttaactgtg ataaactacc gcattaaagc ttatcgatga    480
taagctgtca acatgagaa ttcggcgtat acgccgaatt tcaagggtct gcgcaacgac     540
gacgatgagg taccacatcg tcgtcgttgc gcactgatga ggccgtgagg ccgaaaccct    600
tgacgcgtaa aaaaaacccg ccccggcggg ttttttaccc ttcctatgcg gccgctctag    660
tcgagggggg gcccgctaga actag                                          685

<210> SEQ ID NO 53
<211> LENGTH: 216
<212> TYPE: DNA
<213> ORGANISM: Artificial Sequence
<220> FEATURE:
<223> OTHER INFORMATION: pChop ribozyme cassette

<400> SEQUENCE: 53
aagcuuugga acccugauga guccgugagg acgaaacgau gacauucugc ugaccagauu     60
cacggucagc agaaugucau cgucgguucc aggauccuug ccugaauucc aaggucugc    120 gcaacgacga cgaugaggua ccacaucguc gucguugcgc acugaugagg ccgugaggcc    180
gaaacccuug acgcguuccu augcggccgc ucuaga                              216

<210> SEQ ID NO 54
<211> LENGTH: 54
<212> TYPE: DNA
<213> ORGANISM: Escherichia coli

<400> SEQUENCE: 54
agatctaaac gccgatctga tgagtccgtg aggacgaaac tttaaaaacc aagg           54

<210> SEQ ID NO 55
<211> LENGTH: 56
<212> TYPE: DNA
<213> ORGANISM: Escherichia coli

<400> SEQUENCE: 55
agatctaaac atctcactga tgagtccgtg aggacgaaac attacgaaac caaagg         56

<210> SEQ ID NO 56
<211> LENGTH: 54
<212> TYPE: DNA
<213> ORGANISM: Escherichia coli

```
<400> SEQUENCE: 56
agatctaaaa aaaaacctga tgagtccgtg aggacgaaac tggttaaaag atct          54

<210> SEQ ID NO 57
<211> LENGTH: 54
<212> TYPE: DNA
<213> ORGANISM: Escherichia coli

<400> SEQUENCE: 57
agatctaaat tatccactga tgagtccgtg aggacgaaac gggcgaaaag atct          54

<210> SEQ ID NO 58
<211> LENGTH: 54
<212> TYPE: DNA
<213> ORGANISM: Escherichia coli

<400> SEQUENCE: 58
agatctaaat cgttacctga tgagtccgtg aggacgaaac taccgaaaag atct          54

<210> SEQ ID NO 59
<211> LENGTH: 54
<212> TYPE: DNA
<213> ORGANISM: Escherichia coli

<400> SEQUENCE: 59
agatctaaat gatgttctga tgagtccgtg aggacgaaac cacttaaaag atct          54

<210> SEQ ID NO 60
<211> LENGTH: 54
<212> TYPE: DNA
<213> ORGANISM: Escherichia coli

<400> SEQUENCE: 60
agatctaaat tttccactga tgagtccgtg aggacgaaac gtgcaaaaag atct          54

<210> SEQ ID NO 61
<211> LENGTH: 55
<212> TYPE: DNA
<213> ORGANISM: Escherichia coli

<400> SEQUENCE: 61
agatctaatt gataccctga tgagtccgtg aggacgaaac agtcagaaaa gatct         55

<210> SEQ ID NO 62
<211> LENGTH: 54
<212> TYPE: DNA
<213> ORGANISM: Escherichia coli

<400> SEQUENCE: 62
agatctaaac gttagtctga tgagtccgtg aggacgaaac caacaaaacc aagg          54

<210> SEQ ID NO 63
<211> LENGTH: 54
<212> TYPE: DNA
<213> ORGANISM: Escherichia coli

<400> SEQUENCE: 63
agatctaaag gcatcactga tgagtccgtg aggacgaaac tgttaaaacc aagg          54

<210> SEQ ID NO 64
<211> LENGTH: 53
<212> TYPE: DNA
```

<213> ORGANISM: Escherichia coli

<400> SEQUENCE: 64
agatctaaaa gagcgctgat gagtccgtga ggacgaaaca gtcaaaacca agg    53

<210> SEQ ID NO 65
<211> LENGTH: 54
<212> TYPE: DNA
<213> ORGANISM: Escherichia coli

<400> SEQUENCE: 65
agatctaaat ttcgatctga tgagtccgtg aggacgaaac cagctaaacc aagg   54

<210> SEQ ID NO 66
<211> LENGTH: 53
<212> TYPE: DNA
<213> ORGANISM: Streptomyces lividans

<400> SEQUENCE: 66
agatctaaac tcgtcctgat gagtccgtga ggacgaaacg atcaaaacca agg    53

<210> SEQ ID NO 67
<211> LENGTH: 51
<212> TYPE: DNA
<213> ORGANISM: Streptomyces lividans

<400> SEQUENCE: 67
agatctaaag ggcgctgatg agtccgtgag gacgaaacgc gaaaaccaag g      51

<210> SEQ ID NO 68
<211> LENGTH: 56
<212> TYPE: DNA
<213> ORGANISM: Enterococcus faecalis

<400> SEQUENCE: 68
agatctaaaa ctaaatgctg atgagtccgt gaggacgaaa cgagttaaaa ccaagg 56

<210> SEQ ID NO 69
<211> LENGTH: 57
<212> TYPE: DNA
<213> ORGANISM: Enterococcus faecalis

<400> SEQUENCE: 69
agatctaaag tttaataact gatgagtccg tgaggacgaa acttgttcaa accaagg 57

<210> SEQ ID NO 70
<211> LENGTH: 54
<212> TYPE: DNA
<213> ORGANISM: Pseudomonas putida

<400> SEQUENCE: 70
agatctaaag gtccatctga tgagtccgtg aggacgaaac aaagcaaacc aagg   54

<210> SEQ ID NO 71
<211> LENGTH: 54
<212> TYPE: DNA
<213> ORGANISM: Pseudomonas putida

<400> SEQUENCE: 71
agatctaaac aggttcctga tgagtccgtg aggacgaaac aatgtaaacc aagg   54

<210> SEQ ID NO 72
<211> LENGTH: 54

```
-continued

<212> TYPE: DNA
<213> ORGANISM: Streptomyces coelicolor

<400> SEQUENCE: 72
agatctaaag ctcgatctga tgagtccgtg aggacgaaac gaaccaaacc aagg        54

<210> SEQ ID NO 73
<211> LENGTH: 52
<212> TYPE: DNA
<213> ORGANISM: Streptomyces coelicolor

<400> SEQUENCE: 73
agatctaaac gagtcctgat gagtccgtga ggacgaaacc gggaaaccaa gg          52
```

TISSUE-SPECIFIC AND TARGET RNA-SPECIFIC RIBOZYMES

This application claims priority, under 35 U.S.C. §119(e), of U.S. Provisional Patent Application No. 60/090,560 filed Jun. 24, 1998, and of U.S. Provisional Patent Application No. 60/096,502 filed Aug. 14, 1998, both of which are incorporated herein, by reference, in their entireties.

1. FIELD OF THE INVENTION

The present invention relates to multi-ribozymes and their use to target RNA in a tissue-specific or target-specific manner for the treatment of proliferative diseases, cancers and bacterial, parasitic and viral infections More specifically, the present invention relates to the use of virions and viral vectors to package and deliver DNA encoding the multi-ribozymes to a host. The present invention relates to the use of liposomes and lipid-DNA complexes to deliver DNA encoding ribozymes to a host. Most specifically, the invention relates to the use of target specific virions to package and deliver DNA comprising a target specific promoter and encoding a ribozyme directed to target organism nucleic acids such as ribonucleic acids. The present invention further relates to a novel vector encoding a multi-ribozyme structure with enhanced 5' and 3' autocatalytically cleaving ribozymes.

2. BACKGROUND

2.1 Ribozymes

A ribozyme is a catalytic RNA molecule that cleaves RNA in a sequence specific manner. The use of ribozymes as potential gene regulators in mammalian cells and antiviral agents has been suggested, but subject to serious questions regarding technical feasibility. For example, there are differences regarding how ribozymes can be introduced to target cells or how they can be directed to the same subcellular compartments as their target RNAs. Other questions concern the effects of target RNA secondary structure on ribozyme activity. The art has not been successful in definitively answering any of these questions.

Furthermore, because riboozymes are a form of antisense technology, the problems encountered in applying antisense technology to disease treatment are also encountered in the use of ribozyme technology (Haseloff, J., and W. L. Gerlach, 1988, Nature 334(6183):585-91; Sullivan, S. M., 1994, J. Invest Dermatol. 103(5 Supl):858-895). For example, it has been shown that the expression of antisense RNA in transgenic mice did not invariably lead to a reduction in target RNA molecules, and when reduction in target RNA molecules did occur, it was not predictably paralleled by a reduction in protein. Even when protein levels were reduced sometimes no biological effect was detected (Whitton, J. Lindsay "Antisense Treatment of Viral Infection" Adv. in Virus Res. Vol. 44, 1994).

The experience in the art suggests that it is also not clear whether ribozymes work best when free or when associated with only short non-specific flanking sequences, or when embedded in unrelated larger RNA molecule (Whitton, 1994, supra). At present, sufficient data are not available, either in vitro or in cell culture to allow systematic comparison of the transactivities of free ribozymes with their embedded equivalents.

There have been some studies that focus on the potential use of ribozyme technology in the treatment of cancer. In these studies, ribozymes have been directed against both c-fos and c-ras oncogenes in cell culture, and these showed some suppression of the malignant potential of transfected cells when transplanted into mice. Nevertheless, these ribozymes specifically target an oncogene.

There has been no suggestion in the literature that tissue-specific cancers or other tissue-specific disease can be treated by delivering to that tissue a ribozyme having a tissue-specific promoter, and that it is targeted to an RNA that is essential for cell survival. The invention provides such a ribozyme capable of treating tissue-specific cancers and other tissue-specific diseases.

2.2 Promoters

Furthermore, endogenous delivery of a ribozyme under the control of a tissue-specific or other promoter can be complicated by "leakiness", where low levels of transcription occur in extraneous tissues. This could present a considerable therapeutic problem, depending upon the cellular target chosen. The present invention compensates for this problem by targeting a cellular target which is associated with high levels of product (such as, RNA polymerase I produces large amounts of cellular ribosomal RNA). Thus, in the event promoter leakiness occurs in unintended tissues, it is not likely that cell death would occur. This choice, therefore, provides a needed level of safety, and targeting of pol I would be applicable to many selected tissues using other promoters.

2.3 Delivery

Another common problem in gene therapy is the difficulty in delivering the ribozyme to the correct tissue. The present invention avoids this difficulty by targeting the ribozyme to non-cellular RNAs in cells to which ribozyme constructs can be efficiently delivered. IV liposome delivery will be effective for treatment of HBV hepatitis. Intravenous and/or extracorporeal treatment will effectively delivery construct to erythrocytes for treatment of malarial infection. And topical (with or without iv) administration will effectively deliver ribozyme construct to cervical epithelium in dysplastic/pre-cancerous/cancerous HPV 16 cervical lesions. This latter example is of extreme importance for treatment of dysplastic/carcinoma in situ lesions diagnosed via abnormal Pap smears. A second advantageous facet of the non-cellular target ribozymes of the present invention is that even if promoter leakiness and/or extraneous delivery and/or expression of the ribozyme occurs in unintended cells, the ribozymes should not cleave the cellular RNAs.

2.4 Antimicrobial Agents

Infectious diseases sicken or kill millions of people each year. Numerous antimicrobial therapies have been designed to target one or several infectious agents. These therapies show varying degrees of success in eradicating infection. However, the failure of many of these therapies to target specific infectious agents has lead to overuse or inappropriate use of the therapies, which in turn has lead to the development of drug resistant microbes. The development of drug resistance in many infectious agents has reduced the efficacy and increased the risk of using the traditional antimicrobial therapies.

While ribozymes have been known and studied for several years, they have not been used in the treatment of bacterial infections. There are many reasons for this. A key technical concern in the use of ribozymes as antimicrobial agents is that the ribozyme must be taken up and expressed by the targeted microbe so that the ribozyme(s) can cleave the targeted RNA(s) inside the microorganism. A second important concern is the tight coupling of transcription and translation in microorganisms which can complicate efficient cleavage of targeted bacterial RNAs. These concerns are addressed by the present invention.

3. SUMMARY OF THE INVENTION

The present invention relates to multi-ribozymes and their use to target RNA in a tissue-specific or pathogen-specific manner for the treatment of cancers and proliferative disease and bacterial, parasitic and viral infections. The present invention further relates to multi-ribozymes that target pathogens.

The present invention relates to multi-ribozyme(s) which contain two separable functional regions including a "catalytic core" which cleaves the target RNA or RNAs, and flanking regions which include cis-acting autocatalytically acting ribozymes and a target RNA-specific binding site. The catalytic core contains one or more ribozymes known as transacting ribozymes. The flanking regions are located nearby or adjacent to the catalytic core, and contain ribozymes known as autocatalytically cleaving ribozymes. A catalytic core in combination with one or more flanking region(s) as used herein is referred to as a ribozyme "cassette" or "triple ribozyme" (when three ribozymes comprise a multi-ribozyme.). In several embodiments, a multi-ribozyme comprises one or more ribozyme cassette. By nucleic acid complementarity, the binding site directs the multi-ribozyme core to cleave a specific site on the target RNA molecule.

The invention also relates to multi-ribozyme structures containing modifications which enhance stability and protect against degradation, e.g., RNA hairpin loops. Examples of such modifications include those which protect against degradation by endonucleases such as modifications to the structure of the nucleotides and stabilizing hairpin loops in or near the ribozyme cassette.

The present invention relates to novel vectors encoding multi-ribozymes of the invention. The invention further relates to the use biologic delivery systems such as virions and viral vectors to package and deliver the DNA encoding the multi-ribozymes for the present invention. The invention encompasses the use of abiologic delivery systems such as liposomes and liposome-DNA or lipid-DNA complexes to deliver DNA encoding ribozymes to a host.

The invention provides tissue-specific and target RNA-specific (such as pathogen-specific) ribozymes. The ribozymes can be targeted specifically to neoplastic cells or viral infected cells in order to target RNA encoding essential gene products, and thus eliminate the neoplastic or viral infected cell. The ribozymes of present invention provides multi-ribozymes which are designed as combinations of autocatalytic and trans-acting ribozymes. The present invention further provides autocatalytically cleaving ribozymes with enhanced activity. In accordance with the present invention the multiple trans-acting ribozymes may be targeted to the same site on the same RNA, different sites on the same RNA, or different RNAs.

The present invention further provides for regulating the cellular distribution of the transacting ribozymes. The present invention encompasses the use of combinations of slow cleaving and enhanced cleaving autocatalytically cleaving ribozymes to regulate the nuclear and cytoplasmic accumulation and distribution of the trans-acting ribozymes.

The invention additionally provides nucleic acids and cassettes which encode the ribozymes of the invention. These nucleic acids can be used to express the ribozymes of the invention at a selected site. In several embodiments of the invention, the nucleic acids or expression cassettes encode a tissue-specific or target-specific promoter operably liked to a nucleic acid encoding a multi-ribozyme of the invention. In one embodiment of the invention, the nucleic acids or expression cassettes of the invention comprise a tissue-specific promoter upstream from a sequence encoding a 5' autocatalytically cleaving ribozyme sequence, a catalytic ribozyme comprising a target RNA-specific binding site and a 3' autocatalytically cleaving ribozyme sequence. In another embodiment of the invention, the nucleic acids and expression cassettes of the invention comprise a tissue-specific promoter upstream from a sequence encoding a 5' autocatalytically cleaving ribozyme sequence, a catalytic ribozyme comprising one or more target RNA-specific trans-acting ribozymes and a 3' autocatalytically cleaving ribozyme sequence.

In accordance with the present invention, the expression cassettes may be engineered to express two or more multi-ribozymes containing transacting ribozymes which act on the same or different targets. The expression cassettes may also be engineered to express one, two or more multi-ribozymes containing 5' and 3' autocatalytically cleaving ribozymes with either slow or enhanced cleavage activity.

In a preferred embodiment, the invention provides nucleic acids and expression cassettes which encode multi-ribozymes with altered cleavage sites, so that the 5' and/or 3' autocatalytically cleaving ribozymes have enhanced activity, resulting in the more effective and efficient release of the targeted internal ribozymes. In an additional preferred embodiment, the invention provides nucleic acids which encode multi-ribozymes with one or more trans-acting ribozymes, resulting in the more effective and efficient targeting of RNA-target(s). In other embodiments, the invention provides for nucleic acids that encode one or more ribozyme cassettes each containing a) a 5' autocatalytically cleaving ribozyme sequence and/or a 3' autocatalytically cleaving ribozyme; and b) catalytic ribozyme(s) comprising one or more target RNA-specific trans-acting ribozymes. In another embodiment, the expression cassettes encode autocatalytically cleaving ribozyme combinations of slow and enhanced cleavage activities thus resulting in a distribution of liberated trans-acting ribozymes between the nucleus and cytoplasm. In yet another embodiment, the expression cassette encodes enhanced autocatalytically cleaving ribozymes resulting in an increase accumulation of the liberated trans-acting ribozymes in the nucleus.

In another preferred embodiment, the present invention relates to a microbiocidal agent directed against any cellular, viral, bacterial, fungal, or other single or multicellular organism from any known taxonomic family, genus, or species, and from previously unknown, or uncharacterized organism. In yet another preferred embodiment, the present invention relates to a multi-ribozyme comprising a trans-acting ribozyme which targets any cellular, viral, bacterial, fungal, or other single or multicellular organism from any known taxonomic family, genus, or species, and from previously unknown, or uncharacterized organism. The present composition of matter has resulted from the development of a new delivery system that provides a series of ribozymes directed against fundamental and essential cellular processes specific to a targeted microorganism through an inactivated, altered, virus (virion), or abiologic delivery vehicles, capable of delivering a nucleic acid containing the ribozyme(s) into the targeted microorganism. The targeted microorganisms may be any virus, nonvirus, bacterium, or lower eukaryotes such as fungi, yeast, parasites, protozoa, or other eukaryotes that may be consider normal flora or pathogens of humans, animals, fish, plants or other forms of life.

The present invention also relates to a Multi-ribozyme ribozyme. The present Multi-ribozyme ribozyme is uniquely suited as an antimicrobial therapeutic in that upon nucleic acid hybridization with the target RNA transcript, the ribozyme-RNA complex achieves a catalytic form that acts as a nuclease to cleave the targeted RNAs. Thus, cleavage deprives the invading microorganism of essential cellular processes which then kill or render it less fit.

This approach offers new and unprecedented advances for antimicrobial therapeutics: 1) the preparation bypasses any de novo built-in drug resistance, which sophisticated microbes will be expected to have or develop, 2) cells are generally not capable of counteracting ribozymes delivered into them, 3) microbes have several broad RNA targets that can be attacked in simultaneously with probable synergy, 4) the custom design of the present delivery vehicle can be readily tailored to different families of organisms, 5) the modified delivery vehicle is a non-replicating, artificial construct easy to assemble and manufacture, 6) the preparation can be applied topically or it can be delivered via injection, inhalation, or ingestion, 7) the preparation can be lyophilized and thus confer stability to the antimicrobial therapeutic, 8) the inhalant, ingested or topical form of the antimicrobial therapeutic reduces the immunogenicity of the multi-ribozyme preparations as opposed to its parenteral use, and 9) animal test systems exist that enable the evaluation of the multi-ribozyme in a measured, incremental fashion to quickly determine the efficacy of the antimicrobial therapeutic agent. Therefore, the combination of the present unique delivery approach and an aggressive mechanism for depriving the microbial cells of essential gene products can achieve the timely defeat of microbes within the host.

The targets of the antimicrobial multi-ribozyme therapeutic described herein are the RNAs of invading or normal flora microorganisms. The invention provides the delivery of a series of ribozymes directed towards essential, housekeeping, or virulence genes of one or a series of candidate microorganisms. A ribozyme is uniquely suited as the active component of the present antimicrobial therapeutic in that it is a catalytic RNA molecule that cleaves RNA in a sequence specific manner. Therefore, the catalytically active component of a multi-ribozyme contains ribozymes that have been designed to inactivate RNA coding for components of the microbial cell. Inactivation of essential proteins and virulence determinants render the invading microbes inactive or slow their growth, while at the same time, the essential processes of the host are not affected.

At the molecular genetic level, the coding sequence for a ribozyme or the multi-ribozyme may be placed under the control of one or more of the following genetic elements: a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of ribozyme expression. This genetic information is delivered into the microbe by either a biologic (e.g., a modified virus) or abiologic delivery vehicle.

In one embodiment of the present invention, when a biologic vehicle is used, the nucleic acids encoding the multi-ribozymes are unique in that they contains sufficient genetic information for expression of the ribozyme(s) and such genetic information necessary and sufficient for its assembly and delivery to the targeted microorganism, but does not include nucleic acids native to the virus. Thus, the virion can serve as a molecular vehicle that delivers the inactivating ribozyme(s). Alternatively, an abiologic delivery system (e.g., liposomes) can be used to package nucleic acid carrying the genetic elements necessary and sufficient for the proper expression of the ribozyme(s).

In yet another embodiment, the present invention relates to a novel vector encoding multi-ribozyme structures. The present invention also relates to a novel vector encoding multi-ribozyme structures with enhanced 5' and/or 3' autocatalytically cleaving ribozymes. The novel vectors of the present invention encode unique 5' and 3' autocatalytically cleaving activity, so that the internally encoded ribozymes are rapidly and effectively released. The novel vectors of the present invention may be used to engineer a wide variety of ribozymes including, but not limited to, tissue and/or promoter specific ribozymes, anti-microbial ribozymes, anti-viral ribozymes, anticancer ribozymes, anti-proliferative ribozymes, anti-tumor ribozymes.

The present invention further encompasses the use of the multi-ribozymes of the present invention for the treatment of disease, viral infection, parasitic infection, and microbial infection. The present invention further encompasses the use of the multi-ribozymes of the present invention for the treatment of proliferative disease such as neoplasms, malignancies, and other cancers. The present invention further relates to a method of treating a subject having a proliferative disease of a specific tissue by inhibiting cell proliferation in the tissue, comprising administering to the subject a multi-ribozyme wherein the target-specific promoter binding sequence is specific for the diseased tissue, whereby the ribozyme encoded by the nucleic acid is expressed, ribosomal RNA production in the tissue is inhibited, cell proliferation is inhibited, and the proliferative disease is treated or ameliorated.

The present invention further relates to a method of treating a subject having a proliferative disease of a specific tissue by inhibiting cell proliferation in the tissue, comprising administering to the subject a multi-ribozyme wherein the tissue-specific promoter binding sequence is specific for the diseased tissue, whereby the ribozyme(s) encoded by the nucleic acid is expressed, ribosomal RNA production in the tissue is inhibited, cell proliferation is inhibited, and the proliferative disease is treated or ameliorated.

The present invention encompasses the multi-ribozymes of the present invention in pharmaceutical formulations.

The present invention encompasses the use of the multi-ribozymes of the present invention for research and screening purposes. In one embodiment of the present invention, the multi-ribozymes may be used to screen for viral or microbial gene products to be targeted in order to effectively inhibit the life cycle of the virus or microbial agent. In another embodiment of the invention, a library of sequences (e.g., a ribozyme library) is used to screen for trans-acting ribozymes that may be directed to a particular target RNA or an unknown RNA target.

4. BRIEF DESCRIPTION OF THE DRAWINGS

FIG. 1D shows the sequence specific hybridization of the ribozyme. The internal or trans-acting ribozymes comprise two trans-acting ribozymes linked by a short nucleotide "spacer". Each of the two trans-acting ribozymes contain a sequence that is reverse and complementary to the targeted message. The ribozyme is synthesized at a concentration sufficient to locate and hybridize to all or substantially all targeted transcripts.

FIG. 1E shows the trans-catalytic cleavage. Upon hybridization of the internal ribozyme to the targeted mRNA transcript, the internal ribozyme achieves a catalytic topology and cleaves the targeted message. Upon cleavage the trans acting ribozyme is released and its activity and function are recycled.

Figure 2:
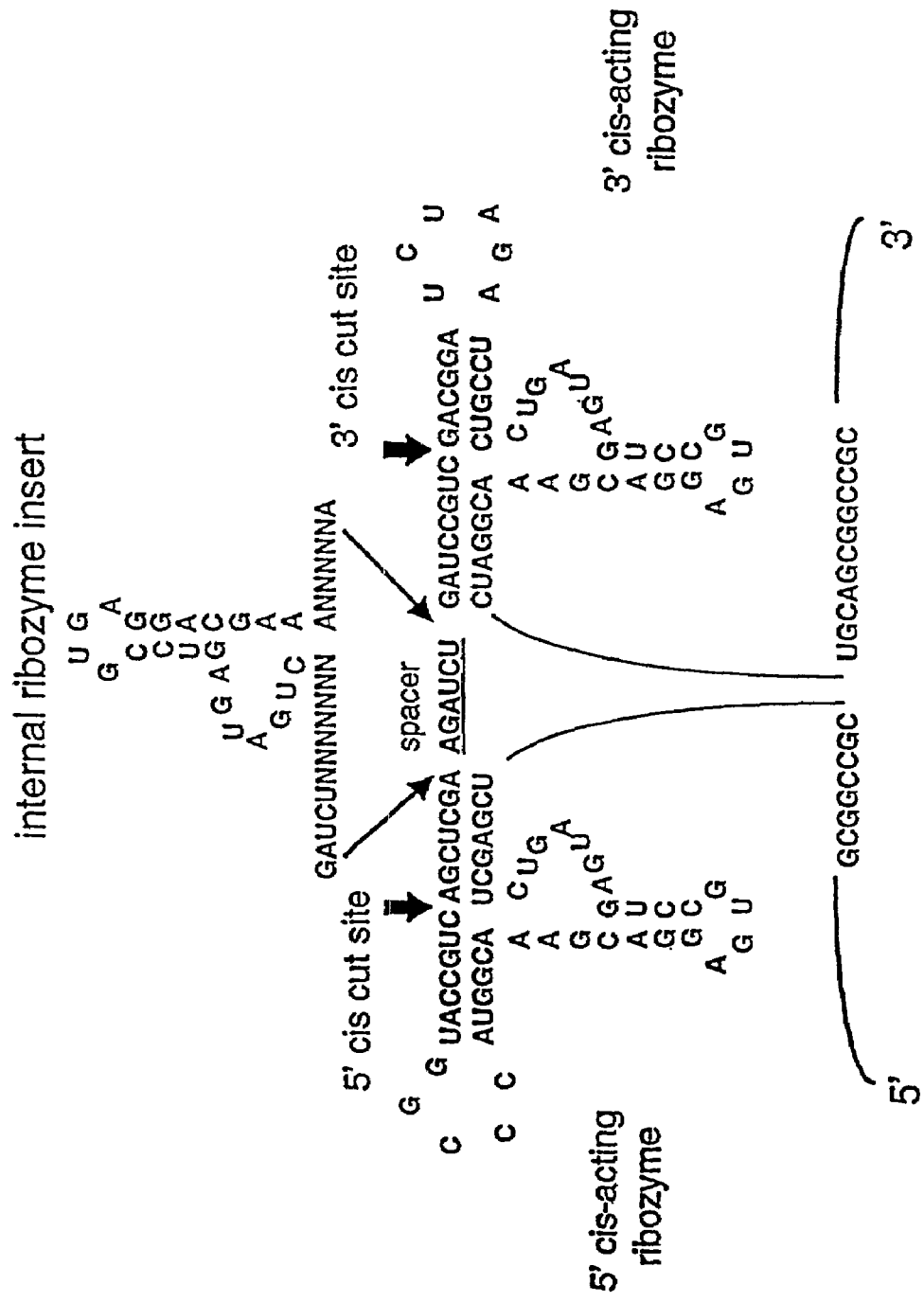

FIG. 2 Diagram and nucleotide sequence of the pClip ribozyme cassette (SEQ ID NO:49).

Figure 3:
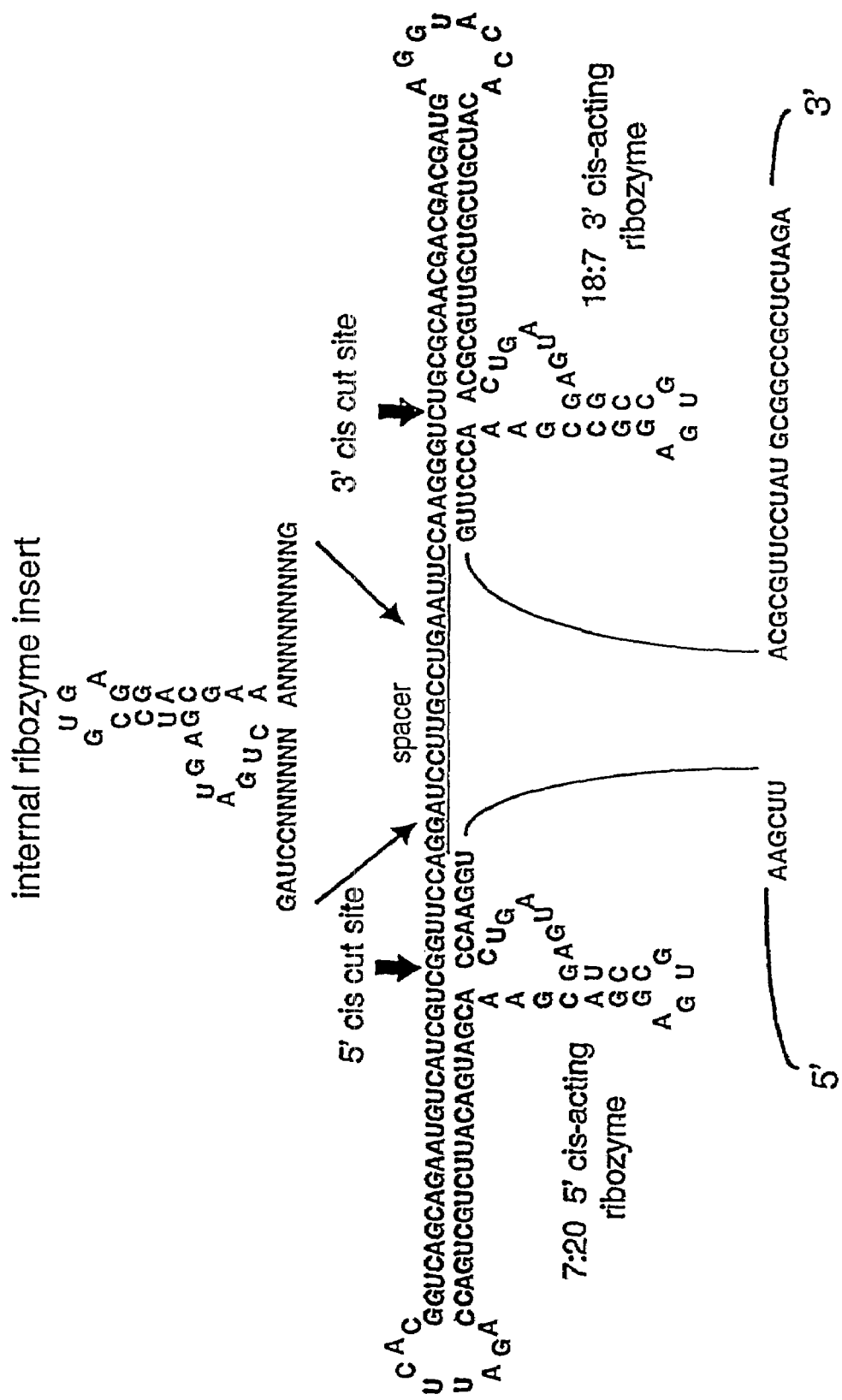

FIG. 3 Diagram and nucleotide sequence of the pChop ribozyme cassette (SEQ ID NOs:50 and 53).

Figure 4:
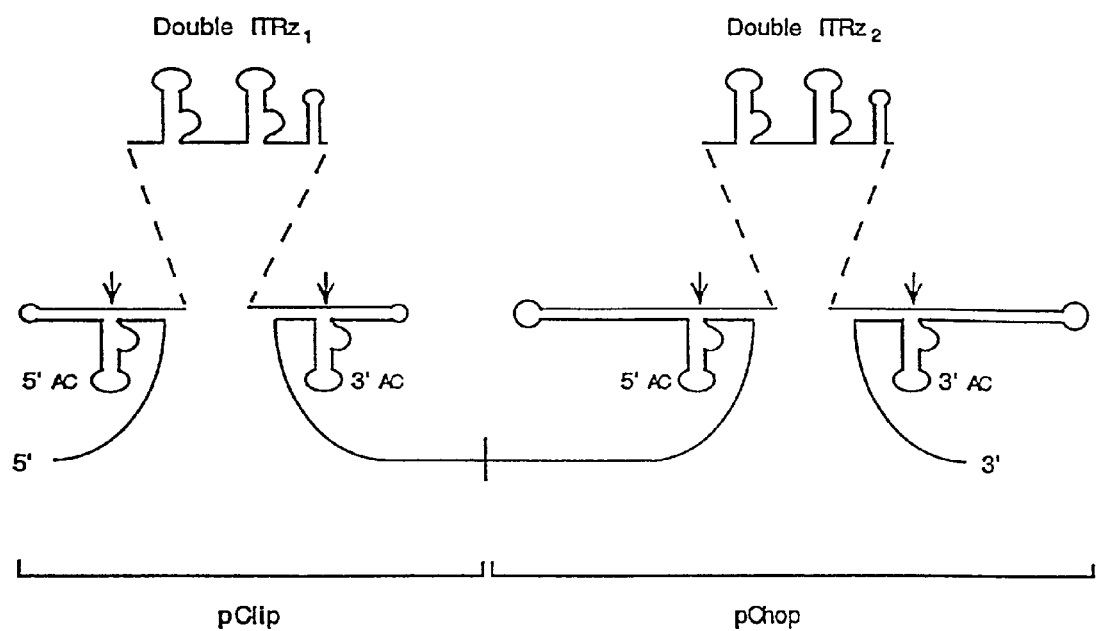
Figure 5:
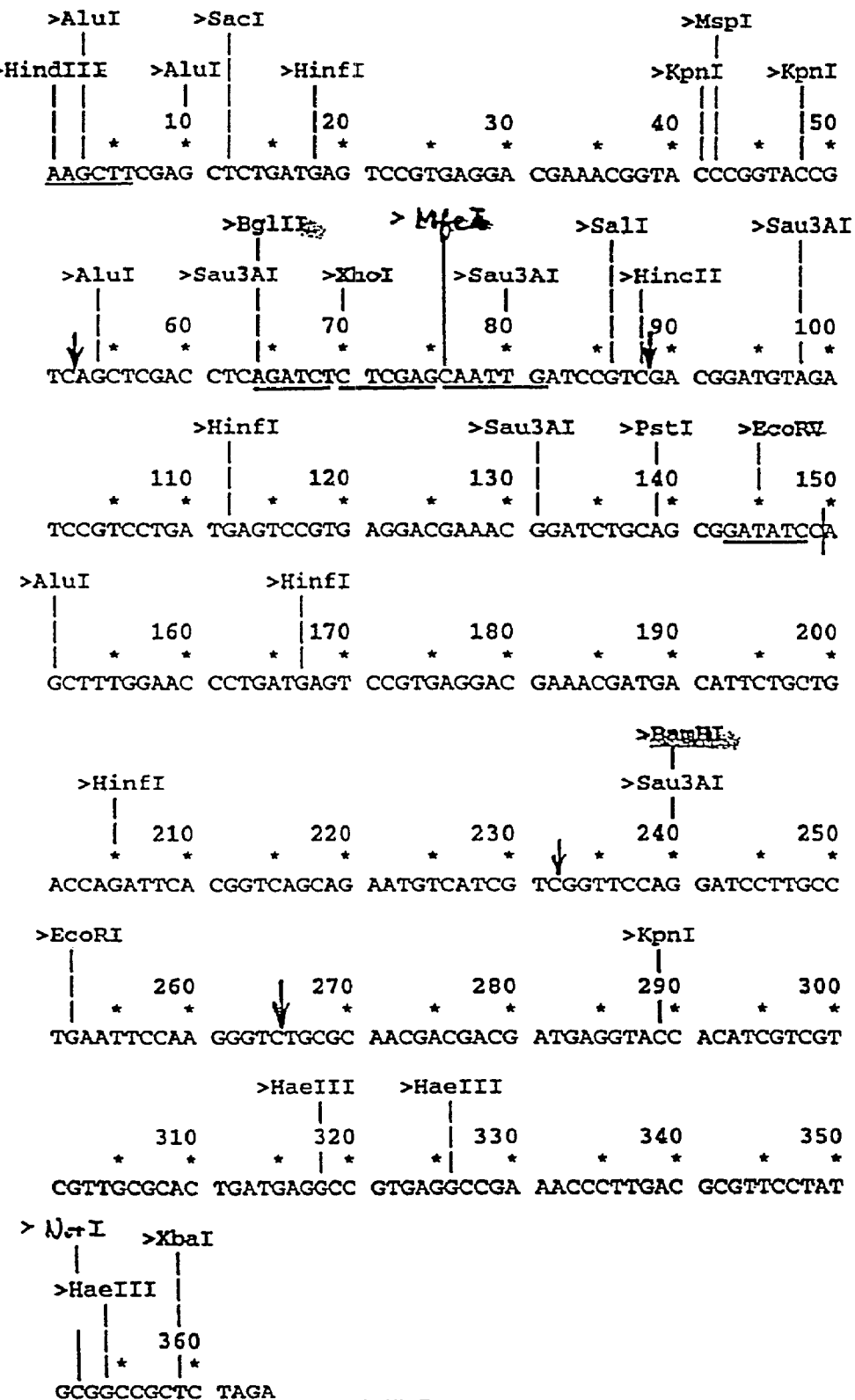

FIG. 4 Schematic diagram of the pSnip ribozyme cassette. pSnip includes sequences of the pClip triple ribozyme cassette, catalytic core targeted ribozymes comprising two linked trans-acting ribozymes, and sequences from the pChop triple ribozyme cassette FIG. 5 Nucleotide sequence of pSnip, shown without the double trans-acting ribozyme inserts (SEQ ID NO:51).

Figure 6:
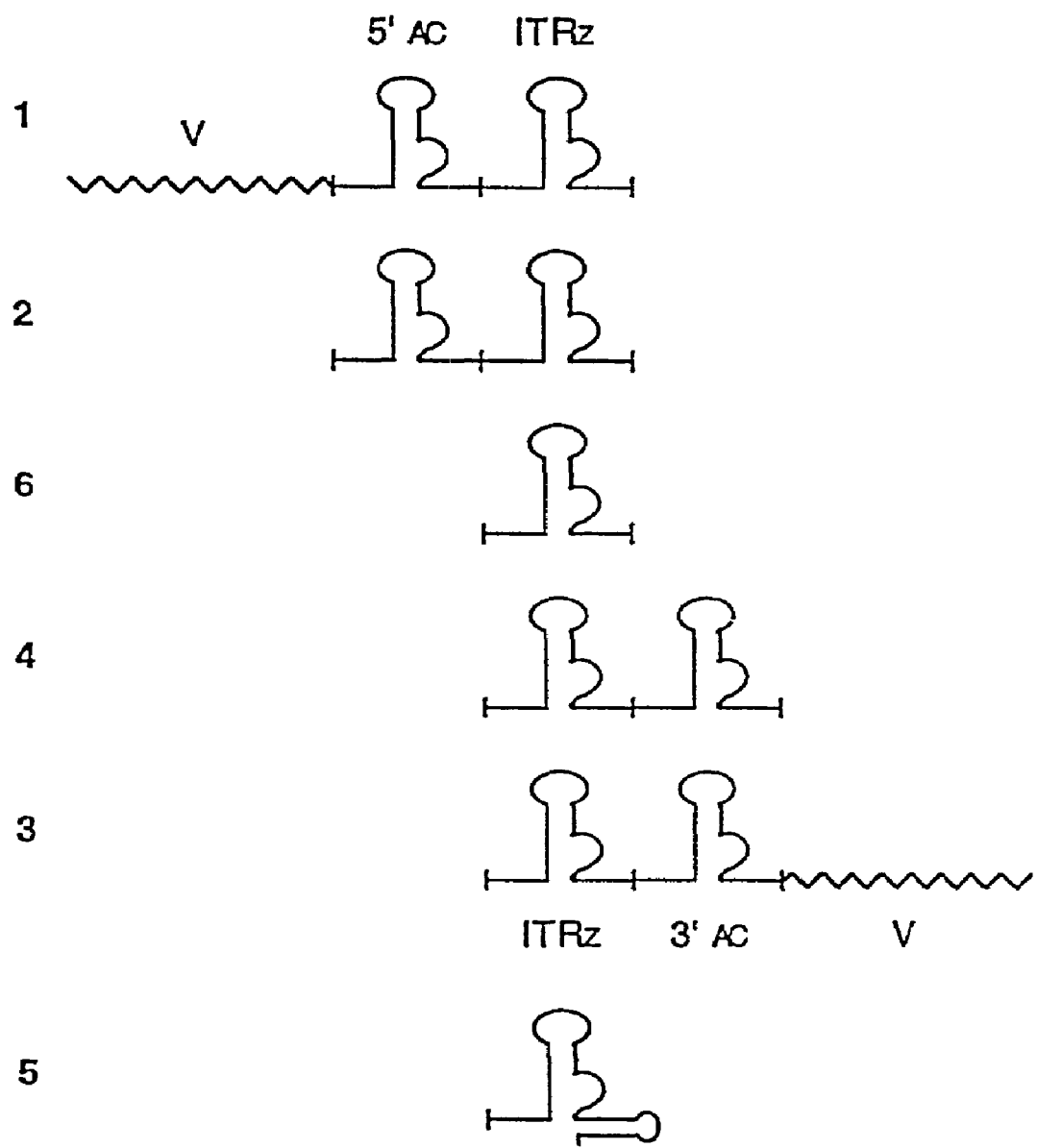

FIG. 6 Schematic diagram of various ribozyme constructs which were synthesized for testing in vitro. V denotes vector flanking sequences, 5'AC denotes the 5' autocatalytic trans-acting ribozyme which was modified so that self-liberation could not occur. ITRz denotes the internal trans-acting ribozymes also modified so that self-liberation could not occur.

Figure 7:
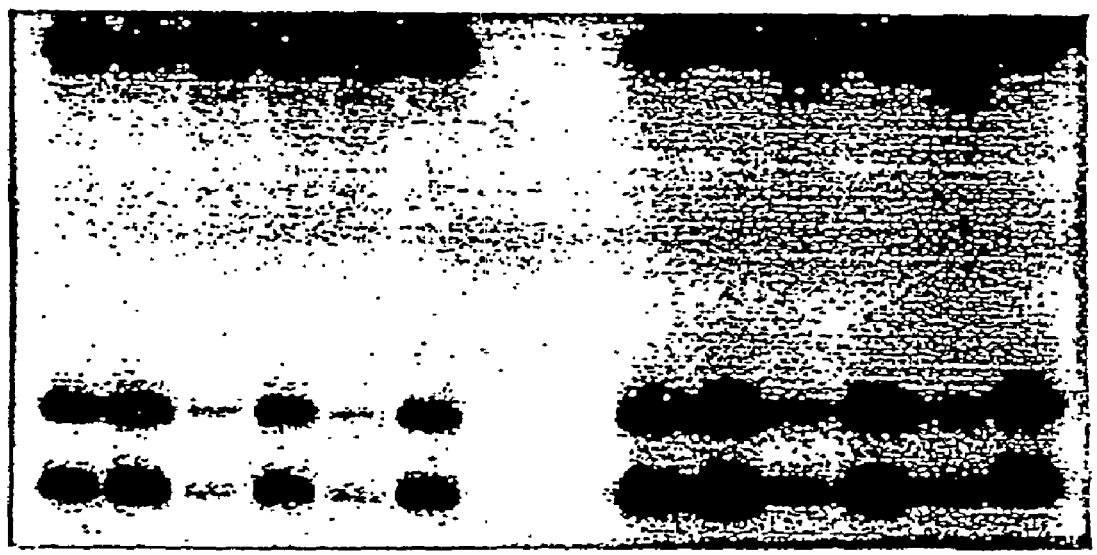

FIG. 7 In vitro Analysis of Cleavage Activity of Multi-Ribozymes. 50 nM of the each of the constructs 1 through 6 as shown in FIG. 6 were incubated for 37° C. for 0.05 or 2 hours with 50 nM of target RNA. In this example, the transacting ribozymes of the constructs were targeted to multi-catalytic proteinase component C9. Following incubation, samples were denatured and separated on a polyacrylamide gel. The upper band represents the uncleaved target RNA whereas the lower bands represent the cleaved products. The data demonstrate that a ribozyme attached at either the 5' (lane 2) or 3' (lane 4) end of a transacting ribozyme does not diminish the catalytic activity of the ribozyme.

FIG. 8 RT/PCT Analysis of TRz Expression and Self-Liberation in B2-X Clones. Cells were stably transfected with a B2-targeted PCLIP multi-ribozyme. FIG. 8A shows cytoplasmic RNA results, while FIG. 8B shows nuclear RNA results. These results demonstrate that there is a distribution of liberated transacting ribozymes between the nucleus and the cytoplasm.

Figure 9:
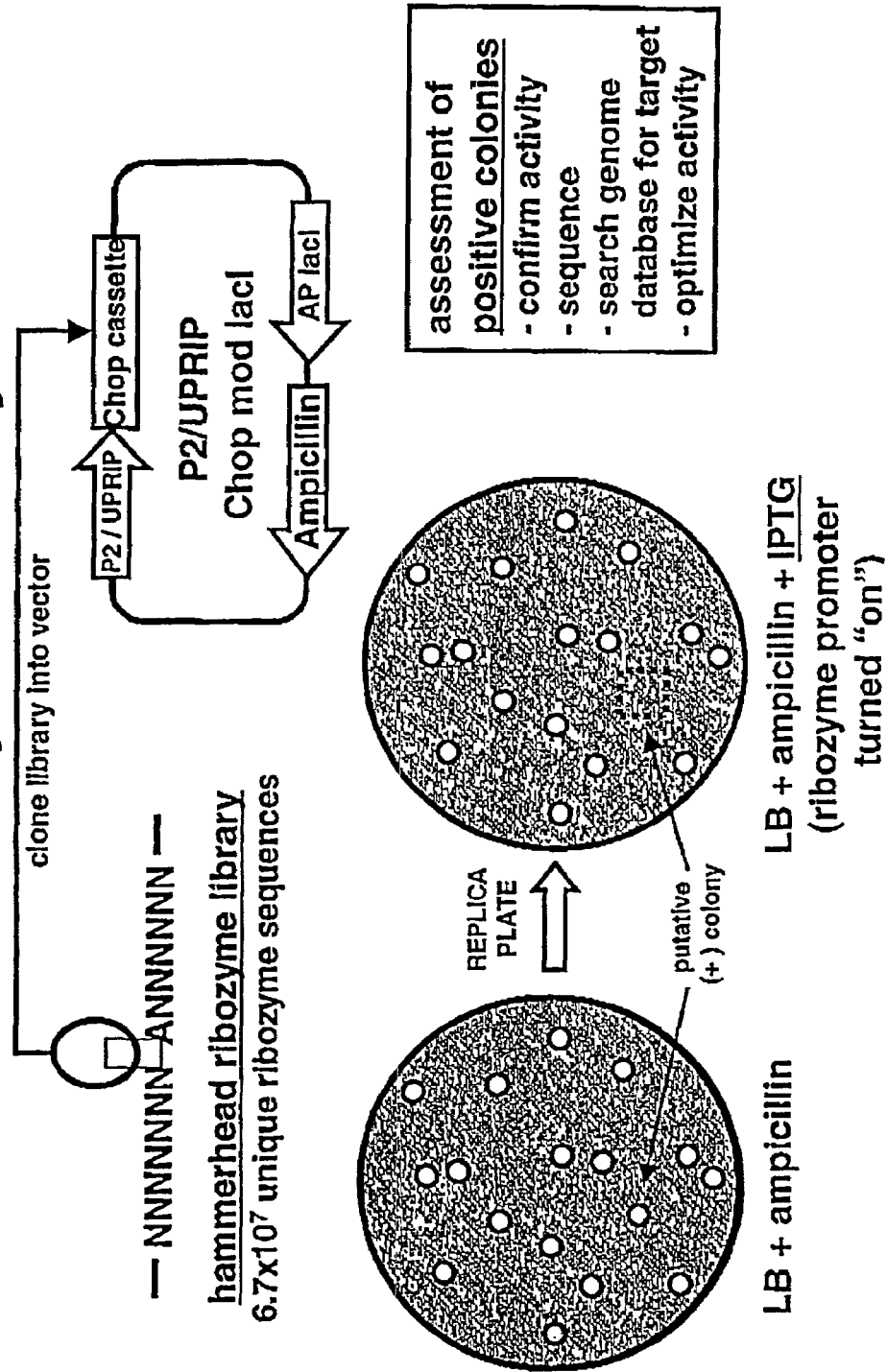

FIG. 9 Strategy of screening a ribozyme library to identify trans-acting ribozymes and/or targets.

FIG. 10 Sequence of a modified pChop cassette (UPCM2) (SEQ ID NO:52).

Figure 11:
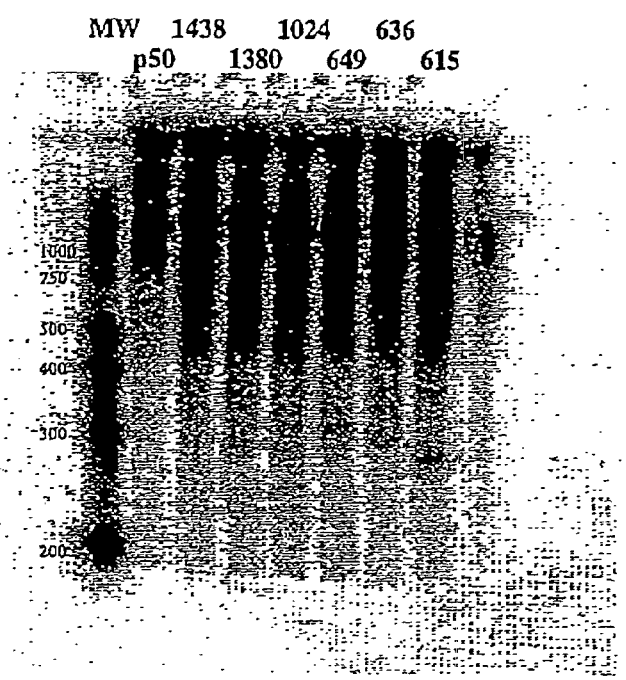

FIG. 11 In vitro substrate cleavage results of ribozymes targeted to NfκB p50 subunit.

Figure 12:
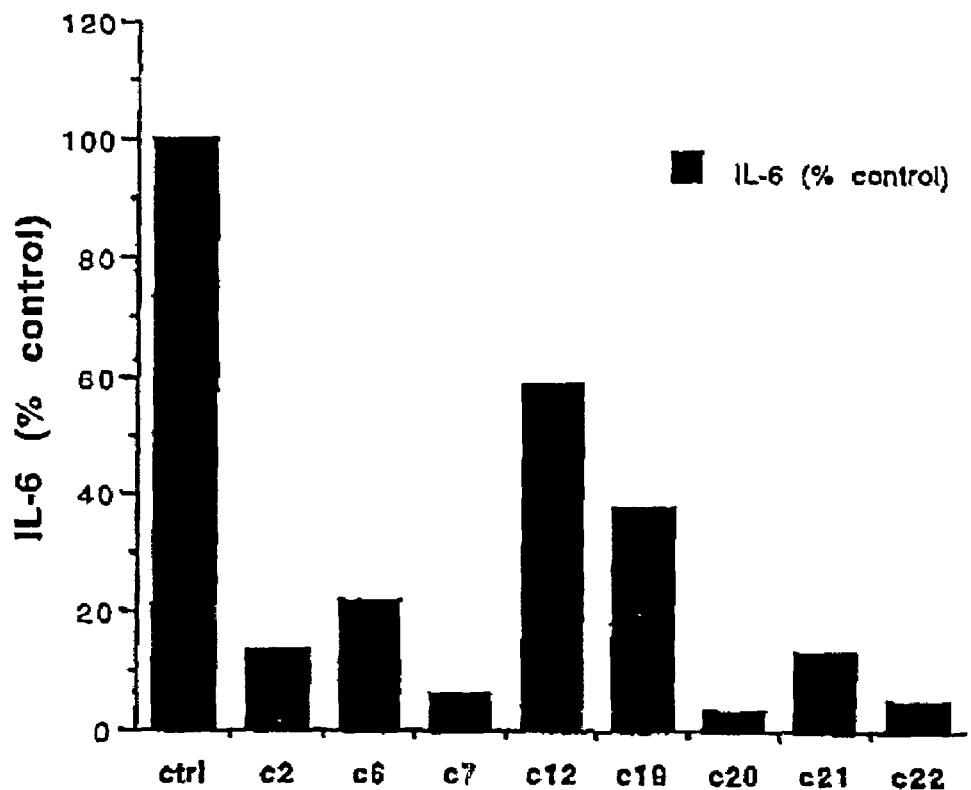

FIG. 12 Effect of Ribozyme (RZ1024, targeted to NfκB p50 subunit) on TNFα-induced IL-6 production.

5. DETAILED DESCRIPTION OF THE INVENTION

The present invention relates to multi-ribozymes and their use to target RNA in a tissue-specific or target-specific manner for the treatment of disorders and disease related to cellular proliferation, cancers and bacterial, parasitic, or viral infections. The multi-ribozymes of the present invention may be engineered to target one or more specific RNAs contained in a specific cell or tissue in the host. The multi-ribozymes of the present invention may also be engineered to target one or more specific RNAs encoded by a specific pathogen, virus or microbial agent.

The multi-ribozyme(s) of the invention contain two separable functional regions including a "catalytic core" which cleaves the target RNA or RNAs, and flanking regions which include a target RNA-specific binding site. The catalytic core contains one or more ribozymes known as trans-acting ribozymes. The flanking regions are located nearby or adjacent to the catalytic core, and contain ribozymes known as autocatalytically cleaving ribozyme sequences or autocatalytic ribozymes. A catalytic core in combination with one or more flanking region(s) as used herein is referred to as a ribozyme "cassette" or "triple ribozyme". By nucleic acid complementarity, the binding site directs the multi-ribozyme core to cleave a specific site on the target RNA molecule.

In accordance with the present invention the multi-ribozymes may comprise a 5' autocatalytically cleaving ribozyme sequence, a catalytic ribozyme comprising a target RNA-specific binding site and a 3' autocatalytically cleaving ribozyme. In accordance with the invention, the multi-ribozymes may comprise a) a trans-acting ribozyme flanked by 5' and 3' autocatalytically cleaving ribozymes or flanked by enhanced 5' and 3' autocatalytically cleaving ribozymes; b) a transacting ribozyme flanked by either a 5' or 3' autocatalytically cleaving ribozyme or flanked by an enhanced 5' or 3' autocatalytically cleaving ribozyme; or c) multiple trans-acting ribozymes flanked by one or both 5' and/or 3' autocatalytically cleaving ribozymes or flanked by enhanced 5' and/or 3' autocatalytically cleaving ribozymes.

In accordance with the present invention, the multi-ribozymes may be designed to release two or more trans-acting ribozymes. Such trans-acting ribozymes may be targeted to the same site on the same RNA, different sites on the same RNA, or different RNAs. In an additional embodiment, the ribozyme cassettes are linked in a series of one or more. In another embodiment, the linked ribozyme cassettes are non-identical.

In particular, the multi-ribozymes of the present invention are designed to have improved properties to enhance their efficacy in cleaving a target RNA. The multi-ribozymes of the present invention comprise a) one or more transacting ribozymes and b) 5' and 3' flanking autocatalytically cleaving ribozymes or only the 5' or the 3' flanking autocatalytically cleaving ribozyme. The flanking autocatalytically cleaving ribozymes act to liberate the transacting ribozyme. The autocatalytically cleaving ribozymes of the present invention may have slow cleavage activity or enhanced cleavage activity. The combination of slow cleaving autocatalytic ribozymes followed by enhanced cleaving autocatalytic ribozymes results in the distribution of transacting ribozymes between the nucleus and the cytoplasm. The use of enhanced cleaving autocatalytic ribozymes results in primarily a nuclear accumulation of the trans-acting ribozymes and the use of slow cleaving ribozymes results in primarily a cytoplasmic accumulation of the trans-acting ribozymes.

In one preferred embodiment, ribozyme cassette(s) lead to distribution of the liberated trans-acting ribozyme(s) between the nucleus and cytoplasm. In another preferred embodiment, the ribozyme cassettes lead to distribution of the liberated trans-acting ribozyme(s) with increased distributed to the nucleus.

Use of a "spacer" for linking the ribozymes together is provided by the invention. In one specific embodiment, but not by way of limitation, the ribozymes and/or ribozyme cassettes are linked together by a short "spacer" of 4-5 nucleotides.

The invention also provides multi-ribozymes containing modifications which enhance stability and protect against degradation. Examples of such modifications include those which protect against degradation by endonucleases such as modifications to the structure of the nucleotides and stabilizing hairpin loops in or near the ribozyme cassette. In one embodiment, the of the present invention one or more ribozymes are stabilized by a 3' hairpin loops.

The present invention relates to nucleic acids encoding the tissue-specific or target RNA-specific ribozymes of the present invention. In one embodiment of the invention, the nucleic acids of the present invention may comprise a tissue-specific promoter operably linked to a multi-ribozyme of the invention. In one embodiment of the invention, the nucleic acids of the present invention may comprise a tissue-specific promoter upstream from a sequence encoding a 5' autocatalytically cleaving ribozyme, a catalytic ribozyme comprising a target RNA-specific binding site and a 3' autocatalytically cleaving ribozyme sequence. In another embodiment of the invention, the nucleic acids may comprise a tissue-specific promoter upstream from a sequence encoding a 5' autocatalytically cleaving ribozyme, an internal targeted catalytic core containing two or more target RNA-specific trans-acting ribozymes and a 3' autocatalytically cleaving ribozyme sequence.

In a preferred embodiment, the nucleic acid encodes the modified 5' and/or 3' autocatalytically cleaving ribozymes of the present invention which have enhanced cleaving activity which results in the enhanced and more effective release of the internal catalytic ribozyme(s).

The present invention further relates to the use of a wide variety of vehicles to deliver the multi-ribozymes to a target, including biologic vehicles such as virions and viral vectors to package and deliver the DNA encoding the multi-ribozymes; non-viral expression vectors and non-biologic (abiologic) vehicles, including liposomes and liposome-DNA and lipid-DNA complexes to deliver and target the DNA encoding the multi-ribozymes to the host.

In another embodiment, the invention relates to nucleic acids which encode multi-ribozymes which are targeted by their delivery vehicle.

In accordance with the invention, the host to which the multiple-ribozymes are delivered may be cells in culture, tissues in culture, plants, animal models, animals, mammals or humans.

The present invention relates to pharmaceutical compositions comprising the multi-ribozymes of the present invention and their delivery vehicles. The multi-ribozymes of the present invention may be engineered for the treatment of a wide variety of disorders and diseases related to expression of a particular gene or genes, cellular overproliferation, hereditary disorders, cancers, tumors, viral infections, bacterial or parasitic infections.

In another embodiment of the present invention, the multi-ribozymes of the present invention may also be used for in vitro screening purposes, e.g. to identify a gene product involved in cellular overproliferation or to identify a gene product critical for the life cycle of a viral or microbe.

5.1. Ribozymes

The present invention provides tissue-specific and target RNA-specific ribozymes. These ribozymes can be used to destroy tissue-specific neoplasms, cancers, or proliferative disorders and to treat viral, bacterial or parasitic infections, among other uses. The multi-ribozymes of the present invention comprise one or more ribozymes or ribozyme cassettes.

In accordance with the present invention, the multi-ribozyme may consist of one or more ribozyme cassettes. Each cassette in turn may consist of a catalytic core and one or more flanking sequences. In one embodiment, the ribozyme cassette may consist of a 5' autocatalytically cleaving ribozyme sequence, a catalytic ribozyme comprising a target RNA-specific binding site and a 3' autocatalytically cleaving ribozyme. In another embodiment, the ribozyme cassette may consist of a 5' autocatalytically cleaving ribozyme sequence, a catalytic core ribozyme comprising a trans-acting ribozyme and a 3' autocatalytically cleaving ribozyme.

In a preferred embodiment, the multi-ribozyme comprises an enhanced 5' and 3' autocatalytically cleaving ribozyme sequence. In another preferred embodiment of the invention, the multi-ribozyme comprises the ribozyme cassette as shown in FIG. 2. In another preferred embodiment, the multi-ribozyme comprises the ribozyme cassette as shown in FIG. 3. In a most preferred embodiment, the multi-ribozyme comprises the ribozyme cassette as shown in FIG. 4. In another embodiment, the ribozymes are in a cassette. In yet another embodiment, the multi-ribozymes contain two, three, four or more internal trans-acting ribozymes. In a preferred embodiment, the multi-ribozymes of the present invention include, but are no limited to triple ribozyme cassettes (as described herein, such as a cassette composed of one or more trans-acting ribozymes linked to a 3' and 5' flanking autocatalytically cleaving ribozymes). In another embodiment, multi-ribozymes include but are not limited to one or more triple ribozyme cassettes linked together. In an additional embodiment, the multi-ribozyme comprises a series of one or more ribozyme cassettes containing one or more internal trans-acting ribozymes or any combination thereof. In one specific embodiment, the multi-ribozyme comprises two ribozyme cassettes, each with two trans-acting ribozymes in the catalytic core (Double ITRz) as shown in FIG. 4.

The invention provides ribozymes that have the unique characteristic of being both target RNA-specific in their catalytic action, and subject to tissue-specific expression. Examples of the enhanced 5' and 3' autocatalytically cleaving ribozymes that are expressed with the catalytic ribozyme of the invention are also shown in FIG. 3. Other examples of nucleotides encoding 5' and 3' autocatalytically cleaving ribozymes and vectors for the multi-ribozymes of the present invention are described in WO 97/17433, incorporated herein by reference in its entirety. As further described below, these autocatalytically cleaving ribozymes are important for the expression of the catalytic ribozyme, because they cleave off the ribozyme transcript as soon as they are transcribed to produce a catalytic ribozyme having minimal extraneous 5' or 3' sequences. Further, the enhanced autocatalytically cleaving ribozymes are important for the expression of the trans-acting catalytic ribozyme, influencing the cellular distribution of the transacting ribozymes and since they cleave the ribozyme transcript as soon as they are transcribed to produce a catalytic trans-acting ribozyme having minimal extraneous 5' or 3' sequences.

Thus, the target-specific binding site and the catalytic sequence that comprise the catalytic ribozyme are in the correct configuration to bind and cleave the target RNA. The extraneous sequences in the exemplified construct are the result of the cloning procedure. It is understood that with the selection of an alternative cloning scheme some or all of these extraneous nucleotides can be eliminated.

The Applicants have demonstrated that liberating the internal ribozyme is five to ten fold more active with the cleaving auto-catalytic ribozymes than when the same ribozyme is embedded within other flanking sequences. Applicants have further demonstrated that liberation of internal trans-acting ribozymes from a combination of slow cleaving and enhanced cleaving auto-catalytic ribozymes results in a distribution of the trans-acting ribozyme between the nucleus and cytoplasm.

5.1.1. Ribozyme-encoding Nucleic Acids

The invention also provides nucleic acids which encode the ribozymes of the invention. The invention provides nucleic acids which encode ribozyme(s) which are tissue-specific or target RNA-specific. The invention also provides nucleic acids which encode ribozyme(s) operably linked to a tissue-specific, or target-specific (i.e., pathogen-specific) promoter. These nucleic acids can be used to express the ribozymes of the invention at the selected site. For example, the site can be tissue-specific in the case of treating tissue-specific cancers or disease, or it can be target-specific in the case of ribozymes that prevent replication of infectious agents to treat infection (e.g. hepatitis, herpes, malaria, tuberculosis, etc.).

In several embodiments, nucleic acids of the invention encode a catalytic multi-ribozyme that contains two separable functional regions including a) a catalytic core sequence which cleaves the target RNA, and b) flanking regions which include cis-acting autocatalytically cleaving ribozyme(s). The length of flanking sequences have implications not only for specificity, but also for the cleavage efficiency of the individual ribozyme molecules. In the present catalytic ribozyme, the flanking sequences are highly specific for the target RNA, yet allow ready dissociation from the target RNA once cleavage occurs. This permits cycling of the ribozyme (with an expected Kcal of about 1 cleavage per minute) and reduces the amount of ribozyme required to be effective. A range of binding/dissociation values from 16-21 Kcal is expected to be effective.

In accordance with the invention, a pathogen-specific promoter or tissue-specific promoter may be operably linked to any sequence encoding a multi-ribozyme or expression cassette of the invention. In several embodiment, the nucleic acids of the invention comprise a tissue-specific promoter operably linked to a sequence encoding a multi-ribozyme. The tissue-specific promoter in the ribozyme-producing construct results in tissue-specific expression of the ribozyme(s) in tissue(s) that actively transcribe RNA from the selected promoter. Thus, only the target RNA in tissue that utilize the promoter will be cleaved by the ribozyme(s).

In other embodiments, the nucleic acids and expression cassettes of the invention comprise a pathogen-specific promoter operably linked to a sequence encoding a multi-ribozyme. For example, a pathogen-specific promoter or tissue-specific promoter may be operably linked to a nucleotide sequence encoding a) a catalytic core ribozyme sequence which cleaves the target RNA of the pathogen, and b) 3' and/or 5' flanking regions which include cis-acting autocatalytically cleaving ribozyme(s).

In accordance with the present invention, a multi-ribozyme may be engineered to express two or more ribozyme cassettes containing trans-acting ribozymes which act on the same or different targets. In an additional embodiment, the invention provides for nucleic acid that encode one or more ribozyme cassettes each cassette containing a) a 5' autocatalytically cleaving ribozyme sequence and/or a 3' autocatalytically cleaving ribozyme sequence; and b) one or more catalytic ribozymes comprising one or more target RNA-specific trans-acting ribozymes. In a preferred embodiment, the invention provides nucleic acids which encode multi-ribozymes with multiple trans-acting ribozymes, resulting in the more effective and efficient cleavage of target RNA.

In other embodiments, the invention provides nucleic acids and expression cassettes which encode multi-ribozymes with altered cleavage sites, so that the 5' and/or 3' autocatalytically cleaving ribozymes have enhanced activity, resulting in the more effective and efficient release of the internal trans-acting ribozymes. Thus, the expression cassettes may also be engineered to express two or more multi-ribozymes containing 5' and/or 3' autocatalytically cleaving ribozymes with either slow or enhanced cleavage activities. In one embodiment, expression cassette encodes a combination of autocatalytically cleaving ribozymes with slow and enhanced cleavage activities, resulting in a distribution of liberated trans-acting ribozymes between the nucleus and cytoplasm of a eukaryotic cell. In another embodiment, the expression cassette encodes enhanced autocatalytically cleaving ribozymes resulting in an increase accumulation of the liberated trans-acting ribozymes in the nucleus.

The nucleic acid, wherein at least one triple ribozyme is targeted to the rpoA transcript of the pathogen is provided. The nucleic acid, wherein at least one triple ribozyme is targeted to the secA transcript of the pathogen is provided. The nucleic acid, wherein at least one triple ribozyme is directed to the dnaG transcript of the pathogen is provided. The nucleic acid, wherein at least one triple ribozyme is directed to the ftsZ transcript of the pathogen is provided. A ribozyme-encoding nucleic acid can encode all or some of the above triple ribozymes. The triple ribozymes and ribozyme cassettes can all be under the control of a single promoter.

Many examples of the nucleic acid encoding the trans-acting ribozyme of the triple ribozyme are described herein and in the Sequence Listing (e.g., SEQ ID NO:8-17, 43-48) and Examples Section herein.

5.1.2 Promoter Selection

Promoter selection is accomplished using techniques that are available in the art. As used herein, regulatory elements include but are not limited to, inducible and non-inducible promoters, enhancers, operators and other elements known to those skilled in the art that drive and regulate expression. Specifically, the invention provides inducible promoters which have increased transcriptional control and high expression levels. The promoter can be a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of ribozymes in the targeted microbe. For example, a method is described in the Examples that permits the selection of both controlled and uncontrolled promoters, as well as consensus promoters that can be design for application in the present multi-ribozyme.

Promoters specific for the target (e.g., a specific pathogen, genus, etc.) in question can be selected by screening genomic sequences for the ability to activate a promoterless reporter gene. The promoterless reporter gene is based on the strategy developed for use with plasmid pMC1871 (Casadaban et al., 1983, Meth. Enzymol. 100:293). For non-viral pathogens, plasmid capable of stable replication and maintenance in the microorganism understudy is modified by standard molecular biology techniques to carry the coding region of a reporter gene (Sambrook et al., Molecular Cloning: A Laboratory Manual, 2nd Ed., Cold Spring Harbor Laboratory, Cold Spring Harbor, N.Y., latest edition). The reporter gene can be any of a number of standard reporter genes including but not limited to the lacZ gene of *E. coli*, which codes for β-galactosidase. Total genomic DNA is isolated from cells of the pathogen, cleaved with restriction endonucleases to yield fragments of a few hundred base pairs on average. These fragments are then ligated into a unique restriction endonuclease cleavage site at the 5' end of the reporter gene coding region, creating a library of plasmids. The library is then transformed into the pathogen by standard techniques and the resulting transformants are screened for expression of the reporter gene. In the case of lacZ, the transformants can be plated onto medium containing the chromogenic galactosidase substrate X-Gal (5-bromo-4-chloro-3-indolyl-D-galactoside). Transformants that contain a plasmid with an insert carrying a promoter will express β-galactosidase and will turn blue on X-Gal plates. The intensity of the blue color is relative to the level of expression; promoters of different strength can be selected based on the intensity of the blue color.

The above-described screening procedure can be modified to identify regulated promoters. For example, promoters that are regulated by carbon source availability can be screened on plates that contain different carbon sources. Other modifications are possible and will depend, in part, on the organism in question. To test for species-specificity, the identified promoters are transferred to promoterless reporter plasmids capable of replication and maintenance in a different organism. Truly species-specific or pathogen-specific promoters will not activate the expression of the reporter gene in any other species. Obvious modifications can be used to identify and test artificial promoters composed of synthetic oligonucleotides inserted into the promoterless reporter plasmid.

In one embodiment, the nucleic acids of the invention comprise a tissue-specific promoter operably linked to a sequence encoding a multi-ribozyme of the invention.

The tissue-specific promoter in the ribozyme-producing construct results in tissue-specific expression of the ribozyme in tissue(s) that actively transcribe RNA from the selected promoter. Thus, only the target RNA in tissue that utilize the promoter will be cleaved by the ribozyme. Tissue-specific promoters can be used in the present nucleic acid constructs. Examples of these promoters include the binding sites (sequences) for probasin-promoter, a promoter-specific for prostate epithelium prostate-specific antigen (prostate), keratin k4, k13, k7 (epidermal sabaceus glands), albumin (liver), fatty acid binding protein (ilium), whey acidic protein (breast), lactalbumin, smooth muscle actin (smooth muscle), etc.

The pathogen-specific promoter in the ribozyme-producing construct results in pathogen-specific expression of the ribozyme in pathogens or microbes that actively transcribe RNA from the selected promoter. Thus, only the target RNA in pathogens that utilize the promoter will be cleaved by the ribozyme.

It will also be clear that tissue-specific or target-specific promoters not yet identified can be used to target expression of the present ribozymes to the selected tissue(s). Once a target-specific or tissue-specific promoter is identified its binding sequence can be routinely determined by routine methods such as sequence analysis. The promoter is defined by deletion analysis, mutagenesis, footprinting, gel shifts and transfection analyses (Sambrook et al., supra).

5.2. Expression of the Multi-Ribozymes in Procaryotic and Eucaryotic Expression Systems The present invention encompasses expression systems, both eucaryotic and procaryotic expression vectors, which may be used to express the multi-ribozymes of the present invention.

The invention encompasses the DNA expression vectors and/or viral vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences in the host cell. As used herein, regulatory elements include but are not limited to, inducible and non-inducible promoters, enhancers, operators and other elements known to those skilled in the art that drive and regulate expression.

The DNA expression vectors and viral vectors containing the nucleic acids encoding the multi-ribozymes of the present invention may be produced by recombinant DNA technology using techniques well known in the art. Thus, methods for preparing the expression vectors and viral vectors of the invention by expressing nucleic acid containing multi-ribozyme sequences are described herein. Methods which are well known to those skilled in the art can be used to construct expression vectors containing epitope gene product coding sequences and appropriate transcriptional and translational control signals. These methods include, for example, in vitro recombinant DNA techniques, synthetic techniques, and in vivo genetic recombination. See, for example, the techniques described in Sambrook et al., supra. Alternatively, RNA capable of encoding glycoprotein epitope gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety. Gene expression may be regulated by a variety of methods known in the art including but not limited to those presented in Mizuno, T. et al., 1984, Proc. Natl. Acad Sci USA. 81(7):1966070.

5.2.1 Eucaryotic and Procaryotic Expression Vectors

The present invention encompasses expression systems, both eucaryotic and procaryotic expression vectors, which may be used to express the multi-ribozymes. A variety of host-expression vector systems may be utilized to express the selected multi-ribozyme of the invention. Such host-expression systems represent vehicles by which the sequences encoding the multiple ribozymes may be introduced into cells and tissues both in vivo and in vitro but also represent cells which may, when transformed or transfected with the appropriate nucleotide coding sequences, express the multi-ribozymes of the invention. These include but are not limited to microorganisms such as bacteria (e.g., *E. coli, B. subtilis*) transformed with recombinant bacteriophage DNA, plasmid DNA or cosmid DNA expression vectors containing selected multi-ribozyme coding sequences; yeast (e.g., *Saccharomyces, Pichia*) transformed with recombinant yeast expression vectors containing the selected multi-ribozyme coding sequences; insect cell systems infected with recombinant virus expression vectors (e.g., baculovirus) containing the selected multi-ribozyme coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing selected multi-ribozyme coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

5.3 Delivery and Expression Systems

Until the discoveries of present invention, the therapeutic use of ribozymes in eukaryotes was limited because a convenient and efficient delivery system has not been available. A key to the present invention is the strategies used to deliver the ribozymes to the targeted microorganism. Two separate classes of delivery systems can be manufactured, one biologic in nature and the other abiologic.

The key features of the present invention are the combination of ribozymes with viral delivery and assembly of the virions using a unique combination of plasmid features.

5.3.1 Abiologic Delivery Vehicles

Abiologic delivery of the ribozymes is accomplished by a variety of methods, including packaging plasmid DNA carrying the nucleic acids that code for the ribozyme(s) into liposomes or by complexing the plasmid DNA carrying the nucleic acids that code for the ribozyme(s) with lipids or liposomes to form DNA-lipid or DNA-liposome complexes. The liposome is be composed of cationic and neutral lipids commonly used to transfect cells in vitro. The cationic lipids complex with the plasmid DNA and form liposomes.

A liposome is provided, comprising a nucleic acid encoding a multi-ribozyme of the invention. A liposome is provided, comprising a nucleic acid comprising a tissue-specific promoter or target-RNA specific pathogen-specific promoter upstream from a sequence encoding multi-ribozyme of the invention. For example, a liposome is provided, comprising a nucleic acid comprising a pathogen-specific promoter upstream from a sequence encoding a triple ribozyme comprising a) a 5' autocatalytically cleaving ribozyme sequence, b) a catalytic ribozyme comprising a target RNA-specific binding site and c) a 3' autocatalytically cleaving ribozyme sequence. A liposome is provided, comprising a nucleic acid comprising a tissue-specific promoter or target-RNA specific pathogen-specific promoter upstream from a sequence encoding a) a 5' autocatalytically cleaving ribozyme sequence and/or a 3' autocatalytically cleaving ribozyme; and b) catalytic ribozyme(s) comprising one or more target RNA-specific trans-acting ribozymes. The liposome of the invention, wherein the nucleic acid encodes more than one triple ribozyme or ribozyme cassette is provided. The liposome can comprise any ribozyme-encoding nucleic acid, particularly those described herein.

The liposomal delivery systems of the invention can be used to deliver a nucleic acid comprising a pathogen-specific promoter upstream from a sequence encoding a triple ribozyme comprising a) a 5' autocatalytically cleaving ribozyme sequence, b) a catalytic ribozyme comprising one or more target RNA-specific binding site and c) a 3' autocatalytically cleaving ribozyme sequence. The liposomal delivery systems of the invention can be used to deliver a nucleic acid comprising a pathogen-specific promoter upstream from a sequence encoding any of the multi-ribozymes described herein. The multi-ribozyme that is administered to a subject can further comprise a liposome.

Cationic and neutral liposomes are contemplated by this invention. Cationic liposomes can be complexed with the a negatively-charged biologically active molecule (e.g., DNA) by mixing these components and allowing them to charge-associate. Cationic liposomes are particularly useful when the biologically active molecule is a nucleic acid because of the nucleic acids negative charge. Examples of cationic liposomes include lipofectin, lipofectamine, lipofectace and DOTAP (Hawley-Nelson et al., 1992, Focus 15(3):73-83; Felgner et al., 1992, Proc. Natl. Acad. Sci. U.S.A. 84:7413; Stewart et al., 1992, Human Gene Therapy 3:267-275). Procedures for forming cationic liposomes encasing substances are standard in the art (Nicolau et al., 1987, Methods Enzymol. 149:157) and can readily be utilized herein by one of ordinary skill in the art to encase the complex of this invention.

In yet another embodiment of the present invention, the plasmid DNA carrying the gene(s) or nucleic acids that codes for the ribozymes of the invention are complexed with liposomes using an improved method to achieve increased systemic delivery and gene expression (Templeton et al., 1997, Nature Biotechnology 15: 647-652). In accordance with the present invention, an improved formulation of cationic lipids which greatly increase the efficiency of DNA delivery to host cells, with extended half-life in vivo and procedures to target specific tissues in vivo. For example, but not by limitation, peptides and proteins may be engineered to the outer lipid bilayer, such as liver specific proteins, leads to substantially enhanced delivery to the liver etc.

In one embodiment of the present invention, systemic delivery and in vivo and ex vivo gene expression is optimized using commercially available cationic lipids, e.g., dimethyldioctadeclammonium bromide (DDAB); a biodegradable lipid 1,2-bis(oleoyloxy)-3-(trimethylammonio) propane (DOTAP); these liposomes may be mixed with a neutral lipid, e.g., L-α dioleoyl phosphatidylethanolamine (DOPE) or cholesterol (Chol), two commonly used neutral lipids for systemic delivery. DNA:liposome ratios may be optimized using the methods used by those of skill in the art (see e.g., Templeton et al., supra).

In yet another embodiment of the present invention, the plasmid DNA carrying the genes or nucleic acids encoding the ribozymes of the invention may be delivered via polycations, molecules which carry multiple positive charges and are used to achieve gene transfer in vivo and ex vivo. Polycations, such as polyethilenimine, may be used to achieve successful gene transfer in vivo and ex vivo (see e.g., Boletta et al., 1996, J. Am. Soc. Nephrol. 7:1728).

The liposomes may be incorporated into a topical ointment for application or delivered in other forms, such as a solution which can be injected into an abscess or delivered systemically.

Plasmid DNA coding for the ribozymes is used rather than preformed ribozymes for the following reasons. Plasmid DNA allows the targeted cells to produce the ribozyme and, thus, results in a higher delivered dose to the cell than can be expected by delivery of ribozyme RNA via liposome. The DNA also provides specificity of action based on target sequence specificity. The liposomes deliver their DNA to any cell in the area of administration, including cells of the host. The promoter driving the transcription of the ribozyme is specific for the targeted microorganism and, thus, will be inactive in other cell types. Therefore, liposomal delivery of DNA coding for the ribozyme provides amplification and specificity.

5.3.2 Biologic Delivery Vehicles

Not all microorganisms are expected to take up DNA delivered by liposome. Consequently, a biologic delivery system is also required. The biologic delivery vehicle of the multi-ribozyme or ribozymes of the invention takes advantage of the fact that generalized transducing particles completely lack DNA originating from the viral vector. Instead such particles only contain sequences of host origin. Consequently, the invention uses a biologic assembly of viral head proteins (packaging elements for the antimicrobial therapeutic) around the nucleic acid containing the necessary genetic elements that will insure the desired level of expression of the ribozyme(s).

5.3.2.1 Expression of Multi-Ribozymes in Recombinant Viral Vectors

In another embodiment of the present invention, either a live recombinant viral vaccine or an inactivated recombinant viral vector expressing the selected multi-ribozyme can be engineered. In this regard, a variety of viruses may be genetically engineered to express the selected multi-ribozymes. For gene therapy purposes, it may be required that the recombinant viruses display attenuation characteristics. Current live recombinant virus candidates for use in humans are either cold adapted, temperature sensitive, or attenuated. The introduction of appropriate mutations (e.g., deletions) into the templates used for transfection may provide the novel viruses with attenuation characteristics. For example, specific multiple missense mutations that are associated with temperature sensitivity or cold adaptation can be made into deletion mutations and/or multiple mutations can be introduced into individual viral genes. These mutants should be more stable than the cold or temperature sensitive mutants containing single point mutations and reversion frequencies should be extremely low. Alternatively, recombinant viruses with "suicide" characteristics may be constructed. Such viruses go through only one or a few rounds of replication in the host.

In accordance with the present invention, a wide variety of viruses and viral vectors may be used to deliver the nucleotide sequences encoding the multi-ribozymes of the present invention, a few examples of which are described below.

Retroviral vectors are commonly used to deliver genes to host cells both in vivo and ex vivo. Retroviral vectors are extremely efficient gene delivery vehicles that cause no detectable harm as they enter the cells. The retroviral nucleic acid may integrate into host chromosomal DNA allowing for long-term persistence and stable transmission to future progeny, such a vector would be useful for the delivery of a multi-ribozyme used to target a cellular gene product involved in a chronic or hereditary disorder or to target a viral gene or a microbial gene or a parasitic gene involved in a chronic or persistent infection. An example of an appropriate retroviral vector are, lentiviruses which have the advantage of infecting and transducing non-dividing cells. In such an embodiment, a lentiviral vector encoding a packagable RNA vector genome and operably linked to a promoter in which all the functional retroviral auxiliary genes are absent, is used to transfer the DNA encoding the multi-ribozyme of the present invention. Examples of such vectors are described in WO 98/17815, WO 98/17816 and WO 98/17817, each of which is incorporated herein by reference in their entirety.

In yet another embodiment, non-integrating viral vectors which infect and transduce non-dividing cells, such as adenoviral vectors may be used to deliver the multi-ribozymes of the present invention. Adenoviral vectors have several advantages because it avoids risks associated with permanently altering the host cell genome or of promoting insertional mutagenesis. Adenoviruses are one of the best developed non-integrating viral vectors and can be used to transfer expression cassettes of up to 75 kb. Recombinant adenoviruses can be produced at very high titers is highly infectious and efficiently transfer genes to a wide variety of non-replicating and replicating cells and is ideal for in vivo mammalian gene transfer.

Adenovirus-based vectors are relatively safe and can be manipulated to encode the desired multi-ribozyme and at the same time to be inactivated in terms of their ability to replicate in a normal lytic viral life cycle. Adenovirus has a natural tropism for airway epithelia. Therefore, adenovirus-based vectors are particularly preferred for respiratory gene therapy applications. In a particular embodiment, the adenovirus-based gene therapy vector comprises an adenovirus 2 serotype genome in which the Ela and the Elb regions of the genome, which are involved in early stages of viral replication have been deleted and replaced by nucleotide sequences of interest. In a further embodiment, the adenovirus-based gene therapy vector contains only the essential open reading frame (ORF3 or ORF6 of adenoviral early region 4 (E4) and is deleted of all other E4 open reading frames, or may additionally contain deletions in the E3 regions (see e.g. U.S. Pat. No. 5,670,488, incorporated herein by reference in its entirety). In another embodiment, the adenovirus-based therapy vector used may be a pseudo-adenovirus (PAV), which contain no harmful viral genes and a theoretical capacity for foreign material of nearly 36 kb.

In another embodiment, adeno-associated virus (AAV) systems may be used to deliver the multiple ribozymes of the present invention. AAV has a wide host range and AAV vectors have currently have been designed which do not require helper virus. Examples of such AAV vectors are described in WO 97/17458.

Vaccinia viral vectors may be used in accordance with the present invention, as large fragments of DNA are easily cloned into its genome and recombinant attenuated vaccinia variants have been described (Meyer, et al., 1991, J. Gen. Virol. 72:1031-1038). Orthomyxoviruses, including influenza; Paramyxoviruses, including respiratory syncytial virus and Sendai virus; and Rhabdoviruses may be engineered to express mutations which result in attenuated phenotypes (see U.S. Pat. No. 5,578,473, issued Nov. 26, 1996 incorporated herein by reference in its entirety). These viral genomes may also be engineered to express foreign nucleotide sequences, such as the selected multi-ribozymes of the present invention (see U.S. Pat. No. 5,166,057, issued Nov. 24, 1992 incorporated herein by reference in its entirety). Reverse genetic techniques can be applied to manipulate negative and positive strand RNA viral genomes to introduce mutations which result in attenuated phenotypes, as demonstrated in influenza virus, Herpes Simplex virus, cytomegalovirus and Epstein-Barr virus, Sindbis virus and poliovirus (see Palese et al., 1996, Proc. Natl. Acad. Sci. USA 93:11354-11358). These techniques may also be utilized to introduce foreign DNA, i.e., the selected multi-ribozymes, to create recombinant viral vectors to be used in accordance with the present invention. In addition, attenuated adenoviruses and retroviruses may be engineered to express the multi-ribozymes. Therefore, a wide variety of viruses may be engineered to design the multi-ribozyme delivery vehicles of the present invention.

The viral vectors of the present invention may be engineered to express the multi-ribozymes in a tissue-specific manner. For example, the promoter of the carcinoembryonic antigen (LEA) is expressed in a proportion of breast, lung and colorectal cancers, but rarely in healthy tissues. In order to target a hepatoma, the α-fetoprotein (AFP) promoter whose activity is restricted to malignant cells. Proliferating cells can be targeted with a flt-1 promoter, which has been shown to allow preferential targeting of proliferating endothelial cells. See Miller et al., 1997, Human Gene Therapy 8:803-815.

The virion of the present invention can also be any bacteriophage which specifically infects a bacterial pathogen of the present invention as well as any virus which can be specifically targeted to infect the pathogen of the present invention (Soothill, J. S., 1992, J. Med. Microbiol. 37:358-261).

For example, the bacteriophage can include, but is not limited to, those specific for bacterial cells of the following genera: *Bacillus, Campylobacter, Corynebacterium, Enterobacter, Enterococcus, Escherichia, Klebsiella, Mycobacterium, Pseudomonas, Salmonella, Shigella, Staphylococcus, Streptococcus, Vibrio, Streptomyces, Yersinia* and the like (see e.g., the American Type Culture Collection Catalogue of Bacteria and Bacteriophages, latest edition, Rockville, Md.), as well as any other bacteriophages now known or later identified to specifically infect a bacterial pathogen of this invention.

In the virions of the present invention, the non-viral DNA can encode any ribozyme of the invention. In the virions of the non-viral DNA can comprises a pathogen-specific promoter upstream from a sequence encoding one or more ribozyme cassettes containing one or more trans-acting ribozymes within the catalytic core(s). In one example the multi-ribozyme may comprise a) a. 5' autocatalytically cleaving ribozyme sequence, b) a catalytic ribozyme comprising two target RNA-specific binding site sequences and c) a 3' autocatalytically cleaving ribozyme sequence.

The virions of the present invention within the non-phage DNA which encodes more than one triple ribozyme is also provided. There are several options for constructing the multi-ribozyme encoding sequences: 1) ribozymes directed to different targets in the same pathogen; 2) multiple copies of the same ribozyme; and 3) multiple ribozymes directed to multiple targets. These may be combined in various ways, e.g., multiple copies of DNA encoding 4 different ribozymes in a single construct under one promoter. The promoter can have the chosen level of specificity as described herein.

The virion can contain a nucleic acid encoding at least two different ribozyme cassettes. The virion can contain a nucleic acid encoding more than one copy of a ribozyme cassette. The virion can comprise any ribozyme-encoding nucleic acid, particularly those described herein.

The nucleic acid delivered by the virion or liposome can encode more than one ribozyme cassette. The nucleic acid can encode at least one or more different ribozyme cassettes. The nucleic acid can encode more than one copy of the same ribozyme cassette. The nucleic acid can encode a cassette in which the cassette is a triple ribozyme. Each ribozyme cassette can contain one or more trans-acting ribozymes. Trans-acting ribozymes can be directed to the same or different targets. The nucleic acid can encode combinations of different ribozymes, some or all of which may be encoded in more than one copy. Additionally, the ribozymes may be linked by a short spacer. The ribozymes of the invention can be stabilized by a hairpin loop.

This delivery system consists of a DNA plasmid carrying the gene(s) coding for the ribozyme(s) packaged into viral particles. Specificity is conferred by the promoter driving transcription of the ribozymes and by the host specificity of the viral vehicle. The invention provides examples of the system using bacteriophage lambda virions to package DNA carrying ribozymes directed against *Escherichia coli*. Similar strategies are used to generate Multi-ribozyme capable of delivering ribozymes directed against other microorganisms. The virions used to package the DNA can be species specific, such as the virion derived from the bacteriophage lambda coat, or they can possess a broader host range, such as virion derived from bacteriophage P1. Broad host-range viruses facilitate production of the anti-microbial agents without the loss of species specificity because species-specific promoters are used to direct the transcription of the ribozymes which are directed against species specific targeted RNA sequences.

One example of construction the present multi-ribozyme invention entails the use of a plasmid carrying the ribozyme gene(s), a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of eplication on the plasmid and all of the structural components needed to form mature virions; however, the lysogen is not able to replicate and package its own DNA into the virions. The lysogen also carries the cl857 temperature-sensitive repressor mutation. Induction of the lysogen is described in the Examples. A similar strategy can be used to generate ribozyme-encoding plasmids packaged into bacteriophage P1 virions.

A common bacteriophage of *E. coli*, P1, is an attractive delivery vehicle for a multi-ribozyme for a number of reasons. First and foremost, P1 has a broad intergenera and interspecies range (Yarmolinsky, M. B., and N. Steinberg, 1988, Bacteriophage, P1, p. 291-438. In R. Calendar (ed.), The Bacteriophages, vol. 1, Plenum Press. New York). The P1 receptor of *E. coli* is the terminal glucose of the lipopolysaccharide (LPS) core lysergic ring of the bacterial outer membrane (Masters, M., 1966, Generalized Transduction, p. 2421-2441. In F. Neidhardt (ed.), *Escherichia coli* and Salmonella: Cellular and Molecular Biology, 2d ed. Vol. 2, ASM Press, Washington, D.C.). Yarmolinsky and Stemberg report that in addition to *E. coli*, this particular phage has the ability to inject its nucleic acid into a large number (>25) of diverse gram negative bacteria (Yarmolinsky, M. B., and N. Steinberg, supra) Secondly, P1 can accommodate a significant amount of genetic information, over 2% (100,000 bp) of the DNA of *E. coli* (Masters, M., supra). Consequently, gene dosage of the ribozymes can be increased through multiplication of the present ribozyme cassettes, thereby increasing the microbicidal activity of the multi-ribozyme. Bacterial strains already exist that can be readily modified to package ribozyme coding DNA in vivo by a process similar to that described above. Additionally, a process utilizing in vitro packaging is also possible, in vitro packaging can be accomplished through the addition of PAC-sites to the genetic information already present within the ribozyme construct. P1 packaging initiates within one of the P1 PAC genes (Sternberg, N., and J. Coulby, 1987, J. Mol. Biol. 194(3):469-79). It has been reported that the active PAC site is contained within a 161 base-pair segment of the P1 EcoR1 fragment 20 (Sternberg, N., and J. Coulby, supra). Thus, the phage head serves as a molecular syringe that delivers the inactivating ribozyme(s) to the pathogen.

5.4 Host Cells

The present invention encompasses the expression of the multi-ribozymes in primary cells, animal and insect cell lines for in vitro screening assay and ex vivo gene therapy. In accordance with the present invention, a variety of primary or secondary cells or cell strains may be used including but not limited to cells isolated from skin, bone marrow, liver, pancreas, kidney, adrenal and neurological tissue to name a few. Other cells types that may be used in accordance with the present invention are immune cells (such as T-cells, B-cells, natural killer cells, etc.), macrophages/monocytes, adipocytes, pericytes, fibroblasts, neuronal cells, reticular cells etc. In a further embodiment, secondary cell lines may be used as engineered responsive cells and tissues in accordance with the present invention, including, but not limited to hepatic cell lines, such as CWSV, NR, Chang liver cells, or other cell lines such as CHO, VERO, BHK, Hela, COS, MDCK, 293, 373, CaSki and W138 cell lines.

For long term, high-yield production of recombinant proteins, stable expression is preferred. For example, cell lines which stably express the selected target epitope may be engineered. Rather than using expression vectors which contain viral origins of replication, host cells can be transformed with DNA controlled by appropriate expression control elements (e.g., promoter sequences, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media.

The selectable marker in the recombinant plasmid confers resistance to the selection foci (e.g., by stably integrating the plasmid into their chromosomes) and allows cells to and grow to form which in turn can be cloned and expanded into cell lines. This method may advantageously be used to engineer cell lines. This method may advantageously be used to engineer cell lines which express the selected gene products. Such cell lines would be particularly useful in screening and evaluation of compounds that affect the endogenous activity of the selected gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: DHFR, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

5.5 Target Selection & Target RNA Cleavage

The complexity of human RNA is about 100 fold lower than that for human DNA, and specificity can be achieved with as few as 12-15 base pairs. The stability of the RNA-RNA duplex is effected by several factors, such as GC content, temperature, pH, ionic concentration, and structure. The nearest neighbor rules can provide a useful estimate of the stability of the duplex (Castanotto et al., 1994, Advances in Pharmacol. 25:289-317).

The catalytic ribozyme of the invention also includes a catalytic sequence, which cleaves the target RNA near the middle of the site to which the target RNA-specific binding site (sequences) bind. In the hammerhead-type of ribozyme, the catalytic sequence is generally highly conserved (Bertrand E., et al., 1994, Nucleic Acids Research 22(3):293-300; Inokuchi, Y., N. et al., 1994, J. biol. Chem. 269(15):11361-6). The conserved catalytic core residues are 5' <u>CUGANGA</u> 3' and 5' <u>GAAA</u>3' linked by an evolutionarily conserved stem-loop structure.

The most conserved and probably most efficiently cleaved sequence on the target RNA is 5' GUC 3'. However, NUX (wherein X=A, U or C) can also be cleaved efficiently. Such cleavage sites are ubiquitous in most RNAs allowing essentially all RNA's to be targeted (Whitton, J. Lindsay "Antisense Treatment of Viral Infection" Adv. in Virus Res. Vol. 44, 1994).

With regard to the selection of the appropriate sites on target RNA, it is known that target site secondary structure can have an effect on cleavage in vitro (Whitton, 1994, supra). A number of procedures are available to select accessible sites in RNA targets. In a preferred procedure, a library screen may be employed to select appropriate sites on the target RNA. Accessibility of the selected site may then be confirmed using techniques known to those skilled in the art. Thus, the selected target molecule's sequence can be routinely screened for potential secondary structure, using the program RNAFOLD (from the PCGENE group of programs or available on the Internet). Thus, reasonable predictions of target accessibility can be made. Computer assisted RNA folding (Castanotto et al., 1994, supra), along with computational analysis for 3-dimensional modeling of RNA (Major et al., Science 253:1255-1260, 1991 and Castanotto et al., 1994, supra) is certainly effective in guiding the choice of cleavage sites.

The multi-ribozymes of the present invention may be engineered to target a wide variety of cellular RNAs, tumor or cancer associated with RNAs, parasitic RNA etc. The internal ribozyme can be targeted to noncellular RNAs necessary for growth of parasites, virus life cycles, etc., and expression can be driven with tissue-specific or virus-specific promoters.

The first critical component in the assembly of the multi-ribozyme is the selection of appropriate RNA targets. For ribozymes to be effective anti-microbial therapy, it is preferable to target the RNA of, for example, several key or essential proteins, tRNA, rRNA or any other RNA molecule essential for cell viability or fitness, in order to insure complete inactivation and prevent escape of the invading microorganism. For example, four bacterial genes, essential for viability and unrelated in activity, have been selected and are described herein to highlight how the selection of appropriate mRNA targets is carried out for the preferred construction of the multi-ribozyme against prokaryotic targets. Cross-genera RNA targets can be used to design a multi-ribozyme that can have broad application, modified by the specificity of the promoter.

In one embodiment of the invention, the first ribozyme targets an essential transcription factor, the second ribozyme targets an essential general secretory component, the third ribozyme targets an essential component of the primosome required for DNA biosynthesis and the fourth ribozyme targets an enzyme required for cell division. Consequently, the ribozymes are redundant in the fact that they inhibit growth by specifically targeting a fundamental process required for bacterial growth. Thus, this can minimize the development of resistance to the antimicrobial therapeutic.

Examples of ribozymes targets of the invention include but are not limited to the following:

The first gene, rpoA, produces an essential protein, rpoA or the alpha subunit of RNA core polymerase. rpoA was selected rather than the other components of the RNA polymerase holoenzyme, because it is thought to facilitate the assembly of an active RNA Polymerase enzyme complex. Inactivation of the rpoA transcript results in a decrease in the intracellular concentration of the holoenzyme RNA polymerase rendering the cell less able to respond to changes demanded of it once it has invaded a new host. The nucleotide sequence of rpoA is known for a large number of microorganisms (>20 genera) and they are readily available from GenBank.

The second ribozyme target can be the mRNA of the secA gene from bacteria. The product of this gene is the essential and rate-limiting component of the general secretory pathway in bacteria (Bassford, P., et al., 1991, Cell 65(30):367-368). secA has been found in every prokaryotic cell investigated to date. Additionally, its biosynthesis is translationally coupled to the upstream gene, X (Schmidt, M. G., et al., 1991, J. Bacteriol. 173(20):6605-11), presenting a convenient target for a ribozyme. Inhibition or decreased synthesis of secA is also sufficient to confer a reduction in viability to the cell (Schmidt, M. D., and D. B. Oliver, 1989, J. Bacteriol. 171(2): 643-9). Furthermore, as a pathogen responds to changes required of the infectious process a change in the availability of a key protein such as secA will disadvantage the pathogen enabling the host to counteract it. Finally, control over the secretion-responsive expression of secA is at the level of translation (Christoffersen, R. E., and J. J. Mann. 1995, J. Med. Chem. 38(12):2023-37), and the regulatory sequences within its polycistronic message have been localized to a region comprised of the end of the upstream gene, X, and the beginning of secA. Consequently, inactivation of the transcript by the catalytic cleavage of a ribozyme has profound consequences for the viability of the invading microorganism.

The third ribozyme can target an essential factor for DNA biosynthesis, DnaG. Every 1 to 2 seconds, at least 1,000 times for each replication fork within *E. coli*, priming of an Okazaki fragment is repeated as a result of an interaction between the cellular primase DnaG (Bouche, J. P., et al., 1975, J. Biol. Chem. 250:5995-6001) and DnaB (Marians, K. J. 1996, Replication Fork Propagation, p. 749-763. In F. C. Neidhardt (ed.), *Escherichia coli* and Salmonella: Cellular and Molecular Biology, 2nd ed, vol. 1. American Society for Microbiology, Washington, D.C.). As would be expected of protein required every 1 to 2 seconds during replication, a lesion within dnaG or an alteration in its concentration results in an immediate stop phenotype (Marians, K. J. 1996, supra; Weschler, J. A. and J. D. Gross, 1971, Mol. Gen. Genet. 113:273-284). Therefore, inactivation of the dnaG message by a ribozyme should have profound cellular consequences in that general priming of the lagging strand is reduced if not eliminated. DnaG is a component of the primosome, a multiprotein complex responsible for priming replication. Any of the components of the primosome, either individually or in any combination, can serve as a target for inactivation of the primosome and, thus, kill the cell. The other components of the primosome are DnaB, DnaC, DnaT, PriA, PriB, and PriC. Thus, the primosome is also sufficiently complex to provide numerous other targets (DnaB, DnaC, DnaT, PriA, PriB and PriC) for inactivation by the trans ribozyme.

The fourth target can be ftsZ. This gene also encodes an essential protein, ftsZ, that is required for cell division in that it is responsible for the initiation of separation (see e.g., Tetart, F., and J. P. Bouche, 1992, Mo. Microbiaol. 6(5):615-20; Haseloff, J., and W. L. Gerlach, 1988, Nature 334(6183): 585-91; Sullivan, S. M., 1994, J. Invest Dermatol. 103(5 Supl):858-895). ftsZ was selected because its synthesis was under the control of an antisense RNA molecule encoded by the gene dicE. Transcription of dicE is all that is needed to inhibit the translation of ftsZ; thus, overexpression of this antisense molecule is sufficient to cause an inhibition of cell division and a reduction in viability. There is an advantage of using a ribozyme against ftsZ over the antisense molecule, dicE. Specifically, the ribozyme functions catalytically while dicE functions stoichiometrically. Thus, upon cleavage of the ftsZ message the ribozyme attacks additional copies of ftsZ inhibiting the division of the cell. The nucleotide sequence of ftsZ like the other targets selected, is commonly available from GenBank.

Important examples which are specifically presented in the application are:

A) Use of the albumin promoter with a Hepatitis B virus target (chosen to cleave the viral RNA pregenome, S protein, polymerase/reverse transcriptase, and polymerase/and x protein transcripts using the same ribozyme target site);
  B) Use of generic promoters active in erythrocytes, using a ribozyme targeted to highly conserved regions of the EMP-1 protein family from *P. falciparum*, which are necessary for cytoadherence and antigenic variation in malaria; and
  C) Use of the keratin 7 promoter, with trans-acting ribozymes targeted to a specific sites near the translational start site of the E6 protein, a site known to be critical for expression of both the E6 and E7 proteins which are intimately involved in cervical carcinogenesis, as well as a more 3' site in a highly conserved region of the E6 protein.
  D) Use of the HBV or HPV early promoter, with trans-acting ribozymes targeted to a specific sites near the translational start site of the E6 protein, a site known to be critical for expression of both the E6 and E7 proteins which are intimately involved in cervical carcinogenesis, as well as a more 3' site in a highly conserved region of the E6 protein.

Examples of bacterial pathogens that can be targeted by the multi-ribozyme construct of the present invention include, but are not limited to, species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Pasteurella, Clostridium, Corynebacterium, Listeria, Bacillus, Erysipelothrix, Rhodococcus, Escherichia, Klebsiella, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae* and any other bacterial species or genera now known or later identified to be pathogenic.

The pathogen of the present invention can also include, but is not limited to pathogenic species of yeast/fungal genera (e.g., *Candida, Cryptococcus, Aspergillus, Trichophyton, Microsporum*) as well as any other yeast or fungus now known or later identified to be pathogenic. Furthermore, the pathogen of the present invention can be a parasite, including, but not limited to, members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Ameson, Glugea, Pleistophora* and *Microsporidium* spp.; and members of the Ascetospora phylum such as, for example, *Haplosporidium* spp., as well as any other parasite now known or later identified to be pathogenic.

Examples of viral pathogens include, but are not limited to, retroviruses (human immunodeficiency viruses), herpes viruses (herpes simplex virus; Epstein Barr virus; varicella zoster virus), orthomyxoviruses (influenza), paramyxoviruses (measles virus; mumps virus; respiratory syncytial virus), picorna viruses (Coxsackie viruses; rhinoviruses), hepatitis viruses (hepatitis C), bunyaviruses (hantavirus; Rift Valley fever virus), arenaviruses (Lassa fever virus), flaviviruses (dengue fever virus; yellow fever virus; chikungunya virus), adenoviruses, birnaviruses, phleboviruses, caliciviruses, hepadnaviruses, orbiviruses, papovaviruses, poxviruses, reoviruses, rotaviruses, rhabdoviruses, parvoviruses, alphaviruses, pestiviruses, rubiviruses, filiviruses, coronaviruses and any other virus now known or later identified to be pathogenic.

The virion construct used in this method can comprise any ribozyme-encoding nucleic acid, particularly those described herein targeted to genes of the pathogen. The virion can be a bacteriophage, or other virus selected for its ability to target a specific cell-type, microorganism or animal. The bacteriophage can be lambda, P1 or other phage. When P1 is the virion, the non-viral DNA can further comprise a PAC site is also provided. This construct is preferred when using P1. Alternatively, the virion can be selected because it has a broad range of targets.

The above targeting method, wherein the virion is a bacteriophage is provided. The bacteriophage can be lambda, P1 or other phage. The targeting method, wherein the non-viral DNA further comprises a PAC site is also provided. This construct is preferred when using P1.

It should be clear that any other essential protein of a pathogen can have its message targeted in the present invention, and that determining which proteins are essential can be routinely determined according to standard protocols in the art. In fact, there are over 52,000 viral, 41,000 bacterial and 12,300 fungal sequences deposited in the public section of the Entrez Database at the National Center for Biotechnology Information. Any of these can be used to design the catalytic trans ribozyme of the multi-ribozyme. Thus, multi-ribozyme can comprise ribozymes targeted to these other messages.

In addition to targeting mRNA of essential proteins ribozymes may be targeted against other RNA species within the cell. Specifically, appropriate targets in bacteria, fungi and other lower eukarytoes include ribosomal RNA such as Small Subunit RNAs (SSU) or Large Subunit (LSU) and tRNA molecules required for protein synthesis. For example, with respect to pathogenic Staphlococus, the RNA III moiety is a relatively low abundance transcript which is not translated and should be accessible for cleavage. As long as the RNA targeted contains a canonical ribozyme cleavage domain the multi-ribozyme therapeutic can hybridize and cleave the complementary RNA, thus impacting the fitness of the microbial cell. Additionally, over 3000 rRNA species have been sequenced and aligned. This information is available from the Ribosomal Database Project and should facilitate rapid design and adaptation of ribozyme(s) against such targets. For example the 16S rRNA molecule of bacteria is especially attractive in that there are over 4000 copies of the 16S rRNA per cell. Consequently, a reduction in number slows the process of protein synthesis in so far as the 16S rRNA molecule is involved in the process of translational initiation. Thus, a multi-ribozyme containing ribozymes directed against mRNA and rRNA impacts the fitness of the offending microorganism.

5.6 Screening for Novel Trans-acting Ribozymes and Targets

The present invention encompasses the expression of the multi-ribozymes in primary cells, animal and insect cell lines for in vitro screening assay and ex vivo gene therapy. The present invention also relates to library screening that allows the identification of potential trans-acting ribozymes that may be used in the present invention. For example, the present invention provides in vivo hammerhead ribozyme library screen, as outlined in FIG. 9. Generally, the hammerhead ribozyme library screen delivers a ribozyme library to host cells (such as prokaryotic/bacterial cells) which expresses the library upon induction (e.g., by methods known in the art). Any clones which carry a lethal ribozyme construct are detected by differences in, or lack of the clone on a replica plate. The clone is then recovered, the ribozyme is characterized, and the RNA target identified.

This procedure is accomplished by a combination of several techniques known in the art. The plasmid vector which is constructed to contain a regulated promoter. In a preferred embodiment, the regulated promoter will have tight repression in the host cell in the uninduced state which allows for maintenance of the potentially lethal plasmid within the host. Upon induction (or de-repression of the promoter) a large excess of transcribed product is expressed. When the expressed product (e.g., trans-acting ribozyme) is a sequence for a highly toxic, host-specific ribozyme, the host cell will die.

The library itself is a hammerhead ribozyme structure with degenerate bases for the two antisense arms (helix I and III). In a preferred embodiment, the library contains all ribozymes capable of binds to and cleaving any stretch of accessible RNA sequence containing the NUX motif. The library is constructed from a custom synthesized single stranded oligonucleotide. A second strand is synthesized in vitro utilizing a compatible primer and polymerase. The double-stranded oligonucleotide is trimmed with restriction endonucleases to allow for directional cloning into the plasmid vector (such as the modified pChop cassette vector) prepared with compatible cohesive ends. In one embodiment, the plasmid vector utilizes the modified pChop expression cassette which releases the trimmed, transacting, internal ribozyme in an autocatalytic manner upon transcription. The modified pChop also provides a 3' hairpin loop on the internal ribozyme to protect it from exonuclease attack. Additionally, a lacI gene may be cloned onto the plasmid vector to allow for tighter repression of lac operator containing modified pChop expression promoters. In other embodiments of the invention the screening cassette is pClip, pChop, or pSnip cassette. In still other embodiments of the invention, more than one cassette is used.

One technique for detecting the lethal events utilizes replica plating. The library is ligated into the appropriate plasmid vector and this ligation is transformed into the bacterial host cells. In one embodiment of the invention, the host cells have a ribosome deficiency such that they are slow-ribosome host cells. The cells are plated onto solid media with the appropriate antibiotic selection and allowed to grow until small, isolated colonies are present. The dish is replica plated using sterile velvet onto solid media containing the inducer compound. Ribozyme expression is then induced in the replica plate colonies (one ribozyme sequence per clonal colony). Replica plates are incubated for approximately equivalent time as the parent plate was originally allowed to incubate, so that colony sizes of the parent plate and replica plate are similar. When the ribozyme is lethal or toxic to the cell, the toxic or lethal ribozyme-containing colony will not grow on the replica plate. Toxic or lethal ribozyme-containing colonies are detected by comparison of the two plates (parent and replica). The original colony corresponding to a lethal ribozyme can be picked and propagated from the original parent plate by standard techniques in the art. The sequence of the ribozyme of the colony is then determined by standard methods in the art. The RNA target may also be determined by complementation. Once sequenced, ribozymes revealed in the screen may be redesigned and refined to enhance the activity of the ribozymes.

The ribozyme screen provides two important advantages. First, it demonstrates whether particular hammerhead ribozymes can be used as a lethal agent in the given host species. The ribozyme library represents approximately 6.7× $10^7$ unique hammerhead ribozyme sequences. Following screening of a significant number of colonies (and thus ribozyme sequences), should no lethal events be detected, then the single trans-acting ribozyme approach may be less preferred for the given species. Importantly, however, the expression and screening system is preferably optimized and validated for the host species under investigation. For example, as described in the Section 6, herein, in an *E. coli* host, the UPRIP (LEASHI) promoter expressing the modified pChop cassette coupled with AP LacI element on a pBluescript plasmid backbone gives the highest ratio of induced versus repressed expression levels when assayed in bacterial Sθ3831slow-ribosome cells.

Another important advantage of the screening system is when a positive colony is detected, the ribozyme is known to be lethal in an in vivo system. Thus there is decreased discrepancy due to differences arising from in vitro to in vivo systems. Thus, the in vivo screening methods directly demonstrate a susceptible target as well as an effective lethal trans-acting ribozyme.

5.7 Multi-Ribozyme Design

The multi-ribozyme ribozyme possesses sufficient catalytic activity to inactivate the RNA of the targeted RNAs. From an antimicrobial perspective, hammerhead-type ribozymes are especially attractive since the molecule inactivates gene expression catalytically through the cleavage of the phosphodiester bond of the mRNA. Furthermore, hammerhead-type ribozymes have been re-engineered to function in an intermolecular or transducer (trans) acting state (Haseloff et al., 1988, Nature 334(6183):585-91; Uhlenbeck. O. C., 1987, Nature 328(6131):59). The catalytic activity of the ribozyme requires a sufficient concentration of the divalent cation, $Mg^{+2}$, and substrate. The substrate can have any sequence as long as the cleavages site contains the recognition element NUX, where N represents any nucleotide, U corresponds to uracil, and X is any nucleotide except G (Koizumi et al., 1989, Nucleic Acids Research. 17(17):7059-71). Ribozymes have been widely demonstrated to function in vivo (Christoffersen et al., 1995, J. Med. Chem. 38(12):2023-37; Inokuchi et al., 1994, J. Biol. Chem. 269(15):11361-6). The present invention improves the initial design of hammerhead-type ribozymes (Taira et al., 1991, NAR 19(9):5125-5130) by constructing multi-ribozymes consisting of ribozyme cassettes. Ribozyme cassettes contain one or more cis-acting hammerhead ribozymes flanking a ribozyme that inactivates the targeted RNA(s) as well as one or more flanking sequences. Upon transcription the targeted ribozyme is released as a 60-70 base transcript which not only improves its specificity by reducing non-specific interactions but also improves its catalytic activity as well. This invention includes modifications to and use of the ribozyme described in U.S. Ser. No. 08/554,369 and PCT publication No. WO98/24925, which are incorporated by reference herein in their entirety.

The ribozymes of the present invention have several important modifications. The arms of the cis-acting ribozymes have been lengthened by 20 bases. The sequence has been modified to enhance the catalytic activity of the cis-acting elements, for example, those shown in SEQ ID NOS:18-38. Additional restriction sites are included that facilitate easier cloning and manufacturing. Specifically, restriction enzymes have been chosen which produce cohesive ends, so that internal trans-acting ribozymes can be cloned into the ribozyme cassettes in a single vector facilitating construction of targeted ribozymes. Design on the internal ribozymes may also include the use of a hairpin loop at the 3' end of the internal ribozymes. In several embodiments, tRNA elements are present in the 3' end of the multi-ribozyme. The addition of the tRNA elements creates additional structure that improves the stability of multi-ribozyme helping it resist nuclease attack. An inverted nucleotide repeat has been inserted into the 3' end of the multi-ribozyme. The addition of the inverted repeat, a hairpin loop structure, improves the stability of multi-ribozyme, helping it resist nuclease attack (see e.g., Pace, N. R., and D. Smith, 1990, J. Biol. Chem. 256(7):3587-90; Schmidt, M., and N. Delihas, 1995, FEMS Microbiol. Lett. 133(3):209-13).

5.8 Protection of Ribozyme-Producing Cells

The genes or nucleic acids coding for the ribozymes can be toxic to the cells that are needed to produce the ribozyme-carrying virions. When using a broad host-range virus like P1, the organism used to produce the multi-ribozyme can be different from the target organism. In this way, the producing strain is resistant to the toxic effects of the ribozymes because the ribozymes are not efficiently expressed in the producing strain, due to species-specific promoter elements, and the ribozymes will not have any target RNA molecules to attack, due to the species-specific sequences that target the ribozymes. When using a species-specific virus that must be expressed and assembled within a strain of the targeted microorganism, this toxicity becomes a significant concern. The assembly of a multi-ribozyme consisting of anti-E. coli ribozyme genes packaged in lambda will illustrate the approach used to circumvent the toxicity. The ribozymes directed against RNA species of E. coli is expressed from a artificial promoter containing consensus promoter elements. This promoter provides high level transcription of the ribozyme immediately upon infection of targeted cells. In order to prevent the unwanted death of the producing strain of E. coli, transcription is repressed in the producing strain by a mechanism not available to the wildtype strains that are targeted for killing. Sequences constituting the DNA binding sites for a heterologous transcription factor are interspersed between the essential activating elements of the ribozyme promoter. Expression of the heterologous transcription factor in the producing strain results in the occlusion of the activating promoter elements and preventing the binding of RNA polymerase. As an example, the gene for the Saccharomyces cerevisiae transcription factor Ste12p may be expressed in E. coli and bind to its binding sites, the pheromone response element, located within the ribozyme promoter. Ste12p will not be found in wild strains of E. coli; therefore, the ribozyme promoter will be accessible to RNA polymerase following delivery of the plasmid to the targeted cells.

An alternative strategy that can protect the producing strain from the toxicity of the ribozymes employs ribozyme-resistant versions of the targeted RNA molecules. This strategy can be used when the target RNA molecule codes for a protein. The ribozyme target site within the mRNA molecule is mutated by site-directed mutagenesis such that the amino acid sequence of the translated protein does not change but the mRNA sequence no longer serves as a substrate for the ribozyme. For example, hammerhead ribozymes require an NUX sequence within the target mRNA for cleavage to occur. By changing this sequence to something else, the ribozyme will not cleave the mRNA. This type of ribozyme resistant version of the target RNA can be expressed from a plasmid or integrated into the chromosome of the producing strain and thus render this strain resistant to the toxic effects of the ribozyme.

Merrill and co-workers reported on the selection of long-circulating bacteriophages as anti-bacterial agents (Merril, C. R. et al., 1966, Proc. Natl. Acad. USA. 93:3188-3192). They were able to show that it is possible to select for phage variants that remain refractory to clearance by the reticuloendothelial system for a period of time sufficient to confer a therapeutic response within an infected animal (Merril, C., supra). Specifically, the phage will promptly induce neutralizing antibodies interfering with the phage's ability to attack against the bacteria and opsonins that will restore the vulnerability of the phage (Lederberg, J., 1966, Smaller fleas . . . ad infinitum: Therapeutic bacteriophage redux. Proc. Natl. Acad. Sci. USA 93:3167-3168.). The improvement in the present invention is that a non-replicative delivery system has an advantage in that once the phage coat has injected the nucleic acid into the targeted bacterium, the expression of the multi-ribozyme ribozyme will destroy the microbe, as opposed to a lytic infection cycle typical of an intact bacteriophage. Consequently, amplification of the phage coat will not be an issue and it is less likely that the non-replicative phage delivery system will generate an immune response such that subsequent use of the delivery system would be jeopardized. Moreover, if the patient has been exposed to a resistant pathogenic microbe and the multi-ribozyme is effective and neutralizes the invading microbe, then it is expected that the microbial antigens liberated as a result of the action of the multi-ribozyme, will illicit sufficient humoral immunity and cell-mediated immunity to confer protection against subsequent attacks.

5.9 Administration

A method of delivering a ribozyme to a target (e.g., a pathogen) in a subject is provided, comprising a) generating a liposome comprising a promoter and ribozyme-encoding sequence; and b) delivering the liposome to the subject, whereby the target-specific promoter directs transcription of the ribozyme in the cells of the target. The target can be a pathogen, for example, a bacteria, fungus, yeast, parasite, virus or non-viral pathogen.

A method of targeted delivery of a ribozyme to a pathogen in a subject, comprising a) generating a virion comprising non-viral DNA of the invention; b) combining it with a liposome; and b) delivering the liposome containing the virion to the subject, whereby liposome enters the eukaryotic cell and releases the virion, which delivers the DNA to the pathogen, whereby the pathogen-specific promoter directs transcription of the ribozyme(s) in the cells of the pathogen.

A method of treating an infection in a subject is provided, comprising administering to the subject the liposome comprising DNA comprising a target-specific promoter and encoding a ribozyme, whereby the ribozyme encoded by the DNA is expressed and the infectious agent is killed or weakened. The liposome used in this method can comprise any ribozyme-encoding nucleic acid, particularly those described herein targeted to genes of the pathogen. The infection can be bacterial, fungal, yeast, parasitic, viral or non-viral.

Parenteral administration, if used, is generally characterized by injection (intravenous, intradermal, subcutaneous and intramuscular). Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant level of dosage is maintained. See, e.g., U.S. Pat. No. 3,610,795, which is incorporated by reference herein.

Suitable carriers for parenteral administration of the substance in a sterile solution or suspension can include sterile water or saline that can contain additives, such as ethyl oleate or isopropyl myristate, and can be: injected, for example, intravenously, as well as into subcutaneous or intramuscular tissues.

Topical administration can be by creams, gels, suppositories and the like. Ex vivo (extracorporeal) delivery can be as typically used in other contexts.

Oral administration is also contemplated. Suitable carriers for oral administration include one or more substances which can also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers can be water, pyrogen free saline, pharmaceutically accepted oils, or a mixture of any of these. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

The multi-ribozyme can be administered to the subject in amounts sufficient to produce an antibiotic effect or to inhibit or reduce the activity of the target pathogen. Optimal dosages used will vary according to the individual, on the basis of age, size, weight, condition, etc, as well as the particular modulating effect being induced. One skilled in the art will realize that dosages are best optimized by the practicing physician and methods determining dosage are described, for example, in Remington's Pharmaceutical Sciences (Martin, E. W. (ed.) Remington's Pharmaceutical Sciences, latest edition Mack Publishing Co., Easton, Pa.). Treatment can be at intervals and can be continued for an indefinite period of time, as indicated by monitoring of the signs, symptoms and clinical parameters associated with a particular infection. The parameters associated with infection are well known for many pathogens and can be routinely assessed during the course treatment.

6. EXAMPLES

Promoter Selection

Promoters specific for the targets are selected by screening genomic sequences as described, supra. For non-viral pathogens, plasmid capable of stable replication and maintenance in the microorganism was modified by standard molecular biology techniques to carry the coding region of a reporter gene (Sambrook et al., supra). The reporter gene is any standard reporter gene known in the art including but not limited to the lacZ gene of E. coli, which codes for β-galactosidase. Total genomic DNA is isolated from cells of the pathogen, cleaved with restriction endonucleases to yield fragments of a few hundred basepairs on average. These fragments are then ligated into a unique restriction endonuclease cleavage site at the 5' end of the reporter gene coding region, creating a library of plasmids. The library is then transformed into the pathogen by standard techniques and the resulting transformants are screened for expression of the reporter gene. In the case of lacZ, the transformants can be plated onto medium containing the chromogenic-galactosidase substrate X-Gal (5-bromo-4-chloro-3-indolyl-D-galactoside). Transformants that contain a plasmid with an insert carrying a promoter will express β-galactosidase and will turn blue on X-Gal plates. The intensity of the blue color is relative to the level of expression; promoters of different strength can be selected based on the intensity of the blue color.

To test for species-specificity, the identified promoters are transferred to promoterless reporter plasmids capable of replication and maintenance in a different organism. Truly species-specific promoters will not activate the expression of the reporter gene in any other species. Obvious modifications can be used to identify and test artificial promoters composed of synthetic oligonucleotides inserted into the promoterless reporter plasmid.

Several pathogen-specific promoters have been discovered by the inventors to be useful in the methods and compositions of the invention and serve to illustrate the present invention. Three pseudomonas promoters include ARN, PROC, and ARC.

```
ARN:   5'ACTCGCGGA TCATCTTCAC CATCGGCCGC AACTCCTGCG          (SEQ ID NO:
                                                              1)
       GGATATCCTC GTCCTCCTCC TCCACCGGCA CCCCCATGGT AGCGGCCAGC

TCGCGCCCTG CCTGGGAAAG CTGTACATGC TGATCGGCGG CGTCGGTGCC

GGCGGCCGGG TCTTCCGCCT GCTCGGCGGT GCCGGTCCGT GCGGCCTTGG

CGTCCGCGGC GGCGCGCGAT GAGGGCGGCA CCTGGGTGGT GATCCAGCCA

CTGAGGGTCA ACATTCCAGT CACTCCGGGA AAATGGAAT TCTTCCATTG

GATCGGCCCA CGCGTCGCGA ACTTGAGCCC CCTTTTCGTC GCCCCTTGAC

AGGGTGCGAC AGGTAGTCGC AGTTGTTTGA CGCAAGTCAC TGATTGGAAA

CGCCATCGGC CTGTCAGAAA TGGTCGTTGCC AGACCTATGG CTGGCACCCG

CATCGCGGCT GCGTTACCCT TACTCCTGTT GTGCCTTTAA CCTAGCAAGG AC

PROC:  5'AATTCCTCGA AGTCCTTGCG CTGCTTGTCG TTCATGATGT          (SEQ ID NO:
                                                              2)
       CGTAGATCAG CGCATGCACC TGCTTGTGTT CCAGCGGTGG CAGGTTGATC

CGGCGTACAT CGCCATCCAC CCGGATCATG GGTGGCAGGC CGGCGGAGAG

GTGCAGGTCC GAAGCGCCCT GTTTGGCACT GAAGGCGAGC AGCTCGGTAA

TATCCATGGG ACTCCCCAAT TACAAGCAAG CAGGTAGAAT GCCGCCAAAG

CCGCCGTCTC GGACAAGGAA AACACCGGAT GAGCCAGGGT GCTTCCAGGA

CACGCGTGGT GTCCTGCGCC AGACGCGGAA CCTCGACACT GGAACAGGAA

GATGGCCATC GAGGCCGGCG GTTTCGAGGG CGTCGAGCCG ACGCCGACCG

CACTTCCATA GGGCGCAGGT AATGTCCACG ATAGCAGAGA ATATTGCAAA

GGTTGCCGCG CGCATCCGTG AGGCAGCGCA AGCTGCGGGG CGCGATCCGG

CCACGGTCGG CCTGCTCGCC GTGAGCAAGA CCAAGCCCGC CGCCGCGGTG

CGCGAGGCGC ACGCCGCCGG CCTTCGCGAC TTCGGCGAAA ACTACCTGCA

GGAGGCCCTC GGCAAGCAGG CCGAACTGGC CGACCTGCCC TTGAACTGGC

ACTTCATCGG CCCCATCCAG TCGAACAAGA CGCGGCCCAT CGCCGAGCAT

TTCCAGTGGG TGCACTCGGT GGACCGGTTG AAGATCGCGC AGCGCCTGTC

GGAGCAACGC CCGGCCGGGC TGCCGCCCCT GAATGTCTGC CTGCAGGTCA

ACGTCAGCGG CGAAGCCAGC AAGTCCGGCT GCGCCCCCGA GGACCTGCCG

GCCCTGGCCG AGGCCGTGAA GCAACTGCCC AACCTCCGAT TGCGTGGCCT

GATGGCCATC CCCGAACCCA CCGCCGAACG CGCCGCGCAA CACGCCGCGT

TCGCCCGCCT GCGCGAACTG CTGCTGGACC TGAACCTTGG CCTGGACACC

CTGTCCATGG GCATGAGCGA CGACCTCGAG GCAGCCATCG CGAAGGTGCG

ACCTGGGTCC GCATCGGTAC CGCCCTGTTC GGCGCCCGCGA CTACGGCGCG

CCGGCTTCTT GAATGAATCCC

ARC:   5'CTAGAGCTAT TGATGTGGAT CAACATTGTC CACTAGCCGC          (SEQ ID NO:
                                                              3)
       TGCCGCCTAA TCTCCAGAAT TGTGAG
```

The invention provides modifications of the ribozyme cassettes described herein. In the following example, the pChop cassette has been modified to include a spacer insert (~300 bases of DNA between the Eco and Bam sites) as well as a modified hairpin on the 3' end of structure, and a TL17 terminator sequence. Without limitation, the spacer insert facilitates cloning and preparation of the vector with decreased background. Generally, the spacer insert is excised prior to cloning in an insert (such as a sequence from a library). The modified hairpin provides protection against 3'->5' exonuclease activity. The hairpin loop is liberated along with the trans-acting ribozyme(s) and forms a secondary protective structure. The TL17 terminator sequence serves to stop prokaryotic transcription following expression of the entire modified pChop cassette, and may act as a transcriptional terminator in both directions (thus preventing reverse read-through transcription). The modified cassette, indicated as UPCM2, below, was linked to the LESHI promoter (see U.S. patent application Ser. No. 09/291,902, filed Apr. 14, 1999, incorporated herein by reference in its entirety). The cassette was further cloned into pBluescript II sk vector (Statagene, Inc.) Further, an AP LacI element was cloned downstream of the cassette. The AP promoter is a strong constitutive promoter that linked to Lac I. Lac I expression provides tighter regulation (e.g., in the uninduced state).

The modified cassette was used in in vivo ribozyme library screening. A hammerhead ribozyme library was constructed with degenerate bases for the two antisense arms (helix I and III), such that the library contains essentially all ribozymes capable of binds to and cleaving any stretch of accessible RNA sequence containing the NUX motif. The library was constructed from a custom synthesized single stranded oligonucleotide. The ribozyme library represents approximately $6.7 \times 10^7$ unique hammerhead ribozyme sequences. A second strand was synthesized in vitro utilizing a compatible primer and polymerase. The double-stranded oligonucleotide was then trimmed with restriction endonucleases to allow for directional cloning into the plasmid vector, the modified pChop cassette vector, prepared with compatible cohesive ends. Additionally, a lacI gene was cloned onto the plasmid vector to allow for tighter repression of lac operator containing modified pChop expression promoters. The ribozyme library was then ligated into the vector (modified pChop cassette on a pBluescript backbone plasmid) and this ligation is transformed into E. coli host cells. The cells were plated onto a dish containing solid media with the Ampicillin antibiotic selection and allowed to grow until small, isolated colonies were present. The dish was then replica plated using sterile velvet onto solid media containing the inducer compound, IPTG. Replica plates are incubated for approximately equivalent time as the parent plate. Following incubation, parent and replica plates were compared, and putative positive colonies (those showing a difference between the parent and replica plate) were picked and propagated from the original parent plate by standard techniques in the art. The highest ratio of induced versus repressed expression levels was in E. coli S003831 slow-ribosome cells. The sequence of the ribozyme of the picked colony was then determined by standard methods in the art. The RNA target was also determined. Once sequenced, ribozymes revealed in the screen were further redesigned and refined to enhance the activity of the ribozymes.

UPCM2 cassette sequence
(SEQ ID NO: 4)
```
5'-TCAGAAAATTATTTTAAATTTCCAATTGACATTGTGAGCGGATAACA

ATATAATGTGTGGAAGCTTATCGATACCGTCGACCTCGAAGCTTTGGAAC

CCTGATGAGTCCGTGAGGACGAAACGATGACATTCTGCTGACCAGATTCA

CGGTCAGCAGAATGTCATCGTCGGTTCCAGGATCCGGCTGCTAACAAAGC

CCGAAAGGAAGCTGAGTTGGCTGCTGCCACCGCTGAGCAATAACTAGCAT

AACCCCTTGGGGCCTCTAAACGGGTCTTGAGGGGTTTTTGCTGAAAGGA

GGAACTATATCCGGATATCCCGCAAGAGGCCCGGCAGTACCGGCATAACC
```

-continued
```
AAGCCTATGCCTACAGCATCCAGGGTGACGGTGCCGAGGATGACGATGAG

CGCATTGTTAGATTTCATACACGGTGCCTGACTGCGTTAGCAATTTAACT

GTGATAAACTACCGCATTAAAGCTTATCGATGATAAGCTGTCAAACATGA

GAATTCGGCGTATACGCCGAATTTCAAGGGTCTGCGCAACGACGACGATG

AGGTACCACATCGTCGTCGTTGCGCACTGATGAGGCCGTGAGGCCGAAAC

CCTTGACGCGTAAAAAAACCCGCCCCGGCGGGTTTTTTACCCTTCCTAT

GCGGCCGCTCTAGTCGAGGGGGGGCCCGCTAGAACTAG-3'
```

A second modified cassette that has been constructed is the P2CM2, indicated below, which provides a modified pChop cassette which has been modified to include a spacer insert (~300 bases of DNA between the Eco and Bam sites) as well as a modified hairpin on the 3' end of structure, and a TL17 terminator sequence. The second modified cassette, indicated as UPCM2, below, was linked to the P2 promoter.

P2CM2 cassette sequence
(SEQ ID NO: 5)
```
5'-AGAAAGCAAAATAAATGCTTGACACTGTAGCGGGAAGGCGTATAAT

GGAATTGTGAGCGGATAACAATTCACAAGCTTATCGATACCGTCGACCTC

GAGCTTTGGAACCCTGATGAGTCCGTGAGGACGAAACGATGACATTCTGC

TGACCAGATTCACGGTCAGCAGAATGTCATCGTCGGTTCCAGGATCCGGC

TGCTAACAAAGCCCGAAAGGAAGCTGAGTTGGCTGCTGCCACCGCTGAGC

AATAACTAGCATAACCCCTTGGGGCCTCTAAACGGGTCTTGAGGGGTTTT

TTGCTGAAAGGAGGAACTATATCCGGATATCCCGCAAGAGGCCCGGCAGT

ACCGGCATAACCAAGCCTATGCCTACAGCATCCAGGGTGACGGTGCCGAG

GATGACGATGAGCGCATTGTTAGATTTCATACACGGTGCCTGACTGCGTT

AGCAATTTAACTGTGATAAACTACCGCATTAAAGCTTATCGATGATAAGC

TGTCAAACATGAGAATTCGGCGTATACGCCGAATTTCAAGGGTCTGCGCA

ACGACGACGATGAGGTACCACATCGTCGTCGTTGCGCACTGATGAGGCCG

TGAGGCCGAAACCCTTGACGCGTAAAAAAAACCCGCCCCGGCGGGTTTTT

TACGCGTTCCTATGCGGCCGCTCTAG-3'
```

Example of Tissue-specific Multi-Ribozymes

In one embodiment of the present invention, a multi-ribozyme is engineered to down-regulate a targeted RNA in a tissue-specific manner. In accordance with this embodiment, the multi-ribozyme may be designed to target sebum production and secretion and be designed for topical administration, which will down regulate sebum production via selective expression within the pilosebaceous unit. The DNA construct, placed within a suitable expression vector, comprises a tissue-specific promoter (from keratin K4, K7, or K13) driving expression of multi-ribozymes targeted against the androgen receptor (AR) and/or the enhancer protein steroidogenic factor 1 (SF 1). In one embodiment of the invention, the triple ribozyme cassette consists of two cis-acting ribozymes flanking a trans-acting internal ribozyme. The action of the cis-acting ribozymes liberates the internal targeted ribozyme with minimal flanking sequences, thereby enhancing its activity.

Sebum production and secretion is an important component in the pathogenesis of acne, and sebum production is regulated by androgens. Thus, the topical application of a formulation containing the multi-ribozyme of the present invention results in the inhibition of excessive sebum production/secretion by sebaceous glands in skin.

The approach utilized is to create a DNA construct within a suitable expression vector, which comprises a tissue-specific promoter driving expression of triple ribozymes, or multi-ribozyme of the invention which are targeted to cellular components important in sebum production. One target is the androgen receptor (AR), which is known to be important in the process. The Andogen Receptor is necessary for the androgen responsiveness and metabolism of androgen to activated forms, and metabolic processes which are controlled by enzymes whose expression is controlled by steroidogenic factor 1 (SF-1). The other target is steroidogenic factor 1 (SF1), which is an enhancer protein important for steroid metabolizing enzymes in the pathway which activates testosterone. The promoters utilized are those which drive expression of keratins 4, 7, and 13 (K4, K7, and K13); expression of these keratins are quite selective for sebaceous glands within the pilosebaceous unit, given the distribution of topically applied liposomal formulations. In one example of the invention, the triple ribozymes consist of two cis-acting ribozymes flanking an internal transacting ribozyme, which is targeted to AR and/or SF1. The two cis-acting ribozymes liberate the internal targeted ribozyme(s) with very short non-specific flanking sequences, thereby enhancing its efficiency and specificity.

Biologic Delivery

The multi-ribozymes of the present invention may be delivered by a wide variety of viral vectors and bacteriophage as described herein. In one embodiment, the multi-ribozymes are delivered via a plasmid encoding the ribozymes, a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of replication on the plasmid and all of the structural components needed to form mature virions; however, the lysogen is not able to replicate and package its own DNA into the virions. The lysogen also carries the $cI^{857}$ temperature-sensitive repressor mutation. Induction of the lysogen by temperature shift to 42° C. or by other means, such as exposure to 5 J/m$^2$ of ultraviolet radiation will mobilize the plasmid and result in its replication and packaging into lambda virions. The virions are then harvested, purified free of F. coli proteins and are used to deliver the ribozyme gene(s) or nucleic acid to *E. coli*.

Abiologic Delivery

Abiologic delivery of the Multi-ribozyme is accomplished with ribozyme(s) constructs that have been engineered to be expressed within the targeted tissue. Briefly, the genetic element containing the promoter and ribozyme(s) are complexed with cationic liposomes (Lipofectamine, Gibco BRL) in a 1:10 ratio and are introduced into test animals by either single or multiple injection of 0.2 ml total volume nucleic acid-liposome mixture.

In Vivo Testing

Following the demonstration that multi-ribozymes of the present invention have an in vitro biological activity (either directly on bacterial cultures or in an infectious tissue culture cell assay system), the effectiveness of the multi-ribozymes, is shown in an in vivo model system. To demonstrate the efficacy of multi-ribozyme in vivo, experimental animal model systems are utilized. For an initial demonstration of the efficacy of the multi-ribozyme in vivo, mice are infected with a microbial pathogen which has previously been shown to be sensitive to the multi-ribozyme construct(s) and the effect of multi-ribozyme administered in vivo is determined. In the first series of in vivo trials, one determines the effectiveness of a multi-ribozyme at preventing an acute infection in a murine model system when the multi-ribozyme is added directly to the microbe prior to administration in vivo. Examples of model systems that are useful in connection with the present invention include but are not limited to those presented in Abdul-Hassan, et al., 1990, Bacteriophage therapy of pseudomonas burn wound sepsis. Annals of the Mediterranean Burn Club. 34:262-264; Kwarcinski, W., B. Lzarakiewicz, B. Weber-Dabinwoska, J. Rudnicki, K. Kaminski, and M. Sciebura. 1994, Bakteriofagoterapia w. leczeniu nawracajacego ropnia podprzeponowego i podwatrobowlego oraz przetoki jewlitowej Patent Office wycieciu zoladka. Polski Tygodnik Lekarski. XLIX:23-23; Slopek, S., B. et al., 1987, Results of bacteriophage treatment of suppurative bacterial infections in the years 1981-1986, Arch. Immunol. Ther. Exp. (Warsz) 35:569-583; Smith. H. W., and M. B. Huggins, 1982, Successful treatment of experimental *Escherichia coli* infections in mice using phage: its general superiority over antibiotics. J. Gen. Microbiol. 128:307-318; and Soothill, J. S., 1994, Bacteriophage prevents destruction of skin grafts by Pseudomonas aeruginosa. Burns. 20:209-211.

The next series of trials determine whether the administration of multi-ribozyme after infection is effective at preventing an acute bacterial infections. In addition to the clinical status of infected mice, tissues obtained at necropsy are examined histologically and the presence of replicating microorganism in tissue samples is determined by standard methodology. Animals can be infected by various routes (systemic and/or mucosal) and the multi-ribozyme delivered over time after infection by systemic and/or mucosal routes. Both abiologic as well as biological delivery of multi-ribozyme is used. The demonstration of a positive effect of the multi-ribozyme in controlled experimental model system provides compelling evidence for the efficacy of the preparation and determines whether or not the preparation warrants evaluation under conditions of standard clinical trials.

Development and Testing of the Catalytic Component of the Multi-ribozyme

The following is a routine approach for designing, manufacturing and testing of the ribozymes that are incorporated into the multi-ribozyme invention.

Figure 1:
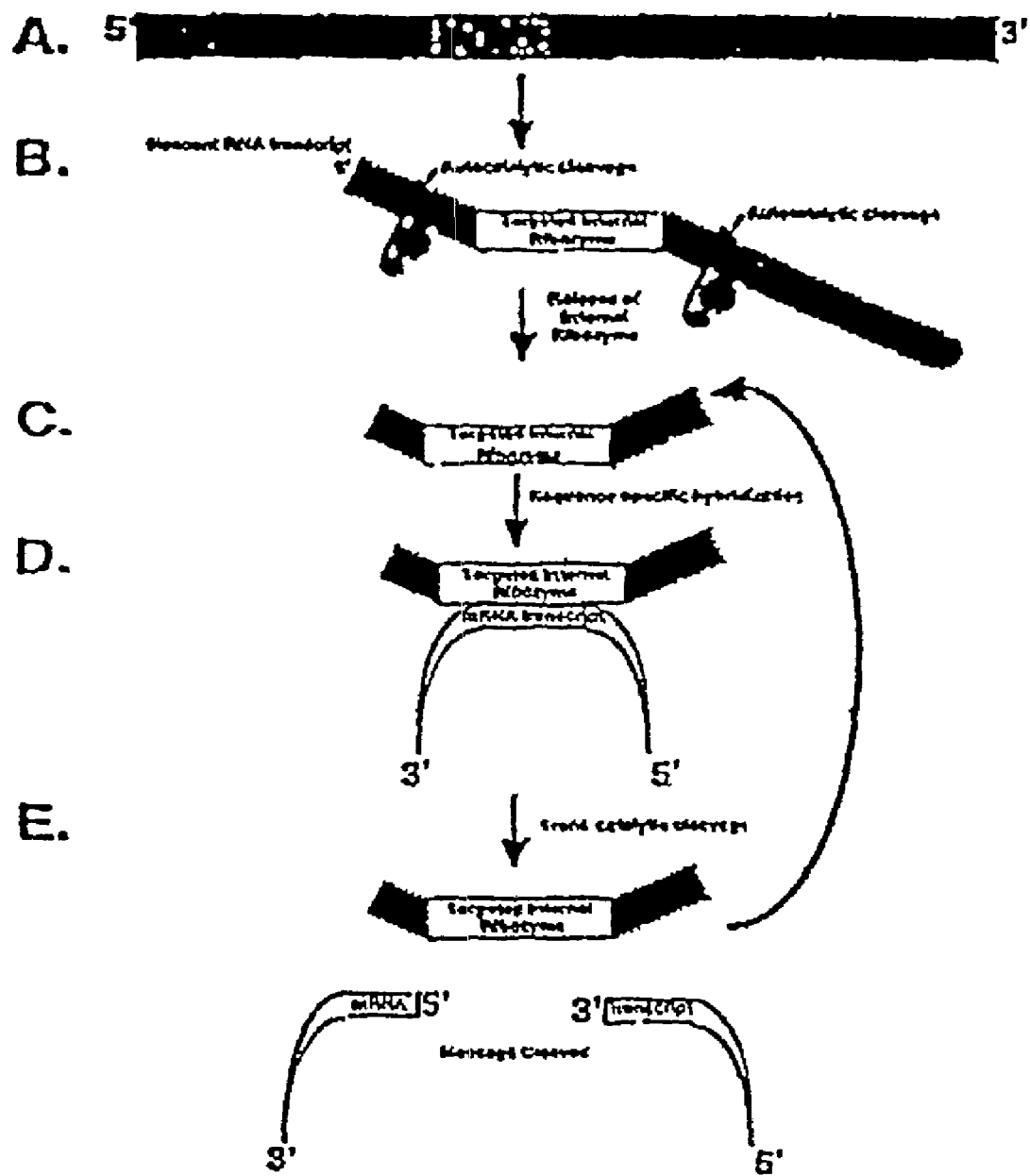
FIG. 1A shows a schematic of DNA encoding the ribozyme used in the molecular sequence of events in ribozyme maturation and action.
FIG. 1B shows the primary RNA transcript. Autocatalytic cleavage takes place upon completion of transcription.
FIG. 1C shows the release of the trans acting ribozyme. As a direct result of cleavage of the two cis-acting ribozymes, the internal ribozyme containing a reverse and complementary sequence to the mRNA target is released.

The catalytic component of multi-ribozyme invention is/are trans-acting internal targeted ribozyme (ITRz). To facilitate construction of this critical and catalytic component, the targeted triple ribozyme (TRz) containing a double ribozyme cassette was developed, as shown in FIG. 1. This artificially contrived genetic element consists of autocatalytic, self-cleaving 5' and 3' ribozymes, with a cloning region (denoted by the box entitled Targeted Ribozyme) between them. This double ribozyme cassette was then placed within a series of expression vectors that were either constructed (pClip), or modified from purchased from commercial vendors (pBluescriptII, Stratagene; pCRII, InVitrogen; pET-30a-c; pBACsurf-1, pIE1 and pIE4, Novagen) and used intact or modified as necessary to confer the desired activity within the Multi-ribozyme. pClip (the genetic element described in FIG. 2, was a modification of pbluescript, wherein the cassette shown is cloned into the Not I site in pBluescript. The targeted ribozyme (transacting catalytic ribozyme) was cloned into the Bgl II site (TGCTCT). Liberation of internal ribozymes from pClip resulted in a distribution of the catalytic core ribozyme(s) to approximately 20% nuclear and 80% cytoplasmic.

A second ribozyme cassette that was constructed was pChop. pChop was modified from pClip to convey a more efficient and effective liberation of the internal transacting ribozymes. The pChop ribozyme cassette is diagramed in FIG. 3. Liberation of internal catalytic core ribozymes from pChop increased localization to the nucleus.

A third ribozyme cassette that was constructed was the pSnip ribozyme cassette. The pSnip multi-ribozyme was constructed by engineering the pClip cassette 5' to pChop. In addition, the pSnip multi-ribozyme contained a catalytic core sequences with two trans-acting ribozymes in each cassette. Each pair of trans-acting ribozymes was linked by a short spacer and stabilized by a hairpin loop located 3' to the pair. FIG. 4 diagrams the schematic of the pSnip cassette. FIG. 5 diagrams the nucleotide sequence of the pSnip cassette indicating the sequence of the cis-acting cassette minus the internal ribozyme sequence.

An internal targeted ribozyme (ITRz) was synthesized as reverse complementary overlapping oligodeoxynucleotides, which were designed in such a way that when annealed they form single stranded ends identical to those produced by digestion with the restriction endonuclease contained with the region between the two cis-acting ribozymes. In this particular example the restriction endonuclease recognition site was that recognized by Bgl II.

An important advantage of the present invention is that essentially any RNA can be targeted, since specificity is conferred by selecting sequences for the ribozyme that are reverse and complementary to sequences flanking the chosen cleavage site in the targeted RNA molecule. The internal targeted ribozymes are then cloned into the cloning region within the double ribozyme cassette to produce the targeted trans-acting ribozyme. Internal targeted trans-acting ribozymes to prokaryotic sequences have been constructed including, but not limited to, *Escherichia coli*: secA (EcosecA, AE000119 U00096), gene X (EcosecA, AE000119 U00096) ftsZ (AE000119; U00096), dnaG (AE000388 U00096), rpoA (AE000407 U00096) and tRNA-asp (X14007), *Streptomyces lividins* secA (Z50195), *Enterococcus faecalis*, ftsZ (U94707) *Pseudomonas putida*, dnaG (U85774), *Streptomyces coelicolor* rpoA (X92107), *Staphylococcus warneri* tRNA, Asp (X66089 S42075), Staphloccocus RNA III.

Ribozyme Activity and Liberation of Internal Ribozymes

As shown in the autoradiograph of FIG. 7, the catalytic activity of ribozymes which are attached at either their 5' or 3' ends is not diminished. The constructs tested are diagramed in FIG. 6, 50 nM of the each of the constructs were incubated for 37° C. for 0.5 or 2 hours with target RNA (at about 50 nM). In this example, the transacting ribozymes of the constructs were targeted to multi-catalytic proteinase component C9. Following incubation, samples were denatured and separated on a polyacrylamide gel. The upper band represents the uncleaved target RNA whereas the lower bands represent the cleaved products. The data demonstrate that a ribozyme attached at either the 5' (lane 2) or 3' (lane 4) end of a transacting ribozyme does not diminish the catalytic activity of the ribozyme.

RT/PCT Analysis of TRz Expression and Self-Liberation in B2-X Clones. Cells were stably transfected with a B2-targeted PCLIP multi-ribozyme. FIG. 8A shows cytoplasmic RNA results, while FIG. 8B shows nuclear RNA results. These results demonstrate that there was a distribution of liberated transacting ribozymes between the nucleus and the cytoplasm. Most clones show 10 to 20% of the transacting ribozyme in the nucleus, although B2-1 was mostly cytoplasmic. 18s ribosomal RNA was amplified to document equivalent amounts of RNA.

An RT/PCR protocol was used for quantification of Rz expression, as well as for assessment of self-liberation of the ITRz in vivo. An "inner" set of primers was used in the RT/PCR reactions; these primers lie internal to the self-cleavage sites, and they effectively amplify both processed and unprocessed TRz transcripts. The upstream primer is 5'-AGCTCGAGCTCAGA (SEQ ID NO:6), and the downstream primer is 5'-TCGACGGATCTAGATCC (SEQ ID NO:7). Following self-cleavage of TRz transcripts, these primers were non-functional, so that they detect only unprocessed transcripts. To provide a baseline for the relative efficiency of the primer pairs, RT/PCR amplifications were performed with a mutant that does not undergo self-processing. One inner or outer primer was end labeled with $^{32}$P, and RT/PCR amplifications were performed with 2 μg cytoplasmic RNA. Following the reactions, samples were separated by PAGE in 6% polyacrylamide gels, the gels were dried and the radioactivity was detected by autoradiography and also using a phosphorimager. Product obtained with the inner primer pair was 1.8× greater than that obtained with the outer primer pair.

The following sequences are for ribozymes directed against the targets described. The naming system refers to the target cytosine in the GUC motif. It is the nucleotides number from the referenced sequence (accession number indicated). Ribozymes directed against secA targets have restriction sites for Bgl II on both ends. All other inserts have Bgl II (5 end) and Sty I (3 end) restriction sites for use in the new vector. Antisense arms are boldfaced.

```
Escherichia coli
ftsZ target (ACCESSION: AE000119 U00096)
   105  AGATCTAAACGCCGATCTGATGAGTCCGTGAGGACGAAACTTTAAAAACCAAGG    (SEQ ID NO: 54)

713  AGATCTAAACATCTCACTGATGAGTCCGTGAGGACGAAACATTACGAAACCAAGG   (SEQ ID NO: 55)

1131  AGATCTAAATCATTCACCTGATGAGTCCGTGAGGACGAAACTTTAGCAAACCAAGG  (SEQ ID NO: 8)

secA target (ACCESSION: AE000119 U00096)
    84  AGATCTAAAAAAAAACCTGATGAGTCCGTGAGGACGAAACTGGTTAAAAGATCT     (SEQ ID NO: 56)

707  AGATCTAAATTATCCACTGATGAGTCCGTGAGGACGAAACGGGCGAAAAGATCT     (SEQ ID NO: 57)

856  AGATCTAAATCGTTACCTGATGAGTCCGTGAGGACGAAACTACCGAAAAGATCT     (SEQ ID NO: 58)
```

-continued

```
  894 AFATCTAAATGATGTTCTGATGAGTCCGTGAGGACGAAACCACTTAAAAGATCT   (SEQ ID NO: 59)

979 AGATCTAAATTTTCCACTGATGAGTCCGTGAGGACGAAACGTGCAAAAAGATCT   (SEQ ID NO: 60)

1282 AGATCTAATTGATACCCTGATGAGTCCGTGAGGACGAAACAGTCAGAAAAGATCT  (SEQ ID NO: 61)

2216 AGATCTAAATTCGTTTCTGATGAGTCCGTGAGGACGAAACACCACAAAAGATCT   (SEQ ID NO:  9)

dnaG target (ACCESSION: AE000388 U00096)
 5344 AGATCTAAACGTTAGTCTGATGAGTCCGTGAGGACGAAACCAACAAAACCAAGG   (SEQ ID NO: 62)

5903 AGATCTAAAGGCATCACTGATGAGTCCGTGAGGACGAAACTGTTAAAACCAAGG   (SEQ ID NO: 63)

6336 AGATCTAAACCACATCCTGATGAGTCCGTGAGGACGAAACAGTTTAAACCAAGG   (SEQ ID NO: 10)
rpoA target (ACCESSION: AE000407 U00096)
 8308 AGATCTAAAAGAGCGCTGATGAGTCCGTGAGGACGAAACAGTCAAAACCAAGG    (SEQ ID NO: 64)

8494 AGATCTAAATTTCGATCTGATGAGTCCGTGAGGACGAAACCAGCTAAACCAAGG   (SEQ ID NO: 65)

8737 AGATCTAAACGATTTCCTGATGAGTCCGTGAGGACGAAACATCACCAAACC AAGG (SEQ ID NO: 11)
tRNA-Asp target
(directed against GUC anticodon loop. Accession: X14007)
  172 AGATCTAAATGCGTCTGATGAGTCCGTGAGGACGAAACAGGCAGGTAAAACCAAGG (SEQ ID NO:12)

Streptomyces lividans
secA target (ACCESSION: Z50195)
 1080 AGATCTAAACTCGTCCTGATGAGTCCGTGAGGACGAAACGATCAAAACCAAGG    (SEQ ID NO: 66)

2033 AGATCTAAAGGGCGCTGATGAGTCCGTGAGGACGAAACGCGAAAACCAAGG      (SEQ ID NO: 67)

2556 AGATCTAAAGTACTCCTGATGAGTCCGTGAGGACGAAACCAGCGAAACCAAGG    (SEQ ID NO: 13)

Enterococcus faecalis
ftsZ target (ACCESSION: U94707)
10805 AGATCTAAAACTAAATGCTGATGAGTCCGTGAGGACGAAACGAGTTAAAACCAAGG (SEQ ID NO: 68)

11182 AGATCTAAAGTTTAATAACTGATGAGTCCGTGAGGACGAAACTTGTTCAAACCAAGG (SEQ ID NO: 69)

11512 AGATCTAAAACTTTTGCTGATGAGTCCGTGAGGACGAAACGTGTATAAACCAAGG  (SEQ ID NO: 14)

Pseudomonas putida
dnaG target (ACCESSION: U85774)
  222 AGATCTAAAGGTCCATCTGATGAGTCCGTGAGGACGAAACAAAGCAAACCAAGG   (SEQ ID NO: 70)

986 AGATCTAAACAGGTTCCTGATGAGTCCGTGAGGACGAAACAATGTAAACCAAGG   (SEQ ID NO: 71)

1891 AGATCTAAATCGCTTTCTGATGAGTCCGTGAGGACGAAACGTGATAAACCAAGG   (SEQ ID NO: 15)

Streptomyces coelicolor
rpoA target (ACCESSION: X92107)
  290 AGATCTAAAGCTCGATCTGATGAGTCCGTGAGGACGAAACGAACCAAACCAAGG   (SEQ ID NO: 72)

716 AGATCTAAACGAGTCCTGATGAGTCCGTGAGGACGAAACCGGGAAACCAAGG     (SEQ ID NO: 73)

1099 AGATCTAAAGTCGATGCTGATGAGTCCGTGAGGACGAAACTTCGCAAACCAAGG   (SEQ ID NO: 16)

Staphylococcus warneri
tRNA-Asp target
(directed against GUC anticodon loop. Accession: x66089 s42075)
   62 AGATCTAAATGCGTCTGATGAGTCCGTGAGGACGAAACAGGCAGGCGAAACCAAGG (SEQ ID NO: 17)
```

The utility of the design using eukaryotic sequences has also been evaluated in the following examples: a) repetitive B2 transcripts (B2); b) RNA polymerase I (polI); c) Hepatitis B virus (HBV); d) Sonic Hedgehog (SH); e) Human Papillomavirus E6/E7 protein (HPV); f) RNA polymerase II (polII); g) Insulin-like Growth Factor 1 (IGF1); h) retinoblastoma protein (RB); i) and j) Multicatalytic Proteinase alpha-subunits C3 and C9 (C3 and C9, respectively); k) telomerase (tel); l) Transforming growth factor beta (TGFβ); m) catalase (CAT); n) Peroxisome proliferation associated receptor (PpaRα); and o) Cytochrome $P_{450}$ 1E1 (p4501E1). Target RNAs (with locus names and accession numbers) as well as the selected target sites are presented (Table 1), as are the sequences of these ITRz (SEQ ID NOS:18-36).

TABLE 1

Summary of Targeted RNAs and Target Sites.

| Target RNA | EMBL Locus | Accession | Target Site | Functional Testing in vitro | in vivo |
|---|---|---|---|---|---|
| pol II | HSRNAP14K | Z27113 | $GTC_{83}$ | ND | ND |
| HBV | XXHEPAV | X02496 | $GTC_{438}$ | IP | + |
| RB | MUSP105RB | M26391 | $GTC_{264}$ | + | + |
| IGF1 | HUMIGF1B | M37484 | $GTC_{185}$ | ND | ND |
| SH | MMEVX1 | X54239 | $GTC_{558}$ | IP | IP |
| Pol I | MUSRPA40 | D31966 | $GTC_{458}$ | + | + |
| HPV | PPH16 | K02718 | $GTT_{108}$ | IP | + |
| C3 | RATC3AA | J02897 | $GTT_{22}$ | + | + |

TABLE 1-continued

Summary of Targeted RNAs and Target Sites.

| Target RNA | EMBL Locus | Accession | Target Site | Functional Testing in vitro | in vivo |
|---|---|---|---|---|---|
| C9 | RNPTSC9 | X533304 | $GTC_{101}$ | + | + |
| B2 | B2-Consensus | ## | $GTT_{24}$ | + | + |
| Tel | MMU33831 | U33831 | $CTA_{63}$ | ND | ND | see Clawson, G. et al. Cell Growth Diff. 7: 635-646 (1996).

Multiple target sites have been selected for TGFb, CAT, PpaRa, and p4501E1. All of these ribozymes (with the exception of TGFb) have been functionally tested in vitro. Ribozymes targeted to catalase have also been tested in vivo. in vitro testing refers to. target cutting. in vivo testing refers to cell culture experiments or transgenic animals (for polI). IP, in progress. ND, not yet determined. +, substantially decreased target RNA (and/or protein).

For many of these constructs, "mutants" have also been created by substituting an A for a G, or a G for an A, at nucleotides which are absolutely required for catalytic activity. These "mutants" allow evidence indicating that the efficiency of destruction of the targeted RNAs is due to ribozyme catalytic activity and not to antisense effects.

The eukaryotic cell contains large families of short repetitive sequences throughout its genome.

Although B2 RNA transcripts are normally confined to the nucleus, they appear in the cytoplasm of malignant cells, and in cell lines immortalized with SV40 or papillomavirus as well as in undifferentiated embryonal carcinoma cells.

Multi-Ribozyme-Mediated Down Regulation of B2 Transcripts

The B2 family represents a group of short repetitive sequences which are found throughout the rodent genome and are analogous to the human Alu sequences. Certain B2 subfamilies are transcribed by RNA polymerase III, and this transcription is in part controlled by the retinoblastoma pro-

```
B2              TGCTCTT CTGATGAGTCCGTGAGGACGAAA (SEQ ID NO: 18)
                CCGCCTGA

Pol 1           TTCAAAGA CTGATGAGTCCGTGAGGAC-   (SEQ ID NO: 19)
                GAAA CGAGGATC

Sonic Hedgehog  GTCCAT CTGATGAGTCCGTGAGGACGAAA  (SEQ ID NO: 20)
                CCGGC HBV             ATTAGAG CTGATGAGTCCGTGAGGACGAAA (SEQ ID NO: 21)
                CAAACG HPV             GTCCTGA CTGATGAGTCCGTGAGGACGAAA (SEQ ID NO: 22)
                CATTGCA Pol III         TCCGTTGTCT CTGATGAGTCCGTGAGGAC- (SEQ ID NO: 23)
                GAAA CATGACACCGA IGF-1           GCGAGGAG CTGATGAGTCCGTGAGGAC-   (SEQ ID NO: 24)
                GAAA CATGGTGT RB              AACTTTT CTGATGAGTCCGTGAGGACGAAA (SEQ ID NO: 25)
                CATAATG C3              TCGAAGCTGT CTGATGAGTCCGTGAGGAC- (SEQ ID NO: 26)
                GAAA CCGCGTTGA TEL             ATCAGGGT CTGATGAGTCCGTGAGGAC-   (SEQ ID NO: 27)
                GAAA GGTGCC C9              TCTTCGA CTGATGAGTCCGTGAGGACGAAA (SEQ ID NO: 28)
                CATGGCT TGFβ-1          TAGCACA CTGATGAGTCCGTGAGGACGAAA (SEQ ID NO: 29)
                CGTTTGA CAT/#13         TGCAATA CTGATGAGTCCGTGAGGACGAAA (SEQ ID NO: 30)
                CTGCCT CAT/#15         AAGTCAT CTGATGAGTCCGTGAGGACGAAA (SEQ ID NO: 31)
                CCTGGA PpaRa/#2        GATAAGG CTGATGAGTCCGTGAGGACGAAA (SEQ ID NO: 32)
                CTTTCC PpaRa/#8        CATATTC CTGATGAGTCCGTGAGGACGAAA (SEQ ID NO: 33)
                CACTCG PpaRa/#14       TCATGTAT CTGATGAGTCCGTGAGGAC-   (SEQ ID NO: 34)
                GAAA CAAAAGG p4501E1/#2      GGTTAAA CTGATGAGTCCGTGAGGACGAAA (SEQ ID NO: 35)
                CTTGGG p4501E1/#8      GTCCAGT CTGATGAGTCCGTGAGGACGAAA (SEQ ID NO: 36)
                CTTAAG
``` tein. These actively transcribed B2 RNAs show a predicted highly stable secondary structure.

The retinoblastoma protein gene protein (pRb) has recently been shown to act as a regular of pol III transcription 47, and pRb-mediated growth arrest has been hypothesized to result from transcriptional blockade of tRNA synthesis, with consequent decreased protein synthetic capacity. Therefore, it was important to determine whether the alterations observed in B2 levels, by the inventors, might reflect alterations in pRb expression and/or interactions.

Construction and In Vitro Testing of the B2-targeted Triple Ribozyme

For construction of the B2-targeted triple ribozyme, oligodeoxynucleotides were synthesized. The following oligodeoxynucleotides were used to construct the parent double ribozyme by the polymerase chain reaction;

```
primer 1: 5'-CCCGGGAATTCGTGATGGCCACGCGGCC  (SEQ ID
                                           NO: 37)
          GCTCGAGCTCTGATGAGTCCGTGAGGA-3' primer 2: 5'-GACGGGATCCAGATCTGAGCTCGAGCTG  (SEQ ID
                                           NO: 38)
          ACGGTACCGGGTACCGTTTCGTCCT-
          CACGGA-3' primer 3: 5'-GAGCTCAGATCTGGATCCGTCGACGGAT  (SEQ ID
                                           NO: 39)
          CTAGATCCGTCCTGATGAGTCCGTGAG-3' primer 4: 5'-TTGCTTGGCCAGCGGCCGCTGCAGATCC  (SEQ ID
                                           NO: 40)
          GTTTCGTCCTCACGGACT-3'
```

Primer pairs 1 and 2, or 3 and 4 were annealed and amplified by PCR using a MiniCycler (MJ Research). PCR reaction products were then digested with BglII and ligated with T4 DNA ligase. The resultant 173 bp fragment was isolated from a 3.75% low-melting temperature agarose gel (SeaPlague, from FMC BioProducts) and subsequently purified using Wizard PCR kits (Promega). The recovered fragment was amplified by PCR using primer 1 and 4, and the PCR product was then digested with NotI and ligated into 100 ng NotI-digested pOPRSVICAT mammalian expression vector (Lac-Switch, from Stratagene), which contains a neomycin resistance gene. This parent double ribozyme was designated pClip.

The B2 targeted internal ribozyme was then made by annealing 100 pmol each of the primers: 5'-GATCTGCTCT-TCTGATGAGTCCGTGAGGACGAAACCGCTGA-3' (SEQ ID NO:41) and 5'-GATCTCAGCGGTTTCGTCCT-CACGGACTCATCAGAAGAGCA-3' (SEQ ID NO:42). For annealing, primers were boiled for 3 minutes in 10 mM Tris-HCl, pH 8.5, 100 mM $MgCl_2$ and then slowly cooled to room temperature. After annealing, product was precipitated with ethanol and ligated into BglII digested pClip at a 1:5 molar ratio. The final pClip-B2 construct was verified by sequencing. For in vitro expression, the B2-targeted TRz was inserted into the NotI site of the pCRII vector, and M13 forward and reverse primers were used in PCR to amplify the region containing the B2-targeted Trz.

Characterization and Validation of the TRz Construct

Typically, once the recombinant plasmid has been created the TRz constructs are isolated from the bacterium their nucleotide sequence is determined to confirm their identities and to document their orientation within the vector. The constructs are then transcribed in vitro using SP6 and T7 RNA polymerases with $^{32}$P-CTP. When transcribed in the "sense"

orientation, all of these TRz constructs should be "self-liberating"; that is, the 5' and 3' self-cleaving autocatalyic ribozymes work effectively, freeing the ITRz during (or immediately after) transcription (FIG. 1c). The 5' liberated ribozyme (whose only function is self-cleavage, liberating the 5' end of the ITRz) is associated with relatively short stretches of vector sequences and the 3' self-cleaving ribozyme (whose only function is self-cleavage, liberating the 3' end of the ITRz) remains associated with long vector sequences. The liberated ITRz achieves its catalytic topology upon hybridization with the targeted sequence. Transcription of all of these TRz in the "antisense" direction should not result in self-cleavage.

In Vitro Evaluation

Upon validation of the TRz construct, the self-liberating TRz is evaluated for their ability to effectively cut their targeted RNAs. Appropriate regions of the targeted RNAs are generally cloned using cellular RNA and reverse transcription/polymerase chain reaction amplifications. In some cases, cloned full-length cellular RNAs are also used. The identities of the constructs used for transcription of target RNAs are also confirmed by sequencing. Target RNAs are then synthesized in vitro using the appropriate T7/SP6 RNA polymerase with $^{32}$P-CTP, and are subsequently gel-purified. A preparation of the TRz under evaluation is then synthesized without $^{32}$P-CTP. The TRz preparation is then mixed with their an appropriate concentration of radiometrically $^{32}$P-labeled target or substrate RNA ($^{32}$P-labeled target RNAs and unlabeled TRz preparations are mixed at a 10:1 molar ratio) and is incubated for various lengths of time. Following incubations, the RNA is examined using polyacrylamide gel electrophoresis (PAGE) and autoradiography. All of the constructs tested should be able to cleave their target RNAs. In general, the data show an approximate catalytic rate of 0.2 cleavages/ribozyme minute.

In Vivo Evaluation

The TRz is evaluated with intact cells. The TRz cassette is excised from the parental plasmid and is then placed into an appropriate expression vector. Vectors utilized include (but are not limited to) the LacSwitch vector (from Stratagene), which is an IPTG-inducible system, and the TetSplice vector (from Gibco-BRL), which is a tetracycline-inducible system.

The TRz constructs in these expression vectors were then transfected into cells using standard techniques. Cell types used in transfections have included E. coli, human CaSki cervical carcinoma cells, SV-40 immortalized rat hepatocytes, and mouse fibroblasts. In transient transfection analyses, all constructs tested produced substantial reductions in their respective target RNAs, thus demonstrating the effectiveness of the multi-ribozymes of the invention.

TRz Construct 1:

The secA targeted TRz construct against the secA gene of E. coli is in the vector pClip, which is a variation of the generalized cloning vector, pBluescript of Stratagene. The plasmid containing the construct was transformed into competent bacterial cells and cells containing the plasmid with the TRz were selected by using the antibiotic selectable marker within the vector, pClip. Upon induction of the promoter with isopropyl-β-D thiogalactoside, (IPTG) the effect of ribozyme expression is monitored by standard bacterial viable counts. A reduction in total viable cells is an indication of synthesis and catalytic activity of the TRz against the essential target.

TRz Construct 2:

The polI-targeted TRz construct (in LacSwitch vector) was used in transfections of SV40-immortalized rat hepatocytes (CWSV1 cells), and stably transfected cell populations were obtained. Cells not transfected with the antibiotic resistance plasmid were all dead by day 5, indicating that the antibiotic selection procedure was effective. Growth of cells transfected with the double ribozyme (as a control, with no cellular RNA target), and of cells expressing the catalytically inactive "mutant" polI TRz, was unaffected. However, growth of cells expressing the polI-targeted TRz was depressed by nearly 90%. Concurrently, the mRNA for polI was decreased by at least 70% from polI mRNA levels in the cells expressing the mutant polI TRz. Since expression of the TRz was essentially equivalent for the two TRz, this clearly documents that the effects on cell growth are due to TRz catalytic activity and not to antisense effects. In other experiments, expression of the polI-TRz in LacSwitch resulted in cell death with mouse fibroblast cell populations.

TRz Constructs 3:

The RB-targeted TRz (in the tetracycline-inducible TetSplice vector system) was used in transfections with CWSV1 cells, and stably transfected cells were selected using G418 antibiotic in the presence of tetracycline, and individual clones were harvested and used (expression of RB-targeted TRz is "off" in the presence of tetracycline, and is "on" in the absence of tetracycline). Expression of the RB-targeted TRz had no effect on cell growth, as expected. Expression of RB mRNA was substantially reduced to below detectable levels by Northern blot analysis. To extend this result, metabolic labeling of proteins was performed using $^{35}$S-methionine, and immunoprecipitations were performed using an antibody directed against RB. The data show that RB protein levels were reduced by 75%, comparing clonal cell populations grown in the presence vs. absence of tetracycline, even after only 18 h of induction of RB-targeted TRz expression (removal of tetracycline). This shows that the effects of the reduction in RB RNA levels also extends to the production of the RB protein. In addition, the (+)-tetracycline sample provides an ideal control, since it represents the exact same clonal cell line. Essentially any inducible vector system can be used in parallel fashion.

TRz Constructs 4:

The B2-targeted TRz (in the IPTG-inducible LacSwitch vector) was used in transfections of CWSV1 cells, and antibiotic selection was used to obtain a number of individual clones. Reductions in cytoplasmic B2 RNA levels of up to 80% were observed by Northern blot analysis, and growth of transfected clones was reduced in parallel. In fact, a linear relationship between growth rate and B2 RNA levels was observed. The reductions in B2 transcripts paralleled the level of B2-targeted TRz expression (as determined by slot-blot analysis). The B2 target RNA is of additional interest, because B2 transcripts are not translated (i.e., they are not mRNAs) and they are abundant, highly-structured RNAs.

Other TRz constructs have also been successfully tested using this methodology (including C9 in the tetracycline-inducible system, and CAT, BRAC1 and Albumin driven by the albumin promoter in HepG2 cells).

Multi-Ribozyme-Mediated Down Regulation of NfκB p50 Subunit Target

Another target of the ribozymes of the invention is the NfκB p50 subunit. Six ribozymes (named RZ615, RZ636, RZ649, RZ1024, RZ1380 and RZ1438) were designed against the NfκB p50 subunit target. Results of in vitro cleavage assays, show in FIG. 11, demonstrate that the ribozymes cleave the target NfκB p50 substrate, as indicated by the presence of fragments generated by following incubation of the ribozyme and substrate. The in vitro substrate cleavage assay was performed by in vitro transcription of NFκB p50 subunit in the presence of $P^{32}$ nucleotide, so the p50 transcript (substrate) was radiolabeled. The ribozyme was also transcribed in vitro. The ribozyme was then incubated with the $P^{32}$-labeled p50 messenger RNA for 45 minutes at 37° C. The reaction mixtures were then resolved by a 6% TBE-urea gel and exposed to film by methods known in the art. The following sequences were constructed for the ribozyme constructs; the capitalized sequences correspond to the two arms of each ribozyme which match the target p50 sequence.

```
RZ615:   5'ctt gga acc gga tgc cag gca tcc ggt tGG TGC CTt tcg tcc tca   (SEQ ID NO: 43)
         cgg act cat cag TAG TGA a RZ636:   5'ctt gga acc gga tgc cag gca tcc ggt tAA GAA GTt tcg tcc tca   (SEQ ID NO: 44)
         cgg act cat cag TTA CCC Ta RZ649:   5'aat tca acc gga tgc cag gca tcc ggt tCT CAG GTt tcg tcc tca   (SEQ ID NO: 45)
         cgg act cat cag AAA ATC Tg RZ1024:  5'aat tca acc gga tgc cag gca tcc ggt tTG GAC CTt tcg tcc tca   (SEQ ID NO: 46)
         cgg act cat cag AGC GTG g RZ1380:  5'aat tca acc gga tgc cag gca tcc ggt tCA GCC Ttt cgt cct cac   (SEQ ID NO: 47)
         gga ctc atc agT GTG TTg RZ1438:  5'aat tca acc gga tgc cag gca tcc ggt tAA CCT TTt tcg tcc tca   (SEQ ID NO: 48)
         cgg act cat cag CTC TAC g
```

In order to demonstrate that the ribozymes designed against NfκB were able to cleave the NFκB mRNA and cause a decrease in NFκB expression, the effect of Ribozyme-1024 (RZ1024) on the TNFα-induced production of IL-6 was assayed in A549 cells. TNFα is known to act via a signal transduction cascade to activate NFκB. The activated NFκB induces the expression of cytokines such as IL-6. Thus, a decrease in the production of IL-6 can act as a readout for one of the downstream effects of the NFκB activation pathway.

A549 cells are human lung cancer cells, which express NFκB and respond to NFκB activation stimulus such as TNFα, LPS, etc. Ribozyme RZ1024 was cloned into the pCDNA 3.1 vector such that the expression of the ribozyme was driven by the CMV promoter. A549 cells were then stably transfected with the ribozyme RZ1024-pCDNA 3.1 construct. As depicted in FIG. 12, eight independent clones were established and designated as C2, C6, C7, C12, C19, C20, C21, and C22. The stable clones were then treated with TNFα (100 ng/ml) for 7 hrs. Control (ctrl) represents untransfected A549 cells. After the TNFα treatment, media were collected for measuring secreted IL-6 using ELISA, and cells were harvested for total protein assay. As shown in FIG. 12, the TNFα-induced production of secreted IL-6 decreased, by 50% to 90%, in the eight clones transfected with ribozyme RZ1024 construct. Thus, the ribozymes of the invention are capable of targeting and cleaving a target RNA in vitro and in vivo.

Throughout this application various publications are referenced; the disclosures of the publications cited herein above are hereby incorporated by reference in their entireties into this application in order to more fully describe the state of the art to which this invention pertains.

What is claimed is:

1. A recombinant nucleic acid comprising a nucleotide sequence encoding a 7:20 cis-acting ribozyme, a trans-acting ribozyme, and a 18:7 cis-acting ribozyme, wherein said 7:20 cis-acting ribozyme comprises the sequence of SEQ ID NO:53 from position 7 to position 91, and wherein said 18:7 cis-acting ribozyme comprises the sequence of SEQ ID NO:53 from position 110 to position 190.

2. The recombinant nucleic acid of claim 1, wherein said recombinant nucleic acid comprises an origin of replication.

3. The recombinant nucleic acid of claim 1, wherein said recombinant nucleic acid encodes more than one trans-acting ribozyme.

4. The recombinant nucleic acid of claim 3, wherein the trans-acting ribozymes are targeted to different sites on the same target-RNA.

5. The recombinant nucleic acid of claim 3, wherein the trans-acting ribozymes are targeted to different target-RNAs.

6. The recombinant nucleic acid of claim 1, wherein said recombinant nucleic acid encodes more than one ribozyme cassette.

7. The recombinant nucleic acid of claim 1, wherein said recombinant nucleic acid encodes at least two different ribozymes cassettes.

8. The recombinant nucleic acid of claim 1, wherein said recombinant nucleic acid encodes more than one copy of a ribozyme cassette.

9. The recombinant nucleic acid of claim 1, wherein said trans-acting ribozyme is targeted to a transcript selected from the group consisting of: pol II, HBV, pol III, RB, IGF1, SH, polI, HPV, C3, C9, B2, Tel, TGFJ, CAT, PpaRI, p450E1, AR, and SF1 transcripts.

10. The recombinant nucleic acid of claim 1, wherein said nucleotide sequence encodes a hairpin loop.

11. The recombinant nucleic acid of claim 1, wherein said nucleotide sequence encodes multiple ribozyme cassettes linked together by at least 4 nucleotides.

12. The recombinant nucleic acid of claim 1, wherein said nucleic acid further comprises a tissue-specific promoter is selected from the group consisting of a K4 promoter, K7 promoter, K13 promoter and albumin promoter.

13. An isolated cell containing a recombinant nucleic acid comprising a nucleotide sequence encoding a 7:20 cis-acting ribozyme, a trans-acting ribozyme, and a 18:7 cis-acting ribozyme, wherein said 7:20 cis-acting ribozyme comprises the sequence of SEQ ID NO:53 from position 7 to position 91, and wherein said 18:7 cis-acting ribozyme comprises the sequence of SEQ ID NO:53 from position 110 to position 190.

14. A virion comprising a recombinant nucleic acid comprising a nucleotide sequence encoding a 7:20 cis-acting ribozyme, a trans-acting ribozyme, and a 18:7 cis-acting ribozyme, wherein said 7:20 cis-acting ribozyme comprises the sequence of SEQ ID NO:53 from position 7 to position 91, and wherein said 18:7 cis-acting ribozyme comprises the sequence of SEQ ID NO:53 from position 110 to position 190.

15. A liposome composition comprising a recombinant nucleic acid comprising a nucleotide sequence encoding a 7:20 cis-acting ribozyme, a trans-acting ribozyme, and a 18:7 cis-acting ribozyme, wherein said 7:20 cis-acting ribozyme comprises the sequence of SEQ ID NO:53 from position 7 to position 91, and wherein said 18:7 cis-acting ribozyme comprises the sequence of SEQ ID NO:53 from position 110 to position 190.

* * * * *

UNITED STATES PATENT AND TRADEMARK OFFICE
CERTIFICATE OF CORRECTION

PATENT NO. : 7,732,197 B2
APPLICATION NO. : 10/082973
DATED : June 8, 2010
INVENTOR(S) : James S. Norris It is certified that error appears in the above-identified patent and that said Letters Patent is hereby corrected as shown below:

Title Page, please insert Item (63)

--Related U.S. Application Data

(63) Continuation of application No. 09/338,942, filed on Jun. 24, 1999, which claims the benefit of prior application No. 60/090,560 filed on Jun. 24, 1998, and prior application No. 60/096,502 filed on Aug. 14, 1998.--;

In the Specification:

Column 1, line 3, please insert the following heading --Related Application Data--;

Column 1, line 4, after "priority" please insert --of application No. 09/338,942, filed on Jun. 24, 1999, which claims the benefit--;

In the Claims:

Column 71, line 49 (Claim 9), please delete "poll," and insert --pol I,-- therefor;

Column 71, line 49 (Claim 9), please delete "TGFJ," and insert --TGFβ,-- therefor;

Column 71, line 49 (Claim 9), please delete "PpaRI, p450E1," and insert --PpaRα, p4501E1,-- therefor.

Signed and Sealed this

Twenty-fourth Day of August, 2010

David J. Kappos
*Director of the United States Patent and Trademark Office*